(12) United States Patent
Richardson et al.

(10) Patent No.: US 10,456,537 B2
(45) Date of Patent: Oct. 29, 2019

(54) DEVICES AND METHODS FOR DELIVERING DRY POWDER MEDICAMENTS

(71) Applicant: Concentrx Pharmaceuticals, Inc., Durham, NC (US)

(72) Inventors: Eric C. Richardson, Cave Creek, AZ (US); Gilbert S. Mott, Jr., Durham, NC (US); William James Alexander, Cary, NC (US)

(73) Assignee: CONCENTRX PHARMACEUTICALS, INC., Durham, NC (US)

( * ) Notice: Subject to any disclaimer, the term of this patent is extended or adjusted under 35 U.S.C. 154(b) by 0 days.

(21) Appl. No.: 15/938,766

(22) Filed: Mar. 28, 2018

(65) Prior Publication Data

US 2018/0280639 A1 Oct. 4, 2018

Related U.S. Application Data

(60) Provisional application No. 62/477,506, filed on Mar. 28, 2017.

(51) Int. Cl.
*A61M 15/00* (2006.01)
*A61K 9/00* (2006.01)

(52) U.S. Cl.
CPC ....... *A61M 15/0086* (2013.01); *A61K 9/0075* (2013.01); *A61M 15/0008* (2014.02);
(Continued)

(58) Field of Classification Search
CPC .............. A61M 15/008; A61M 15/002; A61M 15/0021; A61M 15/0028; A61M 15/0043;
(Continued)

(56) References Cited

U.S. PATENT DOCUMENTS

| 4,206,758 A | 6/1980 | Hallworth et al. |
| 4,841,964 A | 6/1989 | Hurka et al. |

(Continued)

FOREIGN PATENT DOCUMENTS

| DE | 10027639 A1 | 12/2001 |
| WO | WO1992004928 A2 | 4/1992 |

(Continued)

OTHER PUBLICATIONS

International Search Report for PCT Application No. PCT/US2012/054325, dated Feb. 26, 2013.
(Continued)

*Primary Examiner* — Steven O Douglas
(74) *Attorney, Agent, or Firm* — ReavesColey PLLC

(57) ABSTRACT

An apparatus includes a first member coupled to a second member. The first member defines a chamber containing a dry powder and includes a chamber wall that forms an outer boundary of the chamber. The second member includes a surface covering the chamber and defines an intake channel and an exit channel. The exit channel is fluidically coupled to the chamber via an exit opening. The intake channel is fluidically coupled to the chamber via an intake port. A center line of the intake channel is tangential to a portion of the chamber wall such that a portion of an inlet airflow conveyed into the chamber via the intake channel has a rotational motion. The intake port is defined at least in part by an intake ramp. The intake ramp includes a transition surface that forms an exit angle with respect to the surface of less than 105 degrees.

26 Claims, 33 Drawing Sheets

(52) U.S. Cl.
CPC ... *A61M 15/0028* (2013.01); *A61M 2202/064* (2013.01); *A61M 2206/16* (2013.01)

(58) Field of Classification Search
CPC ........ A61M 2202/064; A61M 2202/16; A61M 2202/10; A61M 15/0001; A61M 15/005; A61M 2206/16; A61J 1/00; A61J 1/03; A61J 1/35; A61J 1/202; A61J 1/2024; A61J 1/2041; A61K 9/0075
See application file for complete search history.

(56) References Cited

U.S. PATENT DOCUMENTS

| | | |
|---|---|---|
| 5,239,991 A | 8/1993 | Chawla et al. |
| 5,239,993 A | 8/1993 | Evans |
| 5,533,505 A | 7/1996 | Kallstrand et al. |
| 5,660,169 A | 8/1997 | Kallstrand et al. |
| 5,918,594 A | 7/1999 | Asking et al. |
| 6,102,035 A | 8/2000 | Asking et al. |
| 6,105,574 A | 8/2000 | Jahnsson |
| 6,286,507 B1 | 9/2001 | Jahnsson |
| 6,427,688 B1 | 8/2002 | Ligotke et al. |
| 6,715,486 B2 | 4/2004 | Gieschen et al. |
| 6,971,384 B2 | 12/2005 | Gieschen et al. |
| 7,069,929 B2 | 7/2006 | Young et al. |
| 7,143,765 B2 | 12/2006 | Asking et al. |
| 7,322,353 B2 | 1/2008 | Young et al. |
| 7,322,354 B2 | 1/2008 | Young et al. |
| 7,434,579 B2 | 10/2008 | Young et al. |
| 7,533,668 B1 | 5/2009 | Widerstrom |
| 7,617,822 B2 * | 11/2009 | De Boer ........... A61M 15/0045 128/203.12 |
| 7,661,425 B2 | 2/2010 | Keldmann et al. |
| 7,861,712 B2 | 1/2011 | Jones et al. |
| 7,958,890 B2 | 6/2011 | Gieschen et al. |
| 8,550,074 B2 | 10/2013 | Jones et al. |
| 9,446,209 B2 | 9/2016 | Richardson |
| 2001/0027790 A1 | 10/2001 | Gieschen et al. |
| 2002/0092523 A1 | 7/2002 | Connelly et al. |
| 2002/0108611 A1 | 8/2002 | Johnston et al. |
| 2004/0065329 A1 | 4/2004 | Geist |
| 2004/0168687 A1 | 9/2004 | Asking et al. |
| 2004/0200475 A1 | 10/2004 | Koane et al. |
| 2005/0048003 A1 | 3/2005 | Ohki et al. |
| 2005/0081851 A1 | 4/2005 | Young et al. |
| 2005/0118111 A1 | 6/2005 | Goldemann |
| 2005/0252510 A1 | 11/2005 | Young et al. |
| 2006/0237010 A1 * | 10/2006 | De Boer ........... A61M 15/0045 128/203.15 |
| 2007/0081948 A1 | 4/2007 | Morton et al. |
| 2007/0151562 A1 | 7/2007 | Jones et al. |
| 2008/0173302 A1 | 7/2008 | Mecikalski |
| 2008/0190424 A1 * | 8/2008 | Lucking ............... A61K 9/0075 128/203.15 |
| 2008/0314384 A1 | 12/2008 | Harris et al. |
| 2009/0013994 A1 | 1/2009 | Jones et al. |
| 2009/0084379 A1 | 4/2009 | Goeckner |
| 2009/0223516 A1 | 9/2009 | Connelly et al. |
| 2009/0235930 A1 | 9/2009 | Young et al. |
| 2009/0235931 A1 | 9/2009 | Young et al. |
| 2009/0250058 A1 | 10/2009 | Lastow et al. |
| 2009/0308391 A1 | 12/2009 | Smutney et al. |
| 2010/0000531 A1 | 1/2010 | Smith et al. |
| 2010/0059049 A1 | 3/2010 | Genosar |
| 2010/0139655 A1 | 6/2010 | Genosar et al. |
| 2010/0181387 A1 | 7/2010 | Zaffaroni et al. |
| 2010/0212667 A1 | 8/2010 | Smith et al. |
| 2011/0061653 A1 | 3/2011 | Von Schuckmann |
| 2011/0192397 A1 | 8/2011 | Saskar et al. |
| 2012/0132204 A1 | 5/2012 | Lucking et al. |
| 2013/0008442 A1 | 1/2013 | Jones et al. |
| 2013/0025593 A1 | 1/2013 | Thirumalai Anandampillai |
| 2013/0061851 A1 | 3/2013 | Jones et al. |
| 2013/0199527 A1 | 8/2013 | Smutney et al. |
| 2013/0291865 A1 | 11/2013 | Jones et al. |
| 2014/0083423 A1 | 3/2014 | Jung et al. |
| 2017/0000960 A1 | 1/2017 | Richardson |
| 2017/0119982 A1 | 5/2017 | Jones et al. |
| 2017/0312458 A1 | 11/2017 | Beller |

FOREIGN PATENT DOCUMENTS

| | | |
|---|---|---|
| WO | WO199413348 A1 | 6/1994 |
| WO | WO9419041 A1 | 9/1994 |
| WO | WO9834661 A1 | 8/1998 |
| WO | WO2000/53248 A1 | 9/2000 |
| WO | WO2003/000325 A1 | 1/2003 |
| WO | WO2003/103563 A2 | 12/2003 |
| WO | WO2008/042951 A2 | 4/2008 |
| WO | WO2009/009013 A2 | 1/2009 |
| WO | WO2009/121020 A1 | 10/2009 |
| WO | WO2009/133555 A1 | 11/2009 |
| WO | WO2012/088585 A1 | 7/2012 |
| WO | WO2015/097034 A1 | 7/2015 |
| WO | WO2016/193379 A1 | 12/2016 |

OTHER PUBLICATIONS

European Search Report for EP Application No. 12830544, dated Feb. 26, 2013.
Office Action for Chinese Patent Application No. 201280054580.1, dated Jul. 28, 2015.
Office Action for Chinese Patent Application No. 201280054580.1, dated Mar. 31, 2016.
Office Action for U.S. Appl. No. 14/343,498, dated Jun. 21, 2016.
Chrystyn, H. The Diskus: a review of its position among dry powder inhaler devices. International Journal of Clinical Practice, Jun. 2007, 61, 6, pp. 1022-1036. 15 pages.
International Search Report for PCT Application No. PCT/US2018/024882, dated Jun. 25, 2018.
Office Action for U.S. Appl. No. 15/265,428, dated Oct. 9, 2018.
First Office Action for Chinese Patent Application No. 201611041479.9, dated Mar. 25, 2019.

* cited by examiner

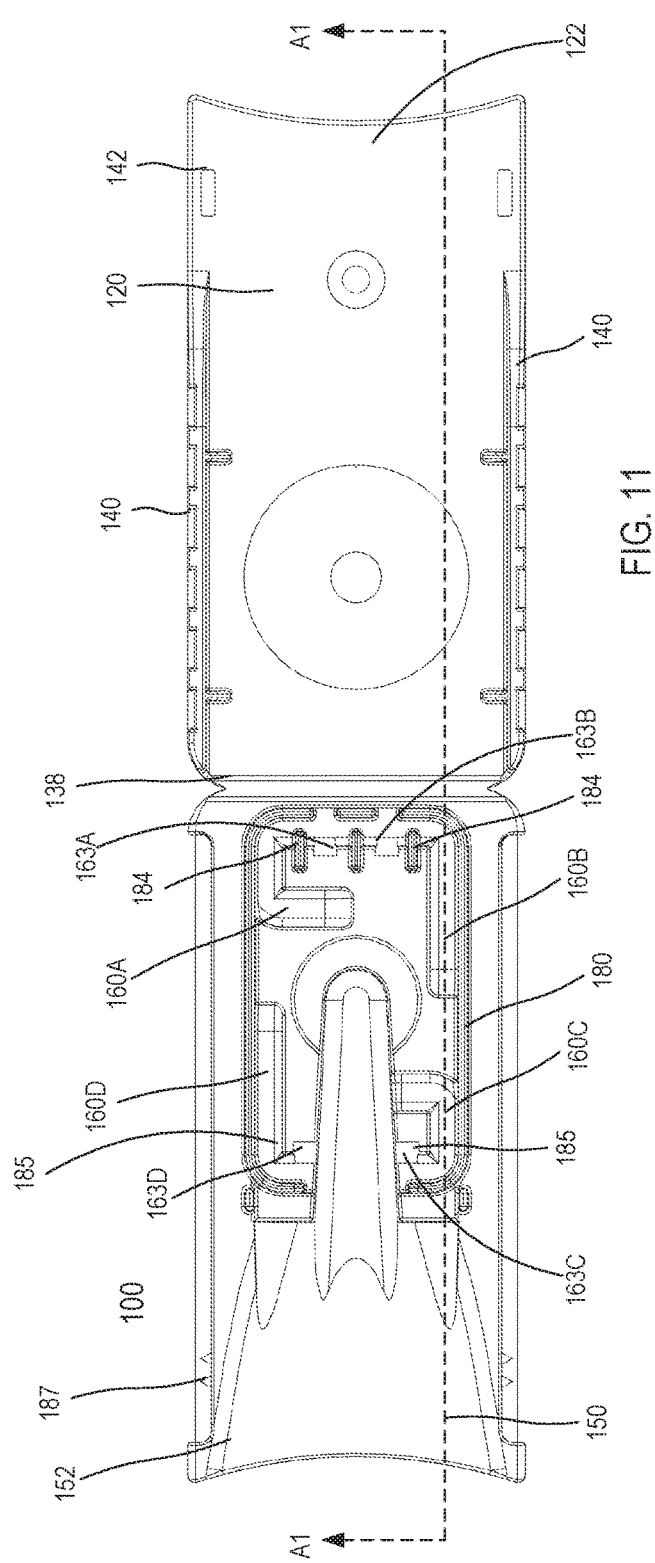
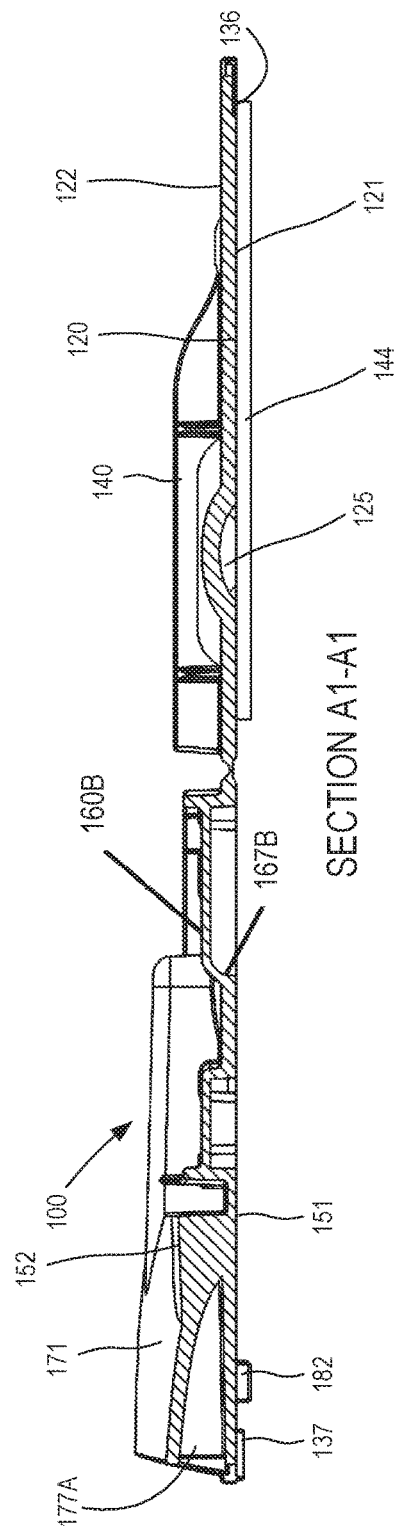
FIG. 11
FIG. 12
SECTION A1-A1

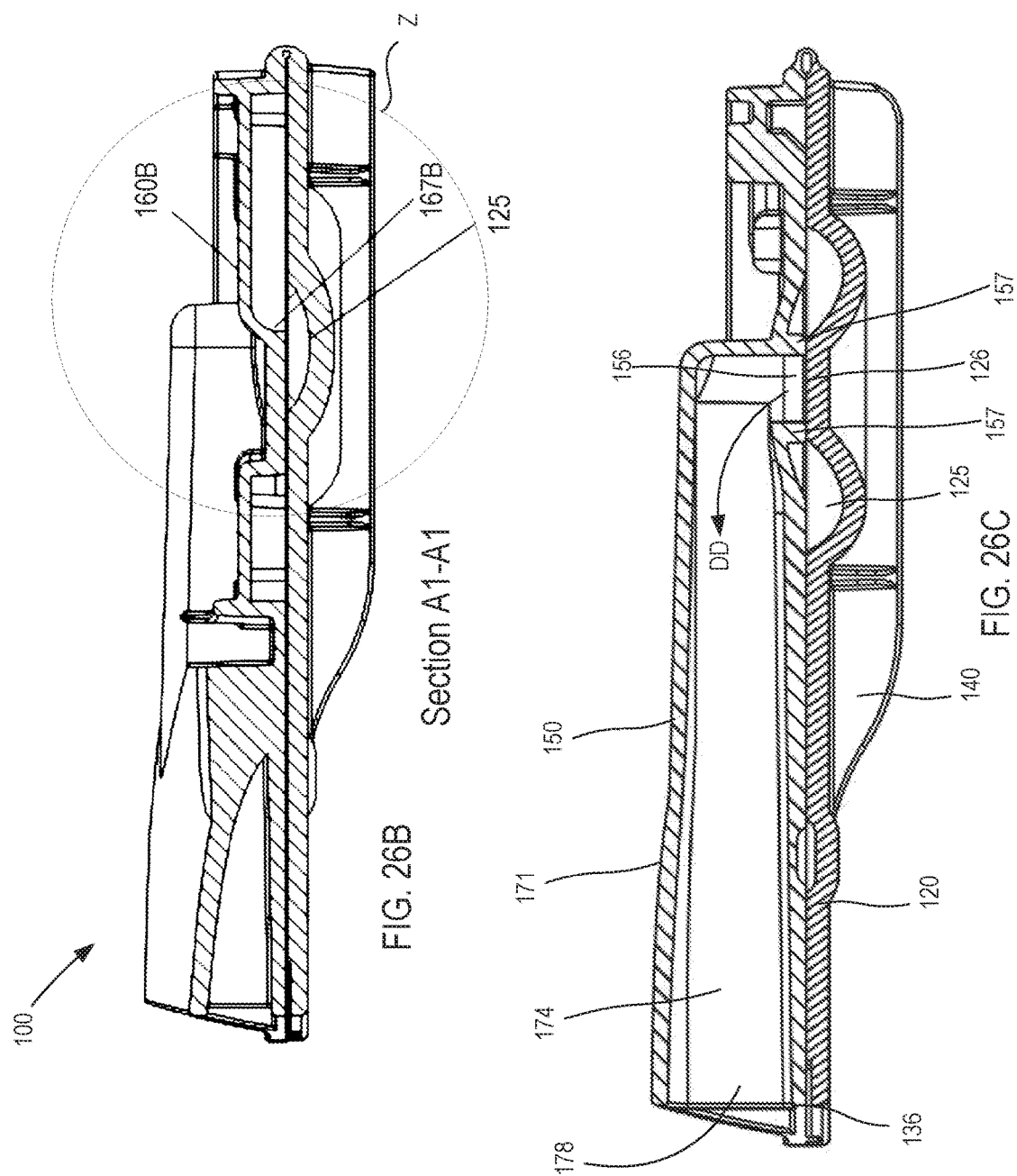

10

12 — Move a strip from a first position between a first member of a dry powder inhaler and a second member of the dry powder inhaler to a second position, the strip sealing a dry powder within a portion of a disaggregation chamber defined by a chamber wall of the first member when the strip is in the first position, the portion of the disaggregation chamber in fluid communication with an exit channel defined by the second member and an intake channel defined by the second member when the strip is in the second position 14 — Place a mouthpiece of the dry powder inhaler into a mouth 16 — Inhale into the mouth to draw an inlet airflow through the intake channel and into the disaggregation chamber, a portion of the intake channel is shaped and positioned such that a portion of an inlet airflow has a rotational motion within the disaggregation chamber, the rotational motion disaggregating the dry powder to produce a plurality of respirable particles within the inlet airflow, the intake channel and the exit channel collectively configured to produce an exit airflow containing the plurality of respirable particles for at least two seconds 17 — Optionally, dispose of the dry powder inhaler, including the first member and the second member

FIG. 30

DEVICES AND METHODS FOR DELIVERING DRY POWDER MEDICAMENTS

CROSS-REFERENCE TO RELATED APPLICATIONS

This application claims benefit of priority to U.S. Provisional Application Ser. No. 62/477,506, entitled "Devices and Methods for Delivering Dry Powder Medicaments," filed Mar. 28, 2017, which is incorporated herein by reference in its entirety.

BACKGROUND

The embodiments described herein relate generally to medical devices and pharmaceutical compositions, and more particularly to drug products for delivery of dry powder medicaments.

Pressurized metered dose inhalation devices (pMDI) are well-known for delivering drugs to patients by way of their lungs. pMDI's are comprised of a pressurized propellant canister with a metering valve housed in a molded actuator body with integral mouthpiece. This type of inhalation device presents drug delivery challenges to patients, requiring significant force to actuate with inhalation and timing coordination to effectively receive the drug. pMDI's containing suspended drug formulations also have to be shaken properly by the patient prior to actuating to receive an effective dose of the drug. These relatively complicated devices also require priming due to low drug content in initial doses and can require cleaning by the patient. In some devices, an additional spacer apparatus is prescribed along with the pMDI to compensate for the timing coordination issue, thus creating additional complications related to the patient for, cleaning, storage and transport of the bulky spacer apparatus. While many patients are experienced operating pMDI's or pMDI's with spacers, new patients often experience a relatively significant learning curve to operate these devices properly.

Dry powder inhalation devices (DPI) are also well-known for delivering powderized drugs to the lungs. DPI technologies are either active involving external energy to break-up and aerosolize particles or, passive utilizing the patient's inspiratory energy to entrain and deliver the powder to the lungs. Some DPI technologies integrate electronics while others are fully mechanical. The powder drug storage formats are normally reservoir, individually pre-metered doses, or capsule based systems. Some known DPI devices include (or deliver) engineered drug particles, but in most known devices deliver a conventional blend of sized active pharmaceutical ingredient(s) (API) plus sized lactose monohydrate used as a bulking agent to aid in the powder filling process and as carrier particles to aid in delivery of the active pharmaceutical ingredient(s) to the patient. These API—lactose monohydrate blends among others require a means to break-up aggregates formed by attractive forces holding them together.

Some known devices for storing and delivering known dry powder formulations include a storage reservoir and a separate chamber within which the dry powder can be disaggregated in preparation for delivery to the patient. Such known systems, however, often include multiple pathways (e.g., from the reservoir to the preparation chamber), and thus can have diminished accuracy of the delivered dose due to undesired contact with pathway walls, inconsistency in withdrawing the dose from the reservoir, and the like.

Some known devices for storing and delivering known dry powder formulations rely, at least in part, on air flow produced by the patient inspiration (i.e., inhalation). Variation in the flow rates and velocities produced among the patient population, however, can cause variation in the delivered dose and/or fine particle fraction. Moreover, normal part-to-part variation, as well as variation caused during use (e.g., deformation or blocking of flow paths due to the patient gripping the device) can also lead to undesired variation in the airflow resistance and accuracy of the delivered dose, as well as the magnitude of fine particle fraction.

Additionally, some known dry powder delivery devices are susceptible to inconsistent performance resulting from variations in how different users interact with the device. Said another way, known dry powder delivery devices do not account for "human factors" in operation. For example, known dry powder delivery devices can be susceptible to variations in performance based on any one or all the following: tilting of the device (before or during use), failure to generate adequate flow and pressure drop (vacuum or negative pressure), failure by the user to actuate mechanisms completely and properly (and in the correct order), and failure to load drug cartridges, capsules or blisters properly. As one example, some known dry powder delivery devices include passageways that can be obstructed if a user inadvertently covers an inlet port or squeezes the body of the device with too much force.

Thus, a need exists for improved methods and devices for delivering dry powder drugs. Specifically, a need exists for a dry powder delivery device having improved accuracy, improved fine particle fraction, and ease of use and administration. A need also exists for improved methods of filling and assembling dry powder delivery devices.

SUMMARY

Medicament delivery devices, drug products and methods for administration of dry powder medicaments are described herein. In some embodiments, an apparatus includes a first member and a second member coupled to the first member. The first member defines at least a portion of a disaggregation chamber containing a dry powder and includes a chamber wall that forms an outer boundary of the disaggregation chamber. The second member includes a surface covering the disaggregation chamber and defines an intake channel and an exit channel. The exit channel is configured to be fluidically coupled to the disaggregation chamber via an exit opening defined by the surface of the second member. The intake channel is configured to be fluidically coupled to the disaggregation chamber via an intake port. A center line of a portion of the intake channel is tangential to a portion of the chamber wall of the first member such that a portion of an inlet airflow conveyed into the disaggregation chamber via the intake channel has a rotational motion about a center axis of the disaggregation chamber. The intake port is defined at least in part by an intake ramp. The intake ramp includes a transition surface that forms an exit angle with respect to the surface of less than 105 degrees.

In some embodiments, an apparatus includes a lower member and an upper member coupled to the lower member. The lower member defines at least a lower portion of a disaggregation chamber containing a dry powder. The lower member includes a raised surface along a center axis of the disaggregation chamber. The upper member includes a surface that encloses the disaggregation chamber and defines an upper portion of the disaggregation chamber, the upper member defines an intake channel and an exit channel. The intake channel is fluidically coupled to the disaggregation chamber via an intake opening, and the exit channel is fluidically coupled to the disaggregation chamber via an exit opening defined by the surface of the upper member. The exit opening is along the center axis. The upper member includes a protrusion extending from the surface, the protrusion in contact with the raised surface to maintain a distance between the raised surface and the exit opening.

BRIEF DESCRIPTION OF THE DRAWINGS

FIG. 11 is a top view of the medicament delivery device shown in FIGS. 9 and 10, in an opened configuration.

FIG. 12 is a cross-sectional view of the medicament delivery device shown in FIG. 11 taken along line A1-A1.

FIGS. 26B and 26C are cross-sectional views of the medicament delivery device shown in FIG. 26A taken along line A1-A1 (FIG. 26B) and A2-A2 (FIG. 26C).

FIG. 30 is a flow chart of a method of delivering a medicament, according to an embodiment.

FIG. 43 is a top view of a portion of a medicament delivery device, according to an embodiment.

DETAILED DESCRIPTION

Figure 1:
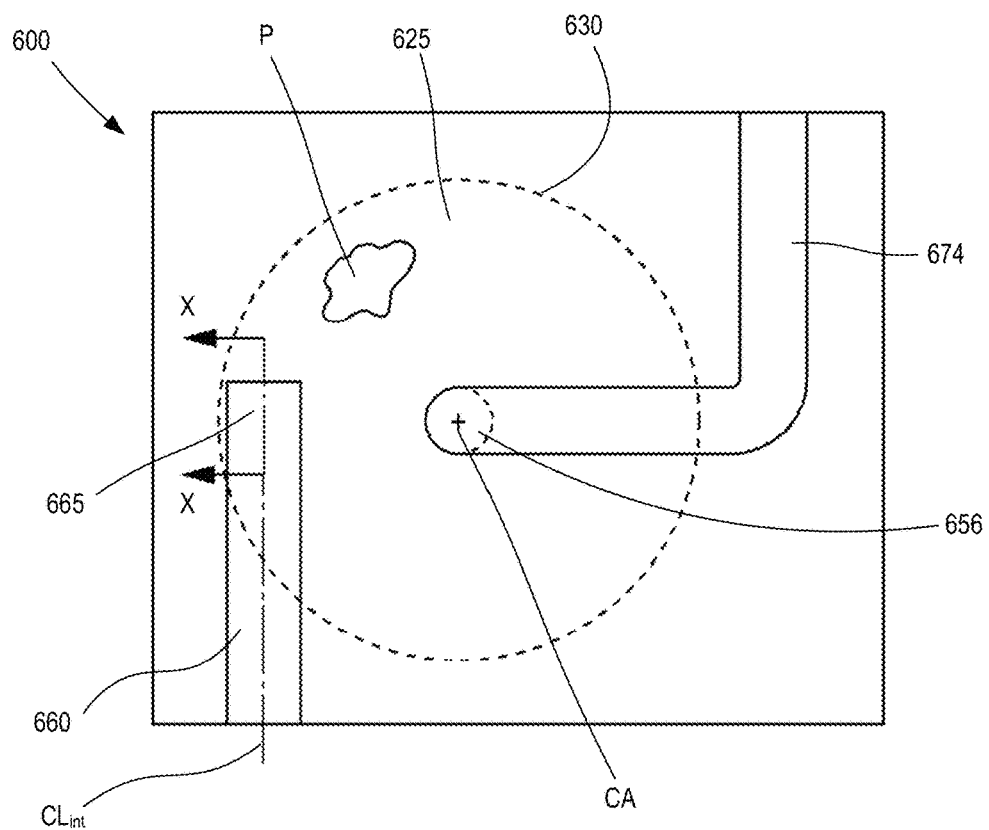
FIGS. 1 and 2 are schematic illustrations of a medicament delivery device, according to an embodiment, in various stages of operation.

Medicament delivery devices, drug products, and methods for administration of dry powder medicaments are described herein. In some embodiments, an apparatus includes a first member and a second member coupled to the first member. The first member defines at least a portion of a disaggregation chamber containing a dry powder and includes a chamber wall that forms an outer boundary of the disaggregation chamber. The second member includes a surface covering the disaggregation chamber and defines an intake channel and an exit channel. The exit channel is configured to be fluidically coupled to the disaggregation chamber via an exit opening defined by the surface of the second member. The intake channel is configured to be fluidically coupled to the disaggregation chamber via an intake port. A center line of a portion of the intake channel is tangential to a portion of the chamber wall of the first member such that a portion of an inlet airflow conveyed into the disaggregation chamber via the intake channel has a rotational motion about a center axis of the disaggregation chamber. The center line can be tangential in one plane (e.g., a top view) and non-tangential in other planes (e.g., a side view). The intake port is defined at least in part by an intake ramp. The intake ramp includes a transition surface that forms an exit angle with respect to the surface of less than 105 degrees.

Similarly stated, the transition surface is such that a second portion of the inlet airflow enters the disaggregation chamber at a flow angle of at least about 75 degrees (measured along the center line of the portion of the intake channel). In some embodiments, the transition surface is parallel to the center axis of the disaggregation chamber (or is normal to the surface of the second member). The structure of the transition surface advantageously produces a sudden expansion into the disaggregation chamber, which causes the second portion of the inlet airflow to recirculate or "fan out" in one or more directions that are not tangential to the chamber wall. This arrangement produces improved disaggregation and/or clearance of the dry powder and mixing of the particles within the airflow.

In some embodiments, the apparatus can further include a strip between the first member and the second member that retains the dry powder within the portion of the disaggregation chamber. In this manner, the disaggregation chamber can function both as a storage chamber and a disaggregation chamber that ensures the desired delivery characteristics of the powder stored therein. The strip fluidically isolates the portion of the disaggregation chamber from the intake channel and the exit channel when the strip is in a first position. The strip is configured to be moved relative to the first member to a second position to place the portion of the disaggregation chamber in fluid communication with the intake channel and the exit channel.

In some embodiments, an apparatus includes a first member and a second member coupled to the first member. The first member defines at least a portion of a disaggregation chamber containing a dry powder and includes a chamber wall that forms an outer boundary of the disaggregation chamber. The second member includes a surface covering the disaggregation chamber and defines an intake channel and an exit channel. The exit channel is fluidically coupled to the disaggregation chamber via an exit opening defined by the surface of the second member. The intake channel is configured to be fluidically coupled to the disaggregation chamber via an intake port. A center line of the intake channel is tangential to a portion of the chamber wall of the first member such that a first portion of an inlet airflow conveyed into the disaggregation chamber via the intake channel has a rotational motion about the exit opening. The center line can be tangential in one plane (e.g., a top view) and non-tangential in other planes (e.g., a side view). The intake port defined at least in part by an intake ramp that is ramp curved outwardly towards the chamber wall such that a second portion of the inlet airflow conveyed into the disaggregation via the intake channel is conveyed towards the chamber wall.

In some embodiments, the first member and the second member can be monolithically constructed.

In some embodiments, the intake ramp defines a first radius of curvature within a first plane normal to a center axis and a second radius of curvature within a second plane normal to the first plane. The first radius of curvature and the second radius of curvature each open outwardly towards the chamber wall. This arrangement causes a portion of the flow entering the disaggregation chamber (i.e., the second portion) to cross the path of the rotational flow within the disaggregation chamber (i.e., the first portion). This produces disruption of the rotational flow and dispersion of particles circulating in the rotational flow stream toward the outlet hole. Thus, this arrangement produces reduced dose release time and higher emitted dose percentage.

In some embodiments, an apparatus includes a first member and a second member coupled to the first member. The first member defines at least a portion of a disaggregation chamber containing a dry powder and includes a chamber wall that forms a boundary of the disaggregation chamber. The second member includes an inner surface and an outer surface and defines an intake channel and an exit channel. The inner surface covers the disaggregation chamber. The exit channel is fluidically coupled to the disaggregation chamber via an exit opening defined by the inner surface of the second member. The intake channel is fluidically coupled to the disaggregation chamber via an intake port. The intake channel fluidically coupled to an external volume outside of the disaggregation chamber by an external opening defined by the outer surface. The outer surface includes one or more barrier surfaces at least partially surrounding the external opening and that are configured to limit obstruction of the external opening.

In some embodiments, the barrier surfaces are formed from a set of protrusions extending from the outer surface of the second member. In some embodiments, the barrier surfaces are non-planar surface (or collectively form a set of non-planar surfaces). This arrangement can reduce the likelihood that a user's finger or other object will obstruct the external opening.

In some embodiments, an apparatus includes a lower member and an upper member coupled to the lower member. The lower member defines at least a lower portion of a disaggregation chamber containing a dry powder. The lower member includes a raised surface along a center axis of the disaggregation chamber. The upper member includes a surface that encloses the disaggregation chamber and defines an upper portion of the disaggregation chamber, the upper member defines an intake channel and an exit channel. The intake channel is fluidically coupled to the disaggregation chamber via an intake opening, and the exit channel is fluidically coupled to the disaggregation chamber via an exit opening defined by the surface of the upper member. The exit opening is along the center axis. The upper member includes a protrusion extending from the surface, the protrusion in contact with the raised surface to maintain a distance between the raised surface and the exit opening.

In some embodiments, an apparatus includes an upper portion and a lower portion that collectively define a disaggregation chamber. At least one of the upper or lower portion can include flow structures, such as vanes, ramps, or protrusions that produce a flow pattern to repeatably disaggregate a dry powder by controlling powder release timing and swirl time duration of the dry powder stored within the disaggregation chamber.

In some embodiments, an apparatus includes a lower member and an upper member coupled to the lower member. The lower member defines at least a lower portion of a disaggregation chamber containing a dry powder. The lower member includes a raised surface along a center axis of the disaggregation chamber. The upper member includes a surface that encloses the disaggregation chamber and defines an upper portion of the disaggregation chamber, the upper member defines an intake channel and an exit channel. The intake channel is fluidically coupled to the disaggregation chamber via an intake opening, and the exit channel is fluidically coupled to the disaggregation chamber via an exit opening defined by the surface of the upper member. The lower member and the upper member are collectively configured to deliver a dose of the dry powder independent of an orientation of the lower member and the upper member. For example, in some embodiments, the exit opening is opposite from the raised surface, thus the dose of dry powder is delivered via an annular opening between the raised surface of the lower member and the surface of the upper member. The annular opening (or gap) can prevent powder from remaining on the surface of the upper member if the apparatus is turned upside down. The intake channel also limits the likelihood that the powder will exit (or be spilled) backwards out of the dose chamber by including a series of bends (or a tortuous path).

In some embodiments, a method includes delivering a dose of dry powder from a unit-dose dry powder drug product during patient inspiration. The method includes removing a safety tab and placing an exit opening within a mouth. An airflow is then produced by inspiration, the inspiration occurring for an inspiration time period during which between about 2 liters and 4 liters of air are drawn through the device. In some embodiments, the inspiration time period is at least about four seconds. In response to the airflow, the dry powder is disaggregated within a chamber and delivered via the exit opening. In some embodiments, the dry powder is disaggregated within the chamber for a disaggregation time period of at least about two seconds.

In some embodiments, a method includes moving a strip from a first position between a first member of a dry powder inhaler and a second member of the dry powder inhaler to a second position. The strip seals a dry powder within a portion of a disaggregation chamber defined by a chamber wall of the first member when the strip is in the first position. The portion of the disaggregation chamber is in fluid communication with an exit channel defined by the second member and an intake channel defined by the second member when the strip is in the second position. A mouthpiece of the dry powder inhaler is placed into a mouth. The method further includes inhaling into the mouth to draw an inlet airflow through the intake channel and into the disaggregation chamber. A portion of the intake channel is tangential to a portion of the chamber wall of the first member such that a portion of an inlet airflow has a rotational motion within the disaggregation chamber. The portion of the intake channel can be tangential in one plane (e.g., a top view) and non-tangential in other planes (e.g., a side view). The rotational motion disaggregates the dry powder to produce a plurality of respirable particles within the inlet airflow. The intake channel and the exit channel collectively configured to produce an exit airflow containing the plurality of respirable particles for at least two seconds.

In some embodiments, a kit includes a package containing a dry powder inhaler and an applicator. The dry powder inhaler is configured to deliver a single dose of a dry powder medicament. The applicator is configured to be removably coupled to the dry powder inhaler and allows a caregiver to position the dry powder inhaler for a user without touching the patient or the dry powder inhaler. In this manner, the applicator facilitates maintaining sterility during drug delivery, as well as protecting the caregiver (or administrator) from contamination.

Methods of assembling a medical device are described herein. In some embodiments, a method includes conveying a dry powder into a portion of a disaggregation chamber defined by a first member of a medical device. A strip is coupled to an inner surface of the first member to seal the dry powder within the portion of the disaggregation chamber. A second member of the medical device is placed in contact with the first member such that an inner surface of the second member covers the portion of the disaggregation chamber. The second member defines an intake channel and an exit channel. The exit channel is configured to be fluidically coupled to the disaggregation chamber via an exit opening defined by the inner surface of the second member. The intake channel configured to be fluidically coupled to the disaggregation chamber via an intake port. A flange extending from the inner surface of the first member is deformed to be matingly coupled to a joint surface of the second member to form a sealed joint between the first member and the second member.

In some embodiments, the flange is deformed by heat staking or heat swaging the flange to bend the flange against the joint surface. Such methods of assembly can limit potential adverse effects on the powder that may results from high temperatures or other methods of joining (e.g., ultrasonic welding, radio frequency welding, or the like). Such methods are also easy to implement, thereby reducing the cost and complexity of producing the medical device. Heat-swaging the flange can produce a more air-tight (or hermetic) seal than certain other joining methods, such as press fits, etc.

In some embodiments, the first member and the second member are monolithically constructed from a degradable material, such as, for example, a degradable material that is biodegradable, degradable via exposure to ultraviolet radiation, or degradable, fragmentable, compostable via exposure to any combination of ultraviolet light radiation, oxygen, moisture and biological organisms.

In some embodiments, any of the devices, dry powder inhalers, or methods can contain a dry powder that includes a bronchodilator, such as any of albuterol sulfate, levalbuterol, ipratropium, albuterol/ipratropium, pirbuterol, or fenoterol.

As used herein, the words "proximal" and "distal" refer to direction closer to and away from, respectively, a location of administration to a patient. Thus, for example, the end of the medicament delivery device contacting the patient's body for delivery (e.g., the mouth) would be the distal end of the medicament delivery device, while the end opposite the distal end would be the proximal end of the medicament delivery device. It is contemplated that any of the devices described herein can be administered or actuated by either the patient themselves (i.e., self-administration) or a caregiver (e.g., an operator, medical professional, or other administrator).

As used herein, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly.

The term "about" when used in connection with a referenced numeric indication means the referenced numeric indication plus or minus up to 10 percent of that referenced numeric indication. For example, "about 100" means from 90 to 110.

The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a mass that is "substantially 90 micrograms (mcg)" is intended to convey that, while the recited volume is desirable, some tolerances can occur when the volume is "substantially" the recited mass (e.g., 90 mcg). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 10 kPa. Any residual fluid layer that may be present on a portion of a wall of a container after component defining a "substantially-fluid tight" seal are moved past the portion of the wall are not considered as leakage.

Figure 2:
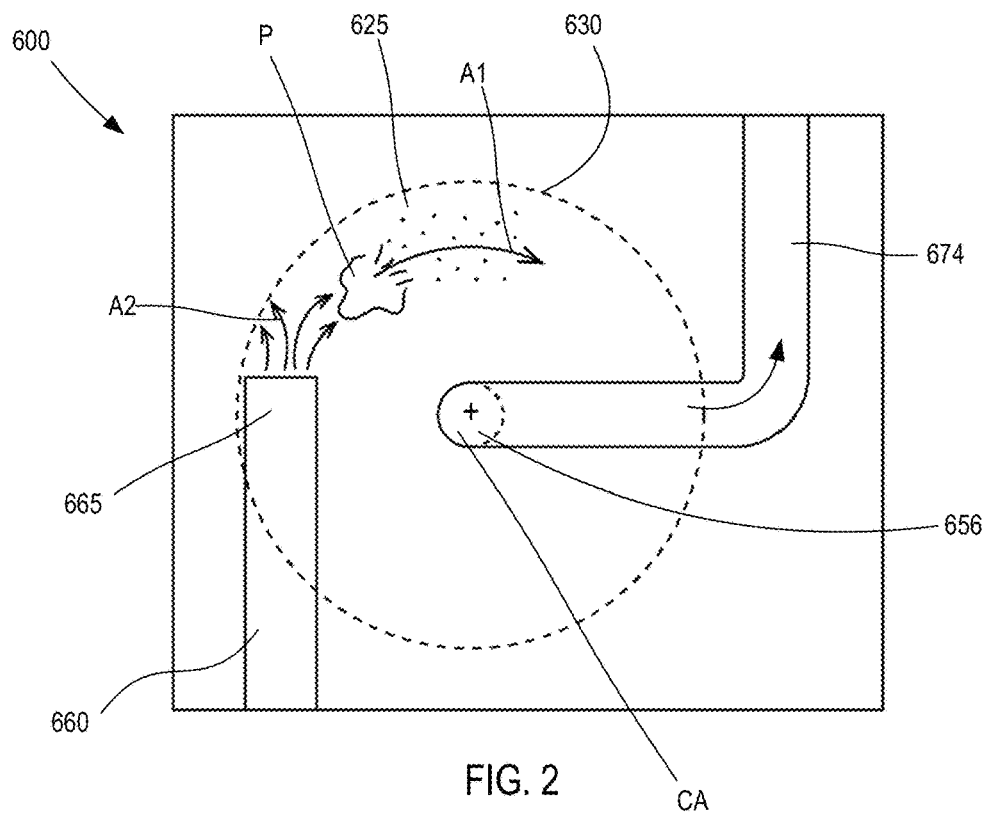

In some embodiments, a drug product configured for administration by an untrained or partially-trained user (such as self-administration by a user) can include any of the medicament compositions described herein. Such drug products can include, for example, a dry powder delivery device configured to provide repeatable (e.g., device-to-device) and accurate dose delivery. One example of such a medicament delivery device is provided in FIGS. 1-3, which are schematic illustrations of a medicament delivery device (or drug product) 600 according to an embodiment. The medicament delivery device 600 includes a first member (or portion) 620 and a second member (or portion) 650 coupled to the first member 620. The first member 620 defines at least a portion of a disaggregation chamber 625 (also referred to as a dose chamber) that contains a dry powder P. More particularly, the first member 620 includes a chamber wall 630 (shown as a dashed line in FIGS. 1 and 2) that forms an outer boundary of the disaggregation chamber 625. The chamber wall 630 is curved and defines a center axis CA. As described below, in use, a portion of an inlet air flow can flow in a rotational (or swirling manner) within the chamber 625, bounded by the chamber wall 630, as shown by the arrow A1. The chamber 625 can be configured such that, as the dry powder P is disaggregated into particles (shown in FIG. 2) within the desired size range, the particles are entrained in the airflow and exit the chamber 625 via an exit opening 656 that is defined by the second member 650. Although the chamber wall 630 is shown as being circular, in other embodiments, the chamber wall 630 (and any of the chambers described herein) can have any suitable shape. For example, in some embodiments, the chamber wall 630 can be oval, elliptical, polygonal, or spiral shaped.

The second member 650 includes an inner surface 651 (see FIG. 3) that covers the disaggregation chamber 625. The inner surface 651 can be coupled to a corresponding inner surface of the first member 620 by any suitable mechanism described herein. The slight gap shown in FIG. 3 between the first member 620 and the second member 650 is only for purposes of illustration to more clearly identify the inner surface 651. In reality, the first member 620 is coupled to the second member 650 in a manner that prevents air leakage from the interface between the first member 620 and the second member 650. The second member 650 defines an intake channel 660 and an exit channel 674. The exit channel 674 is configured to be fluidically coupled to the disaggregation chamber 625 via an exit opening 656 defined by the surface 651 of the second member 650. In this manner, when a user inhales on the exit channel 674, inlet air can be drawn from the disaggregation chamber 625 through the exit opening 656 and into the exit passageway 674 to deliver a dose of the dry powder P to the user.

As viewed from the top (FIGS. 1 and 2), the intake channel 660 defines a center line CL that is tangential to a portion of the chamber wall 630 of the first member 620 such that a first portion of an inlet airflow (shown as arrow A3 in FIG. 3) conveyed into the disaggregation chamber 625 via the intake channel 660 initiates a rotational flow A1 and particle motion about the center axis CA of the disaggregation chamber 625. Similarly stated, at least a portion of the intake channel 660 is shaped and positioned with respect to the disaggregation chamber 625 such that the linear momentum of the first portion of the inlet airflow within the intake channel 660 is transformed into an angular momentum within the disaggregation chamber 625 (about the center axis CA). In this manner, the intake channel 660 produces a rotational (or swirling) airflow with disruption at air inlet location(s) within the disaggregation chamber 625. In some embodiments, the center line CL can be tangential in one plane (e.g., a top view, FIG. 1) and non-tangential in other planes (e.g., a side view, FIG. 3). In other embodiments, the center line CL need not be tangential to a portion of the chamber wall 630.

Figure 3:
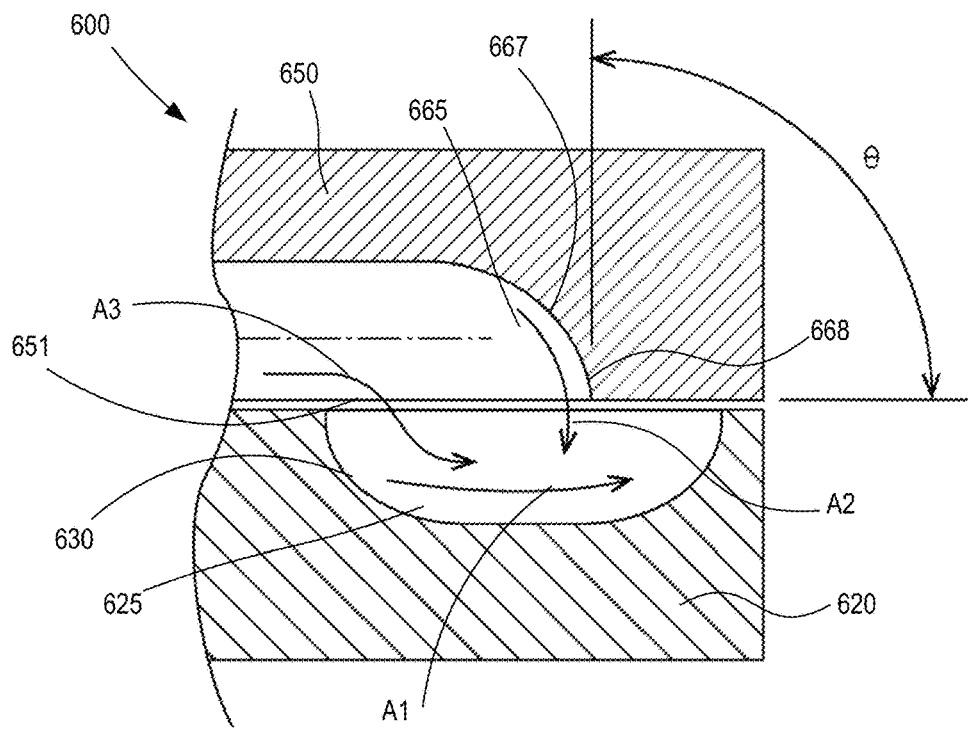
FIG. 3 is a cross-section view of a portion of the medicament delivery device shown in FIG. 1 taken along line X-X.

The intake channel 660 is configured to be fluidically coupled to the disaggregation chamber 625 via an intake port 665. As described herein, the characteristics of the inlet air flow as it enters the disaggregation chamber 625 can impact the accuracy and repeatability with which the dry powder P is disaggregated, broken up, and/or otherwise prepared for delivery to the user. For example, in addition to the dose chamber 625 shape and dimensions (e.g. depth and diameter), the shape and size of the inlet passageways can influence the airflow pattern within the chamber 625 (see, e.g., the arrow A1 in FIG. 2). Referring to FIG. 3, the intake port 665 is defined at least in part by an intake ramp 667 that includes a transition surface 668. The transition surface 668 intersects the inner surface 651 to form an edge or interrupted edge of the second member 650. As shown in FIG. 3, the transition surface 668 forms an exit angle Θ with respect to the surface 651. The exit angle Θ can impact the dose release timing by controlling the number of revolutions that entrained particles make within the chamber 625 before exiting, the efficiency of disaggregation, the percentage of the dose emitted, and the like. Thus, the intake port 665 and the transition surface 668 are configured to produce the desired inlet airflow into the disaggregation chamber 625 such that the desired exit characteristics (e.g., dose release timing, particle size distribution, percentage of dose emitted) are achieved. For example, in some embodiments, the drug product 600 (or any other drug products described herein) can produce a particle size distribution well suited for reaching the deeper areas (e.g., alveoli) of the lungs.

In some embodiments, the exit angle Θ is less than 105 degrees. Similarly stated, the transition surface 668 is angled such that a second portion of the inlet airflow A2 enters the disaggregation chamber at a flow angle of at least about 75 degrees (measured along the center line CL of the intake channel 660). In some embodiments, the transition surface is parallel to the center axis CA of the disaggregation chamber 625 (i.e., the exit angle Θ is about 90 degrees). By having an exit angle Θ of less 105 degrees (or at about 90 degrees), the transition surface 668 advantageously produces a sudden expansion into the disaggregation chamber 625 (as opposed to a more gradual diffusion into the disaggregation chamber 625). This arrangement produces disruption of rotational air flow A1 when a portion of intake flow A2 is conveyed from the intake channel 660 to the disaggregation chamber 625. In some embodiments, the intake air flow generated by the intake channel 660 and transition to the disaggregation chamber 625 can produce a rotational flow component A3 in FIG. 3 as well as a disruptive flow component as indicated by A2 in FIG. 3, or can otherwise cause the second portion A2 of the inlet airflow to disrupt rotational flow A1 (shown in FIG. 2) and "fan out" the rotational air-particle stream in one or more directions that are not tangential to the chamber wall 630. This non-tangential flow direction is shown by the arrows A2 in FIG. 2, and is similar to the flow structure and concepts described within reference to the device 100 shown in FIG. 29. This arrangement of disrupted rotational flow enables particles to more easily flow to the exit opening 656 of the disaggregation chamber 625, reduces dose release timing, and provides a higher emitted dose percentage. In some embodiments, the edge between the transition surface 668 and the inner surface 651 can be a substantially sharp edge (e.g., have an edge radius of less than about 130 microns (0.005 inches)). This can further enhance flow separation or "fan out" of the second portion of the inlet airflow A2 as air is conveyed through the intake port 665 and into the disaggregation chamber. In other embodiments, however, the edge between the transition surface 668 and the inner surface 651 can be curved or have a radius of greater than about 130 microns (i.e., can include an edge break).

The dry powder P included in the medicament delivery device 600 (or any of the devices described herein) can include any suitable medicament, nutraceutical, or composition. In some embodiments, any of the medicament delivery devices (or drug products) described herein can include a composition including any suitable active pharmaceutical ingredient (API), any suitable excipient, bulking agent, carrier particle, or the like.

In some embodiments, the API can include albuterol sulfate (also referred to as "sulphate," for example, in Europe). In other embodiments, any of the drug products described herein can include any other bronchodilator. For example, in some embodiments the API can include a short-acting bronchodilator, such as, for example, levalbuterol, ipratropium, albuterol/ipratropium, pirbuterol, and/or fenoterol. For example, in some embodiments the API can include a long-acting bronchodilator, such as, for example, aclidinium (Tudorza), arformoterol (Brovana), formoterol (Foradil, Perforomist), glycopyrrolate (SeebriNeohaler), indacaterol (Arcapta), olodaterol (Striverdi Respimat), salmeterol (Serevent), tiotropium bromide (Spiriva), umeclidinium (IncruseEllipta), mometasone furoate powder, flunisolide, budesonide, and/or vilanterol.

As described herein, the dry powder P can also include any suitable excipient, such as, for example, lactose. The dry powder P can often include predominantly the excipient with a small percentage of the mass being the API (e.g., one to ten percent). Thus, the delivery characteristics of the device 600 can be highly dependent on the lactose characteristics (or the grade of lactose included within the dry powder P). For example, some dry powder P can include a non-sieved lactose with a mean diameter of 60 microns. Such powder formulations therefore include the fine lactose particles (e.g., 1-5 microns), and thus can be more "sticky" than those formulations that do not include as much of the fine particles. The advantage of using such non-sieved lactose is that a higher percentage of fine particles can be delivered, which can be beneficial for the desired treatment (e.g., deep lung delivery or the like). Such non-sieved formulations, however, can require more turbulent airflow to disaggregate the stickier fine particles than is needed for a sieved formulation. Thus, the transition surface 668 and the exit angle Θ can be optimized for use with (and can provide the desired amount of disruptive airflow) for a non-sieved formulation. Thus, in some embodiments, the dry powder P can include a non-sieved lactose formulation having a mean particle diameter of 60 microns. In other embodiments, the dry powder P can include a sieved lactose formulation having an initial mean particle diameter of 60 microns, but with a substantial amount of the fine particles removed by the sieve operation.

In some embodiments, the medicament delivery device 600 can include a strip or seal (not shown) that fluidically isolates the portion of the disaggregation chamber 625 from the intake channel 660 and/or the exit channel 674. In this manner, the disaggregation chamber 625 functions as a chamber (or a portion of a chamber) within which the dry powder can be both stored and later disaggregated. The strip (or seal) can be any suitable seal shown and described herein (e.g., the strip 110 of the device 100 shown below), or can be similar to the partition 95 shown and described in U.S. Pat. No. 9,446,209 (filed Mar. 7, 2014), entitled "Dry Powder Inhalation Device," which is incorporated herein by reference in its entirety. For example, in some embodiments, a strip can be coupled between the first member 620 and the second member 650 (e.g., in contact with the inner surface 651) to seal and/or maintain the dry powder P within the chamber 625. Any such seal member can be formulated to be compatible with any of the medicaments and/or drug compositions disposed within the chamber 625. Similarly stated, the seal member can be formulated to minimize any reduction in the efficacy of the drug compositions that may result from contact (either direct or indirect) between the seal member and the drug composition within the chamber 625. For example, in some embodiments, the seal member can be formulated to minimize any leaching or out-gassing of compositions that may have an undesired effect on the drug composition within the device 600. In other embodiments, the seal member can be formulated to maintain its chemical stability, flexibility, strength, and/or sealing properties when in contact (either direct or indirect) with the drug composition within the device 600 over a long period of time (e.g., for up to six months, one year, two years, five years, or longer).

In use, the user first removes any packaging or overwrap (not shown in FIGS. 1-3, see the overwrap 711 described below) from about the device 600. The user can then optionally remove any seal from between the first member 620 and the second member 650. The user then places a portion of the device (e.g., a mouthpiece) into or against their mouth. The user then inhales, which draws air through the intake channel 660 and into the disaggregation chamber 625. As described above, the inlet airflow is drawn through the inlet port 665, which imparts the desired flow characteristics to the inlet airflow as it enters the chamber 625. The inlet airflow moves within the chamber 625 (see, e.g., the arrows A1 and A2 in FIG. 2) and entrains the dry powder P stored therein. Continued dynamic motion of the inlet airflow causes disaggregation of the particles, thus producing the desired drug delivery performance characteristics (e.g., emitted dose, fine particle mass) for delivery to the patient via the exit channel 674.

The medicament delivery device 600 (and any of the medicament delivery devices described herein) can be constructed from any suitable materials and can be assembled according to any of the methods described herein. For example, in some embodiments, the first member 620 and the second member 650 are monolithically constructed from a polymeric material. In some embodiments, the material can be a degradable material, such as, for example, a degradable material that is biodegradable, degradable via exposure to ultraviolet radiation, or degradable, fragmentable, compostable via exposure to any combination of ultraviolet light radiation, oxygen, moisture and biological organisms.

Although the intake ramp 667 of the intake port 665 described above is shown as having a curved surface in one plane, in other embodiments, a medicament delivery device can include an intake port having any suitable curved structure to facilitate production of the desired flow. Similarly stated, although the intake ramp 667 is shown as being rectangular shaped when viewed in a first plane normal to the center axis CA (e.g., the top view of FIGS. 1 and 2) and curved in a second plane parallel to the center axis CA (e.g., the side view of FIG. 3), in other embodiments, an intake port can include curved surfaces in any plane (or planes). For example, FIGS. 4-7 are schematic illustrations of a medicament delivery device (or drug product) 700 according to an embodiment. The medicament delivery device 700 includes a first member (or portion) 720 and a second member (or portion) 750 coupled to the first member 720. The first member 720 defines at least a portion of a disaggregation chamber 725 that contains a dry powder P. More particularly, the first member 720 includes a chamber wall 730 (shown as a dashed line in FIGS. 4, 5, and 7) that forms an outer boundary of the disaggregation chamber 725. The chamber wall 730 is curved and defines a center axis CA. As described below, in use, a portion of an inlet air flow can flow in a rotational (or swirling manner) within the chamber 725, bounded by the chamber wall 730, as shown by the arrow A1. The chamber 725 can be configured such that, as the dry powder P is disaggregated into particles (identified as particles P1 and P2 in FIGS. 5 and 7) within the desired size range, the particles are entrained in the airflow and exit the chamber 725 via an exit opening 756 that is defined by the second member 750. Although the chamber wall 730 is shown as being circular, in other embodiments, the chamber wall 730 (and any of the chambers described herein) can have any suitable shape. For example, in some embodiments, the chamber wall 730 can be oval, elliptical, polygonal, or spiral shaped.

The second member 750 includes an inner surface 751 (see FIG. 6) that covers the disaggregation chamber 725. The inner surface 751 can be coupled to a corresponding inner surface of the first member 720 by any suitable mechanism described herein. The slight gap shown in FIG. 3 between the first member 720 and the second member 750 is only for purposes of illustration to more clearly identify the inner surface 751. In reality, the first member 720 is coupled to the second member 750 in a manner that prevents air leakage from the interface between the first member 720 and the second member 750. The second member 750 defines an intake channel 760 and an exit channel 774. The exit channel 774 is configured to be fluidically coupled to the disaggregation chamber 725 via an exit opening 756 defined by the surface 751 of the second member 750. In this manner, when a user inhales on the exit channel 774, inlet air can be drawn from the disaggregation chamber 725 through the exit opening 756 and into the exit passageway 774 to deliver a dose of the dry powder P, and specifically the fine particles P2, to the user.

The intake channel 760 defines a center line CL that is tangential to a portion of the chamber wall 730 of the first member 720 such that a first portion of an inlet airflow (shown as arrow A1 in FIGS. 5 and 7) conveyed into the disaggregation chamber 725 via the intake channel 760 has a rotational motion about the center axis CA of the disaggregation chamber 725 and/or the exit opening 756. Similarly stated, at least a portion of the intake channel 760 is shaped and positioned with respect to the disaggregation chamber 725 such that the linear momentum of the first portion of the inlet airflow within the intake channel 760 is transformed into an angular momentum within the disaggregation chamber 725 (about the center axis CA). In this manner, the intake channel 760 produces a rotational (or swirling) airflow within the disaggregation chamber 725. In some embodiments, the center line CL can be tangential in one plane (e.g., a top view, FIG. 4) and non-tangential in other planes (e.g., a side view, FIG. 6). In other embodiments, the center line CL need not be tangential to a portion of the chamber wall 730.

Figure 6:
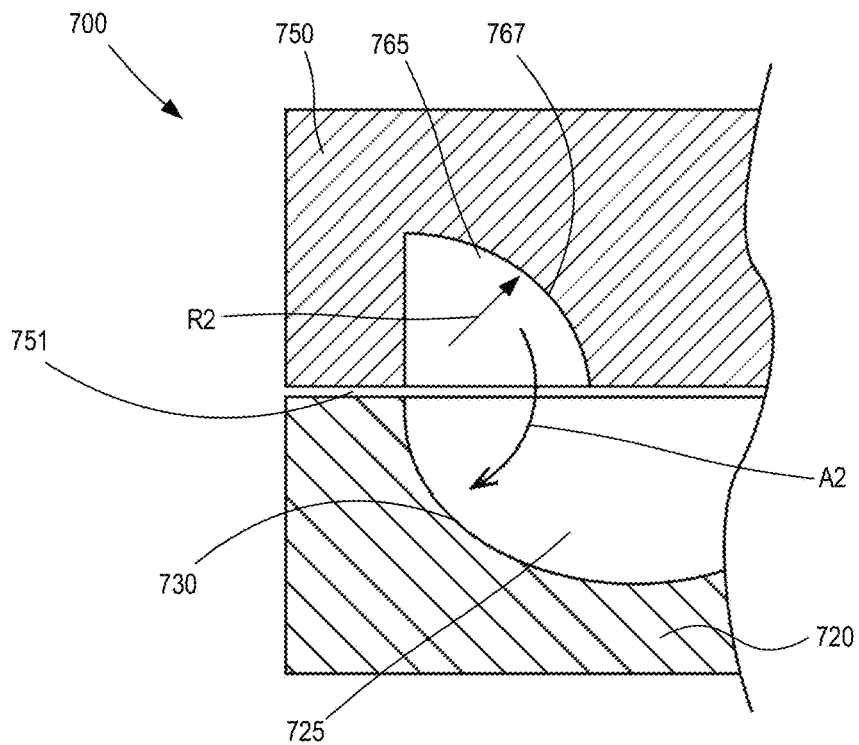
FIG. 6 is a cross-section view of a portion of the medicament delivery device shown in FIG. 4 taken along line X-X.
Figure 7:
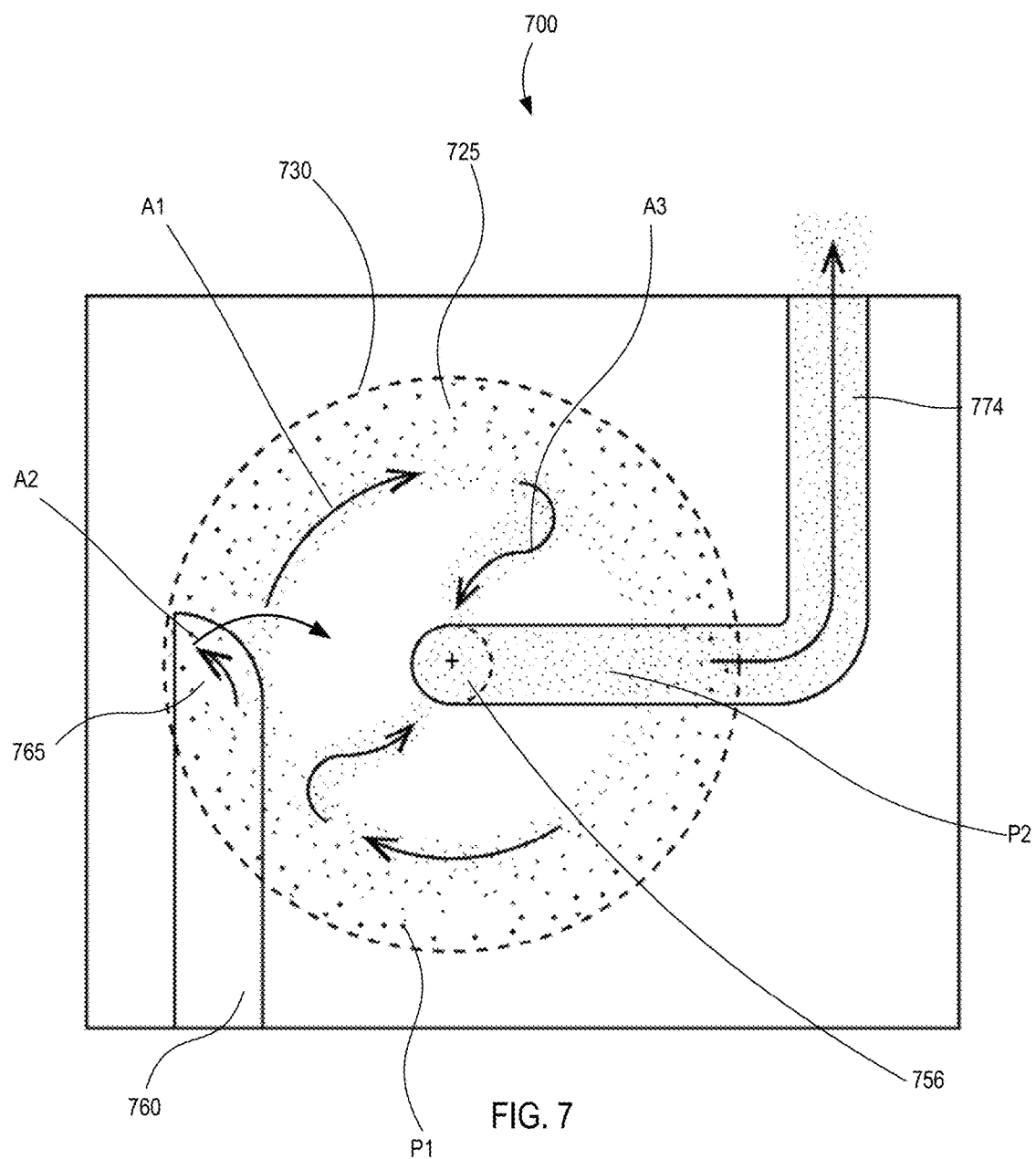

The intake channel 760 is configured to be fluidically coupled to the disaggregation chamber 725 via an intake port 765. As described herein, the characteristics of the inlet air flow as it enters the disaggregation chamber 725 can impact the accuracy and repeatability with which the dry powder P is disaggregated, broken up, and/or otherwise prepared for delivery to the user. Referring to FIG. 6, the intake port 765 is defined at least in part by an intake ramp 767 that is curved outwardly towards the chamber wall 730. This arrangement causes a second portion A2 of the inlet airflow to be conveyed outwardly towards the chamber wall 730 when conveyed from the intake channel 760 to the chamber 725. In this manner, the rotational flow within the disaggregation chamber 725 is biased towards and deflects off the outside portion of the disaggregation chamber 725, toward the exit opening 756. Similarly stated, the second portion of the airflow A2 can "bounce" off the outer portion of the wall 730 and be conveyed through the first portion of the airflow A1 and toward the exit opening 756. Thus, the particles circulating within the first portion A1 of the inlet airflow will flow through (and be disrupted by) the second portion A2 of the inlet airflow. Similarly stated, the different direction of airflow streams produces reduced dose release time and increased emitted dose percentage.

Additionally, by deflecting and biasing the rotational flow within the disaggregation chamber 725 toward the exit opening 756, the length of time during which a series of particles resides within the disaggregation chamber 725 is reduced. Similarly stated, deflecting and biasing the rotational flow within the disaggregation chamber 725 toward the exit opening 756 causes the effective clearance of large and/or cohesive powder doses from the disaggregation chamber 725.

Figure 4:
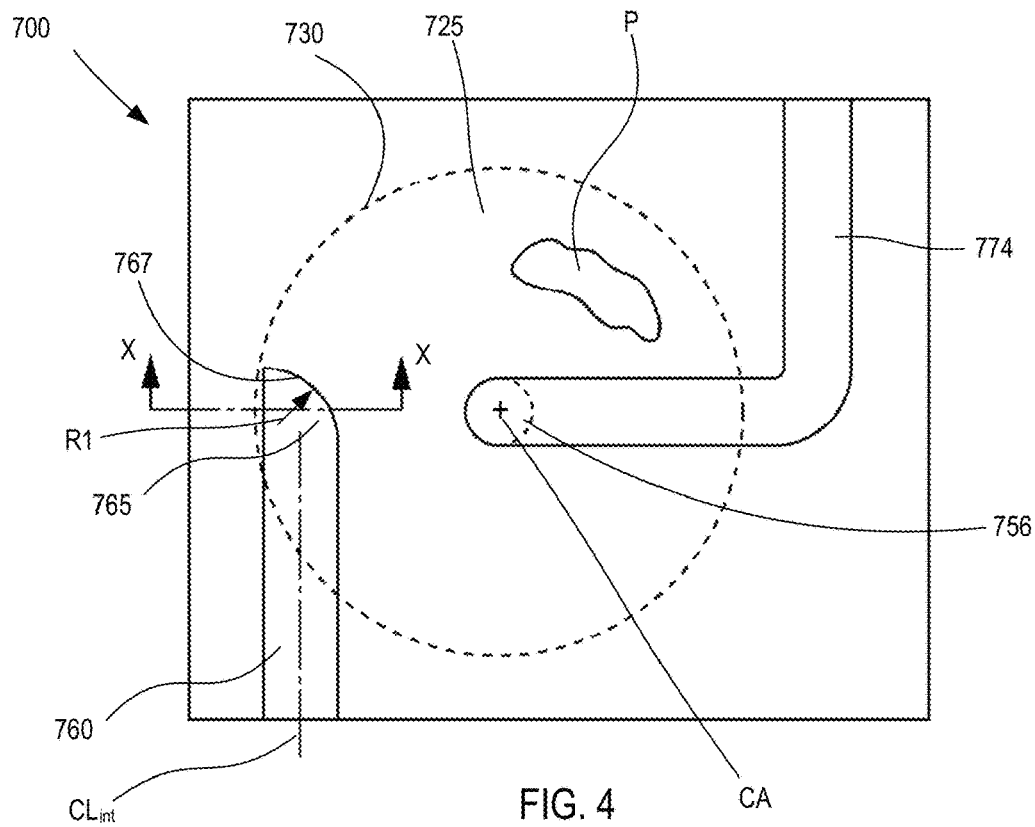
FIGS. 4, 5, and 7 are schematic illustrations of a medicament delivery device, according to an embodiment, in various stages of operation.
Figure 5:
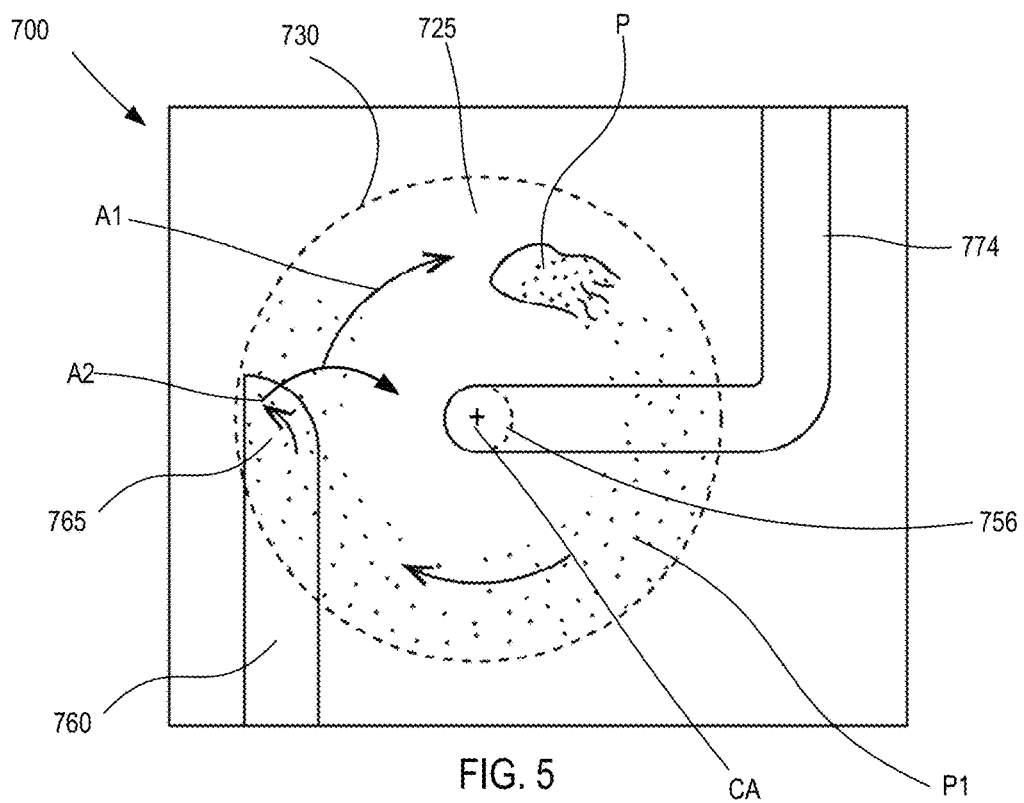

Referring to FIGS. 4 and 6, in some embodiments, the intake ramp 767 can be curved outwardly towards the chamber wall 730 in multiple planes. For example, the intake ramp 767 defines a first radius of curvature R1 within a first plane normal to the center axis CA (e.g., the top view of FIG. 4). The intake ramp 767 also defines a second radius of curvature R2 within a second plane parallel to the center axis CA (e.g., the side view of FIG. 6).

In some embodiments, the medicament delivery device 700 can include properties or characteristics of the medicament delivery device 600, and vice-versa. For example, in some embodiments, the intake ramp 767 can include a transition surface similar to the transition surface 668 shown and described above. For example, in some embodiments, the intake ramp 767 can include a transition surface that forms an exit angle of less than about 105 degrees. In some embodiments, the intake ramp 767 can include a transition surface that forms a substantially sharp edge (e.g., have an edge radius of less than about 130 microns) with the inner surface 751.

The dry powder P included in the medicament delivery device 700 (or any of the devices described herein) can include any suitable medicament, nutraceutical, or composition. In some embodiments, any of the medicament delivery devices (or drug products) described herein can include a composition including any suitable active pharmaceutical ingredient (API), any suitable excipient, bulking agent, carrier particle, or the like.

In some embodiments, the API can include albuterol sulfate. In other embodiments, any of the drug products described herein can include any other bronchodilator. For example, in some embodiments the API can include a short-acting bronchodilator, such as, for example, levalbuterol, ipratropium, albuterol/ipratropium, pirbuterol, and/or fenoterol. For example, in some embodiments the API can include a long-acting bronchodilator, such as, for example, aclidinium (Tudorza), arformoterol (Brovana), formoterol (Foradil, Perforomist), glycopyrrolate (SeebriNeohaler), indacaterol (Arcapta), olodaterol (Striverdi Respimat), salmeterol (Serevent), tiotropium bromide (Spiriva), umeclidinium (IncruseEllipta), mometasone furoate powder, flunisolide, budesonide, and/or vilanterol.

As described herein, the dry powder P can also include any suitable excipient, such as, for example, lactose. The dry powder P can often include predominantly the excipient with a small percentage of the mass being the API (e.g., one to ten percent). Thus, the delivery characteristics of the device 700 can be dependent on the lactose characteristics (or the grade of lactose included within the dry powder P). For example, some dry powder P can include a non-sieved lactose with a mean diameter of 60 microns. Such powder formulations therefore include the fine lactose particles (e.g., 1-5 microns), and thus can be more "sticky" than those formulations that do not include as much of the fine particles. The advantage of using such non-sieved lactose is that a higher percentage of fine particles can be delivered, which can be beneficial for the desired treatment (e.g., deep lung delivery or the like). Such non-sieved formulations, however, can require more turbulent airflow to disaggregate the stickier fine particles than is needed for a sieved formulation. Thus, the ramp 667 can be optimized for use with (and can provide the desired amount of disruptive airflow) for a non-sieved formulation. Thus, in some embodiments, the dry powder P can include a non-sieved lactose formulation having a mean particle diameter of 60 microns. In other embodiments, the dry powder P can include a sieved lactose formulation having an initial mean particle diameter of 60 microns, but with a substantial amount of the fine particles removed by the sieve operation.

In some embodiments, the medicament delivery device 700 can include a strip or seal (not shown) that fluidically isolates the portion of the disaggregation chamber 725 from the intake channel 760 and/or the exit channel 774. In this manner, the disaggregation chamber 725 functions as a chamber (or a portion of a chamber) within which the dry powder can be both stored and later disaggregated. The strip (or seal) can be any suitable seal shown and described herein (e.g., the strip 110 shown below), or can be similar to the partition 95 shown and described in U.S. Pat. No. 9,446,209 (filed Mar. 7, 2014), entitled "Dry Powder Inhalation Device," which is incorporated herein by reference in its entirety.

The medicament delivery device 700 can be used in a manner similar to that described above for the medicament delivery device 600, or any other methods described herein.

Figure 8:
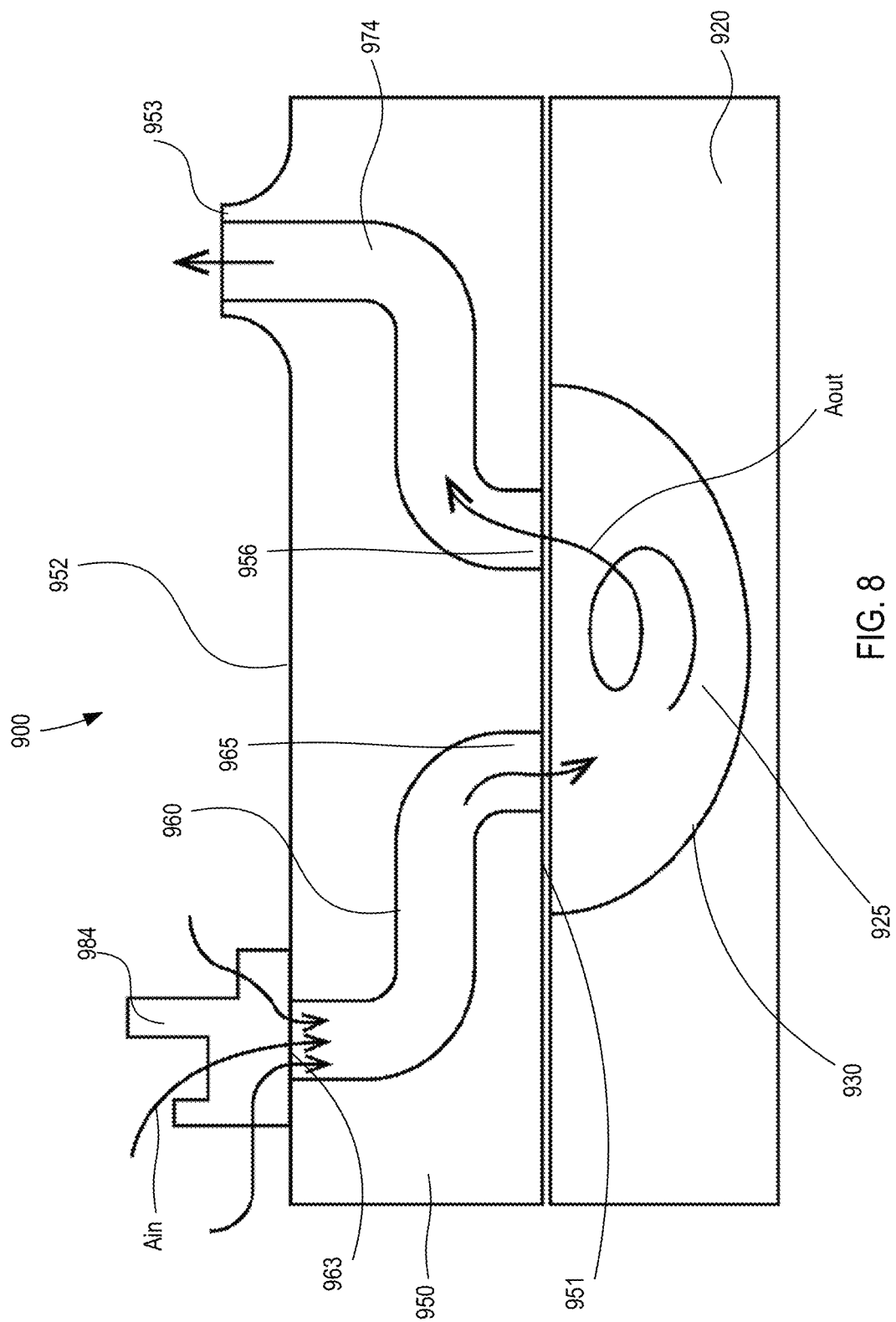
FIG. 8 is a schematic illustration of a medicament delivery device, according to an embodiment.

In some embodiments, any medicament delivery devices described herein can include features to facilitate administration of a dry powder medicament by an untrained or partially-trained user (such as self-administration by a user). For example, in some embodiments, a medicament delivery device can include features to limit variation in the airflow resistance through the device. In this manner, the accuracy and repeatability of the device, including the flow rates, velocities, amount of the delivered and/or fine particle fraction of the delivered dose can be improved. For example, in some embodiments, a medicament delivery device can include spacers, protrusions, or the like configured to limit inadvertent or undesired deformation in flow channels (e.g., deformation or blocking of flow paths due to the patient gripping the device). In other embodiments, a medicament delivery device can include one or more barrier surfaces that limit the likelihood that an external opening through which air is drawn will become blocked. For example, FIG. 8 is a schematic illustration of a medicament delivery device (or drug product) 900 according to an embodiment. The medicament delivery device 900 includes a first member (or portion) 920 and a second member (or portion) 950 coupled to the first member 920. The first member 920 defines at least a portion of a disaggregation chamber 925 that contains a dry powder (not shown). More particularly, the first member 920 includes a chamber wall 930 that forms a boundary of the disaggregation chamber 925. The chamber 925 can be configured such that, as the dry powder is disaggregated into particles within the desired size range, the particles are entrained in the airflow and exit the chamber 925 via an exit opening 956 that is defined by the second member 950 (see the exit airflow Aout in FIG. 8). Although the chamber wall 930 is shown as being curved, in other embodiments, the chamber wall 930 (and any of the chambers described herein) can have any suitable shape. For example, in some embodiments, the chamber wall 930 can be conical, oval, elliptical, polygonal, or spiral shaped.

The second member 950 includes an inner surface 951 and an outer surface 952. The inner surface 951 covers the disaggregation chamber 925 and can be coupled to a corresponding inner surface of the first member 920 by any suitable mechanism described herein. The slight gap shown in FIG. 8 between the first member 920 and the second member 950 is only for purposes of illustration to more clearly identify the inner surface 951. In reality, the first member 920 is coupled to the second member 950 in a manner that prevents air leakage from the interface between the first member 920 and the second member 950. The second member 950 defines an intake channel 960 and an exit channel 974. The exit channel 974 is configured to be fluidically coupled to the disaggregation chamber 925 via an exit opening 956 defined by the surface 951 of the second member 950. In this manner, when a user inhales on the exit channel 974 (e.g., via a mouthpiece 953), inlet air can be drawn from the disaggregation chamber 925 through the exit opening 956 and into the exit passageway 974 to deliver a dose of the dry powder, as shown by the airflow Aout.

The intake channel 960 is configured to be fluidically coupled to the disaggregation chamber 925 via an intake port 965. The intake channel 960 is fluidically coupled to an external volume outside of the disaggregation chamber 925 by an external opening 963 defined by the outer surface 952. As described herein, the characteristics of the inlet air flow as it enters the disaggregation chamber 925 can impact the accuracy and repeatability with which the dry powder P is disaggregated, broken up, and/or otherwise prepared for delivery to the user. Thus, any obstruction of the external opening 963 can reduce the amount of inlet airflow (shown as Ain), thereby changing the performance of the medicament delivery device 900. Accordingly, the outer surface 952 includes one or more barrier surfaces 984 that at least partially surround the external opening 963. The set of barrier surfaces 984 is configured to limit obstruction of the external opening 963, which can be caused, for example, by the user's fingers during use of the device. In some embodiments, the set of barrier surfaces 984 is formed from one or more protrusions extending from the outer surface 952 of the second member 950. In some embodiments, the set of barrier surfaces 984 are non-planar surfaces that at least partially surround the external opening 963. In this manner, when a user's finger (or any other object) contacts the barrier surfaces 984, passageways for the inlet airflow Ain will be maintained by the non-planar structure of the barrier surfaces 984. In some embodiments, the set of barrier surfaces 984 defines one or more tortuous paths within the outer surface 952 of the second member 950 that are in fluid communication with the external opening 963. In this manner, as shown by the arrows entering the external opening 963, the barriers 984 provide a series of alternate paths through which the inlet air can be drawn.

In addition to facilitating a consistent airflow through the disaggregation chamber 925, the medicament delivery device 900 also limits the likelihood that the powder within the disaggregation chamber 925 will be inadvertently conveyed backwards through the intake channel 960. Specifically, as shown, the intake channel 960 includes multiple bends that limit the likelihood that powder inside the disaggregation channel 925 will be conveyed out of the chamber 925 via the intake channel 960 by tipping and/or changing the orientation of the device 900 during use. Similarly stated, the intake channel 960 includes a tortuous path to limit movement of the dry powder from the disaggregation chamber 925 through the intake channel 960 and the external opening 963.

In some embodiments, the medicament delivery device 900 can include properties or characteristics of the medicament delivery device 600 or any of the devices described herein, and vice-versa. For example, in some embodiments, the intake port 965 can be similar to the intake port 665 or the intake port 765 described above. For example, in some embodiments, the intake port 965 can include a transition surface similar to the transition surface 668 shown and described above.

In some embodiments, the medicament delivery device 900 can include a strip or seal (not shown) that fluidically isolates the portion of the disaggregation chamber 925 from the intake channel 960 and/or the exit channel 974. In this manner, the disaggregation chamber 925 functions as a chamber (or a portion of a chamber) within which the dry powder can be both stored and later disaggregated. The strip (or seal) can be any suitable seal shown and described herein (e.g., the strip 110 shown below), or can be similar to the partition 95 shown and described in U.S. Pat. No. 9,446,209 (filed Mar. 9, 2014), entitled "Dry Powder Inhalation Device," which is incorporated herein by reference in its entirety.

In some embodiments, the first member 920 and the second member 950 are monolithically constructed from a polymeric material. Moreover, in some embodiments, the barrier surfaces 984 are monolithically constructed with the second member 950, which, in turn, can be monolithically constructed with the first member 920. In this manner, the device 900 can be a one-piece device that has features (e.g., the barrier surfaces 984) that protect the external opening 963 from obstruction. In some embodiments, the device can be constructed from a degradable material, such as, for example, a degradable material that is biodegradable, degradable via exposure to ultraviolet radiation, or degradable, fragmentable, compostable via exposure to any combination of ultraviolet light radiation, oxygen, moisture and biological organisms.

The medicament delivery device 900 can be used in a manner similar to that described above for the medicament delivery device 600, or any other methods described herein.

Figure 17:
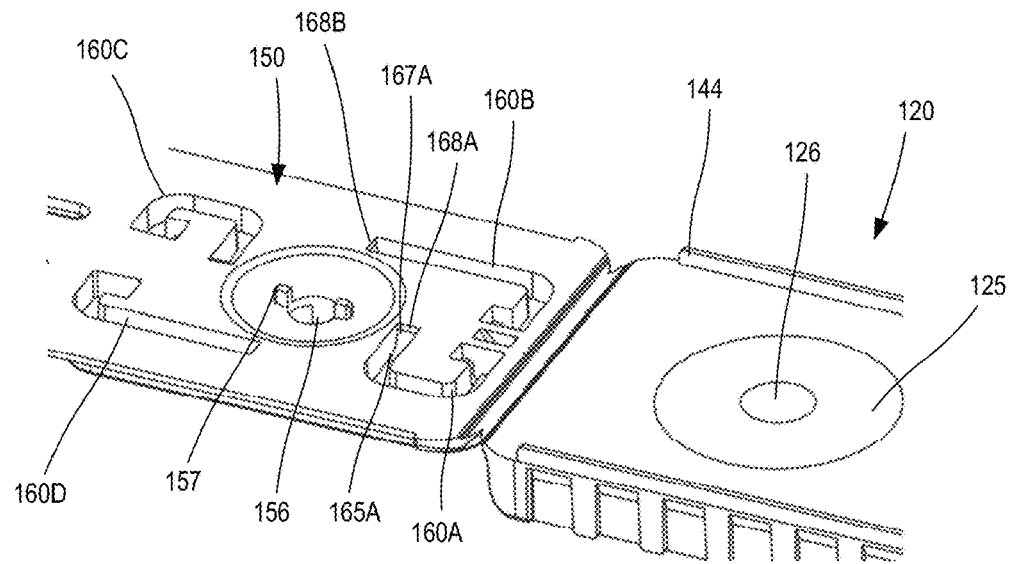
FIG. 17 is a perspective view of the upper portion of the medicament delivery device shown in FIGS. 9-13.
Figure 18:
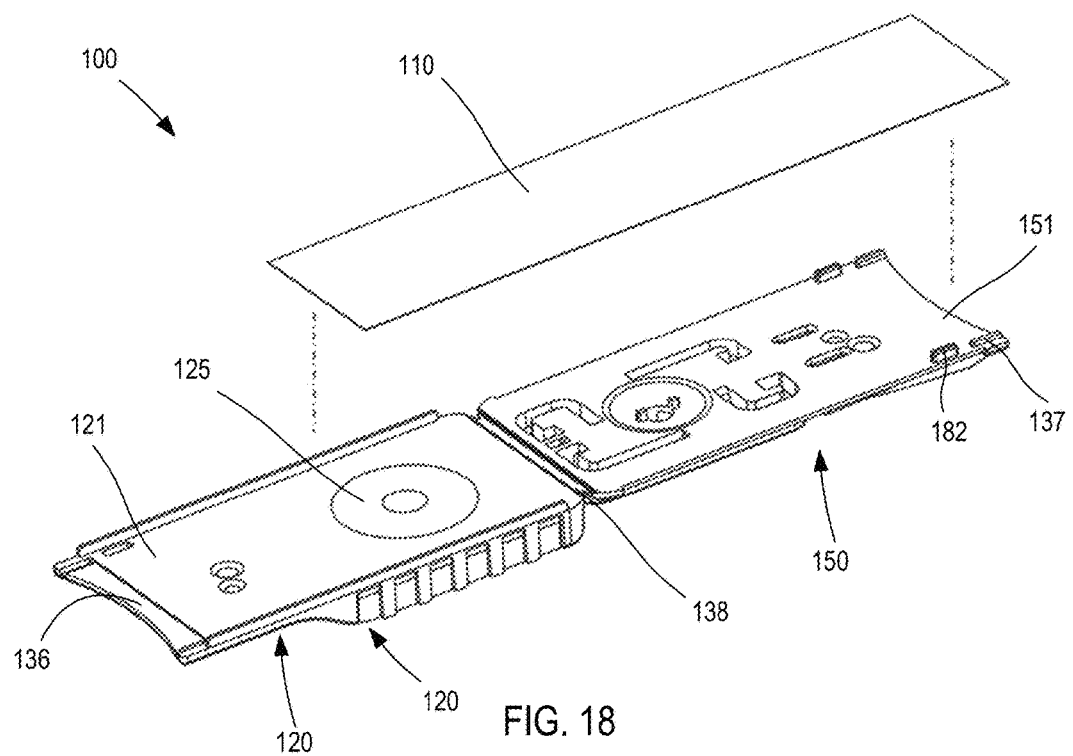
FIG. 18 is an exploded view of the medicament delivery device shown in FIGS. 9-13, in an opened configuration, showing a strip.
Figure 19:
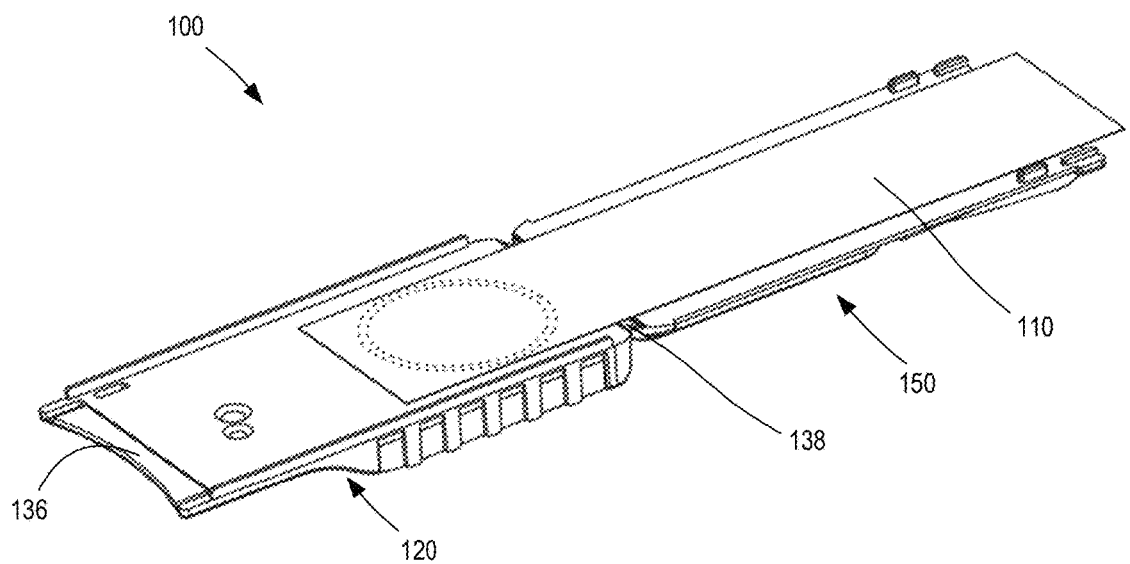
FIG. 19 is a perspective view of the medicament delivery device shown in FIGS. 9-13, in an opened configuration, with the strip coupled to the first member.
Figure 20:
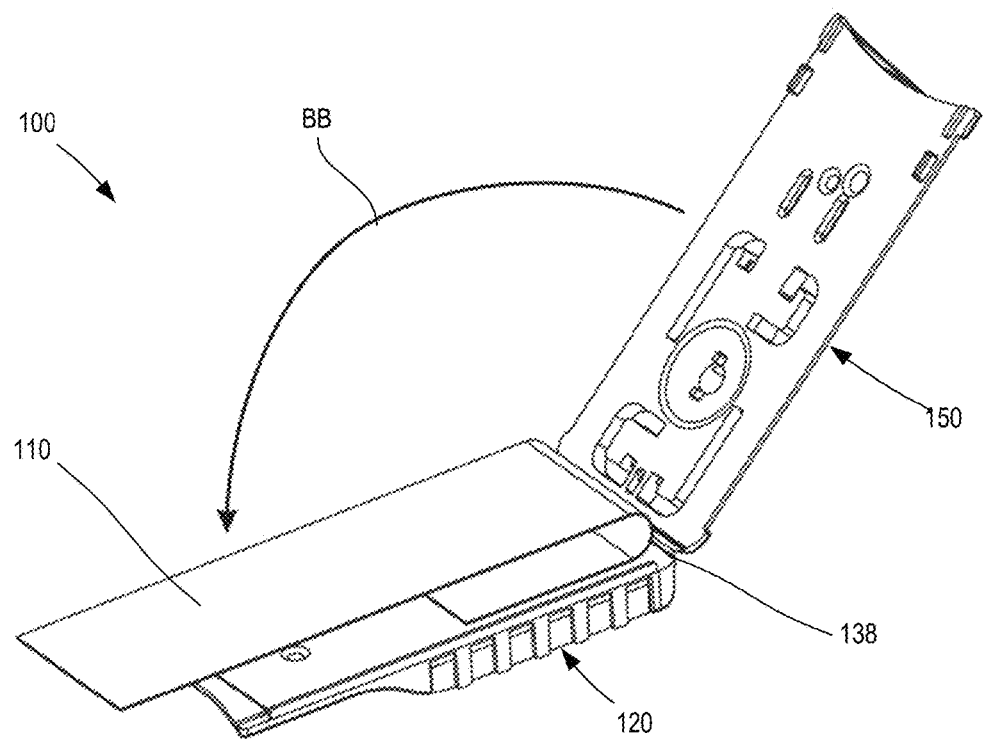
FIG. 20 is a perspective view of the medicament delivery device shown in FIGS. 9-13, being moved from an opened configuration to a closed configuration.

FIGS. 9-29 show various views of a medicament delivery device (or drug product) 100 according to an embodiment. The medicament delivery device 100 includes a lower member (or portion) 120 and an upper member (or portion) 150. FIGS. 9-17 show the lower member 120 and the upper member 150 in a substantially planar configuration to clearly show the features of each member. FIGS. 18-20 show the medicament delivery device 100 being moved from an opened (or planar) configuration to a closed configuration. FIGS. 21-29 show the medicament delivery device 100 with the inner surface 151 of the upper member 150 coupled to the corresponding inner surface 121 of the lower member 120 to form the assembled medicament delivery device 100. As shown in FIGS. 19 and 20, the upper member 150 can be rotated or "folded" onto the lower member 120, as shown by the arrow AA in FIG. 13 and BB in FIG. 20, to form the assembled medicament delivery device 100. When assembled, the medicament delivery device 100 can be similar to, and can include certain features of, any of the medicament delivery devices shown and described in U.S. Pat. No. 9,446,209, entitled "Dry Powder Inhalation Device," which is incorporated herein by reference in its entirety.

Figure 9:
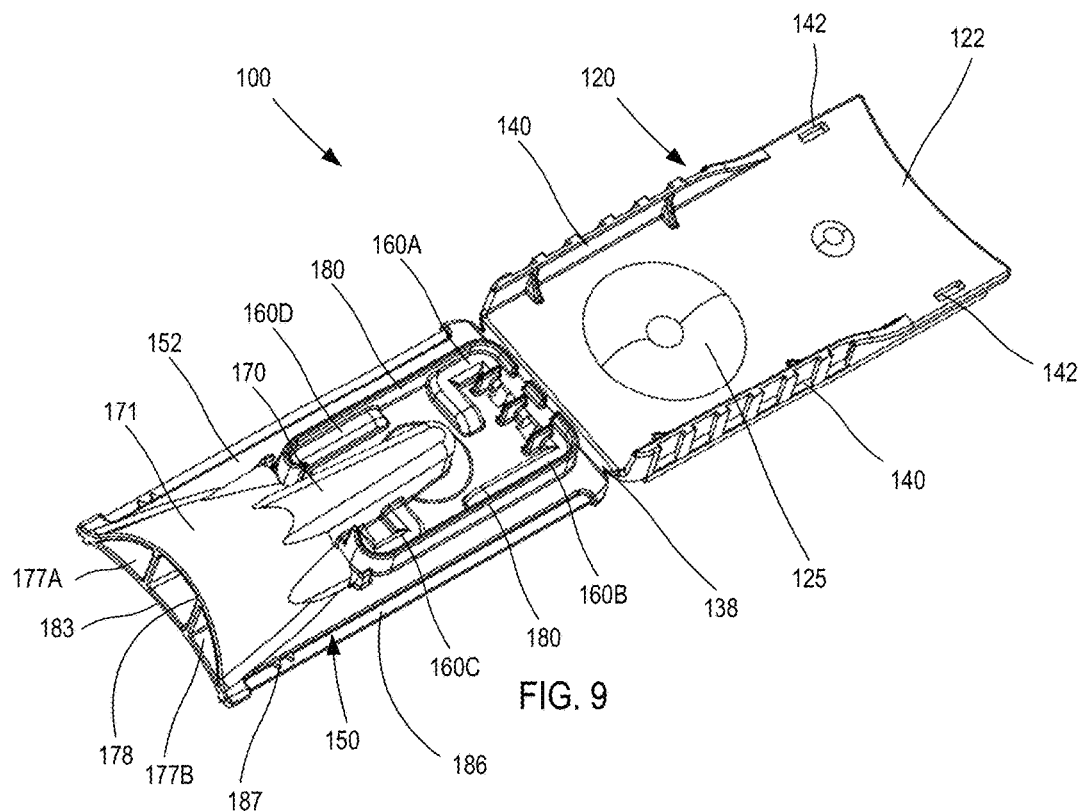
FIGS. 9 and 10 are perspective views of a first side of a medicament delivery device, according to an embodiment.
Figure 10:
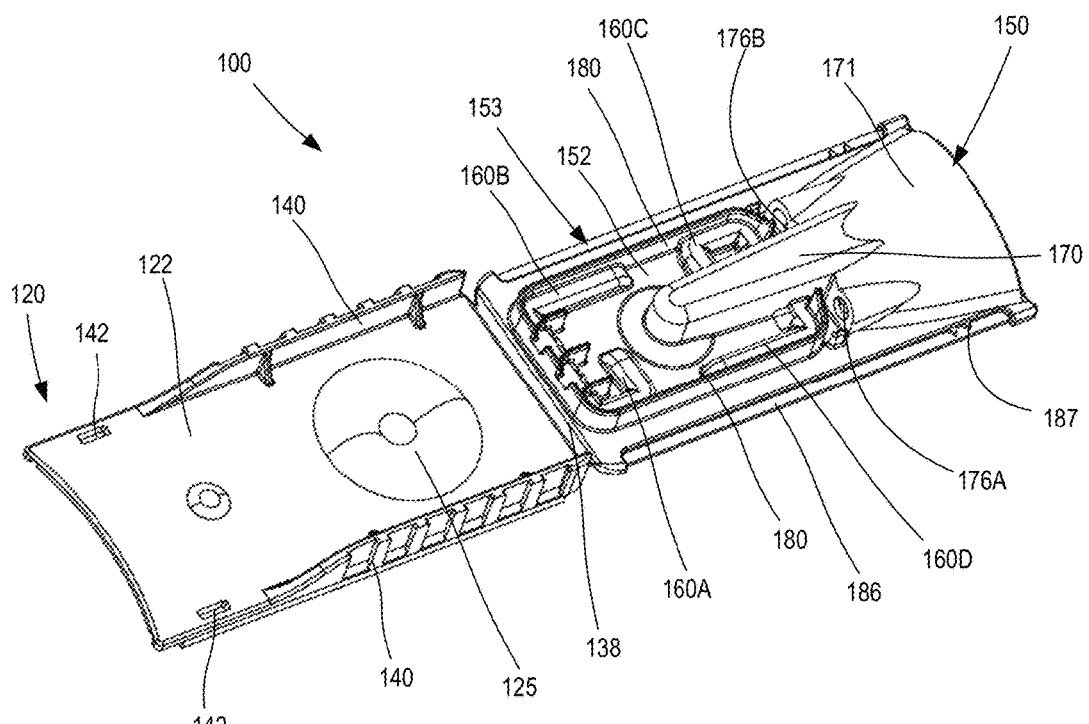

The lower member 120 includes a first (or inner) surface 121 (see FIGS. 13 and 28) and a second (or outer) surface 122 (see FIGS. 9 and 10). The inner surface 121 defines a chamber 125 and one or more injection molding gate recesses 149. The chamber 125 defines a volume or recess within which any suitable medicament is stored. As shown in FIG. 19, a strip 110 (also referred to as a seal member or partition) is coupled to the inner surface 121 to seal and/or maintain a medicament within the chamber 125. The strip 110 can be any suitable member that can be removably coupled about the chamber 125. For example, in some embodiments, the strip 110 can have a peelable heat seal coating to allow the strip 110 to be removed from the inner surface 121 by being peeled from the device 100. The strip 110 can be formulated to be compatible with any of the medicaments and/or drug compositions disposed within the chamber 125. Similarly stated, the strip 110 can be formulated to minimize any reduction in the efficacy of the drug compositions that may result from contact (either direct or indirect) between the seal member and the drug composition within the chamber 125. For example, in some embodiments, the strip 110 can be formulated to minimize any leaching or out-gassing of compositions that may have an undesired effect on the drug composition within the device 100. In other embodiments, the strip 110 can be formulated to maintain its chemical stability, flexibility, strength, and/or sealing properties when in contact (either direct or indirect) with the drug composition within the device 100 over a long period of time (e.g., for up to six months, one year, two years, five years, or longer). In some embodiments, the strip 110 can include a pull tab portion at the distal end. The pull tab portion can be a portion of the strip 110 that extends beyond the mouthpiece of the device 100 and provides a region that the user can easily grasp or pull to remove the strip 110.

Figure 28:
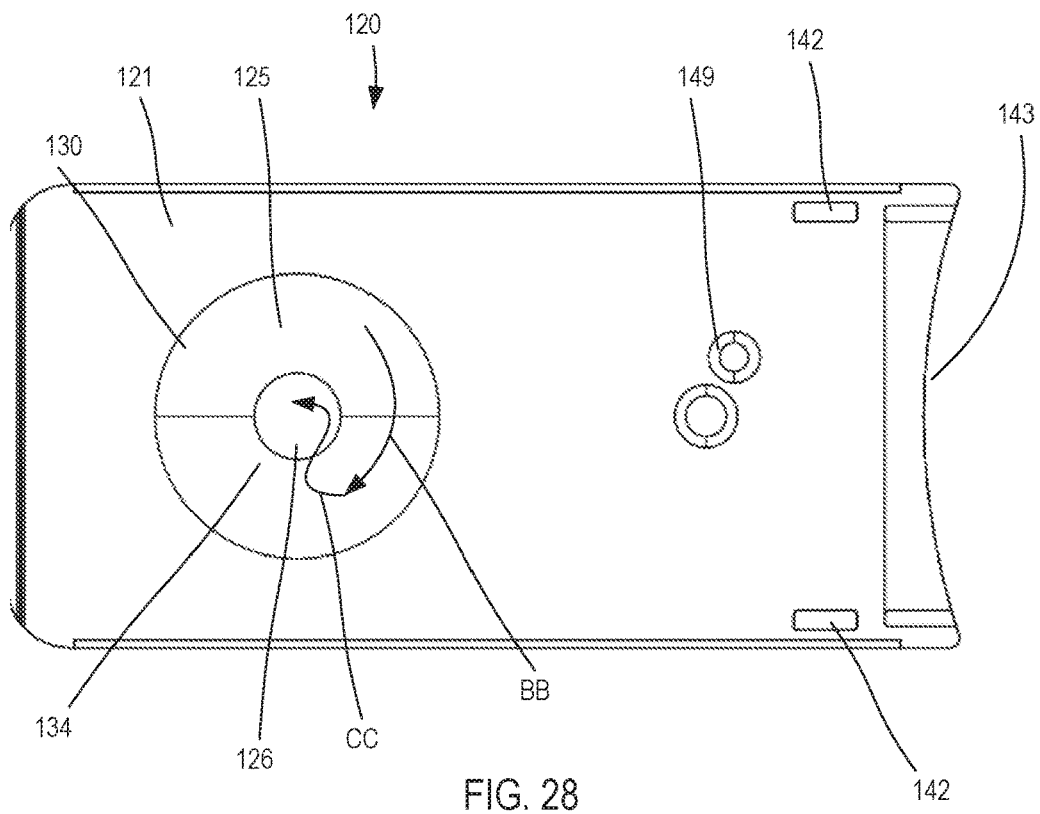
FIG. 28 is a top view of a lower portion of the medicament delivery device shown in FIGS. 9-13, showing an airflow pattern.

In addition to providing a volume or reservoir within which a medicament can be stored, the chamber 125 also functions as a chamber (or a portion of a chamber) within which the medicament can be disaggregated or otherwise prepared for delivery to a patient. Specifically, referring to FIG. 13, the inner surface 121 includes a raised central surface 126 and defines a central axis (or centerline) CL. Thus, when the upper member 150 is coupled to the lower member 120, the chamber 155 (defined by the upper member 150) and the chamber 125 (defined by the lower member 120) define a circular shaped chamber about the raised central surface 126 and the centerline CL. Thus, the chamber 125 forms at least a portion of a disaggregation (and/or dose preparatory) chamber for the device 100. Referring to FIG. 28, the inner surface 121 includes an outer portion (or wall) 130 and an inner portion (or wall) 134, that each form a portion of (or define) the chamber 125. As described below, in use an inlet air flow can flow in a rotational (or swirling manner) within the chamber 125, bounded by the outer wall 130 and the inner wall 134, as shown by the arrow BB in FIG. 28 or the arrows A1 in FIG. 29. The chamber 125 can be configured such that, as the medicament is disaggregated into particles within the desired size range, the particles are entrained in the airflow and exit the chamber 125 via an exit opening 156 that is spaced apart from (and above) the raised surface 126. The exit flow is shown by the arrow CC in FIG. 28 and the arrow A3 in FIG. 29.

Figure 24:
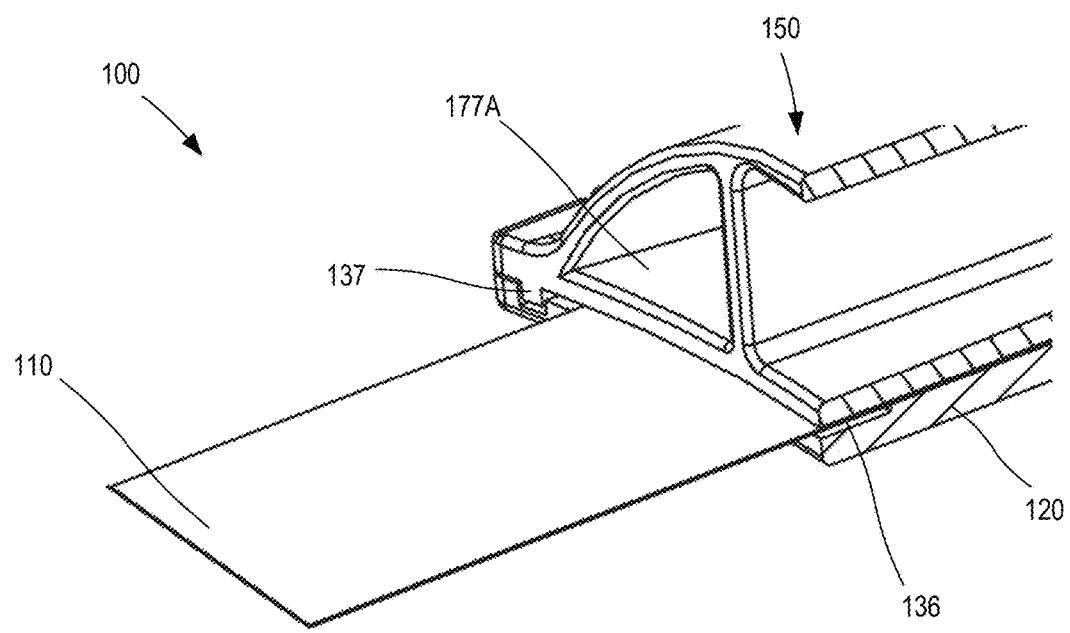
FIG. 24 is a perspective cross-sectional view of the medicament delivery device shown in FIGS. 9-13, in a closed configuration, with the strip in place.
Figure 25:
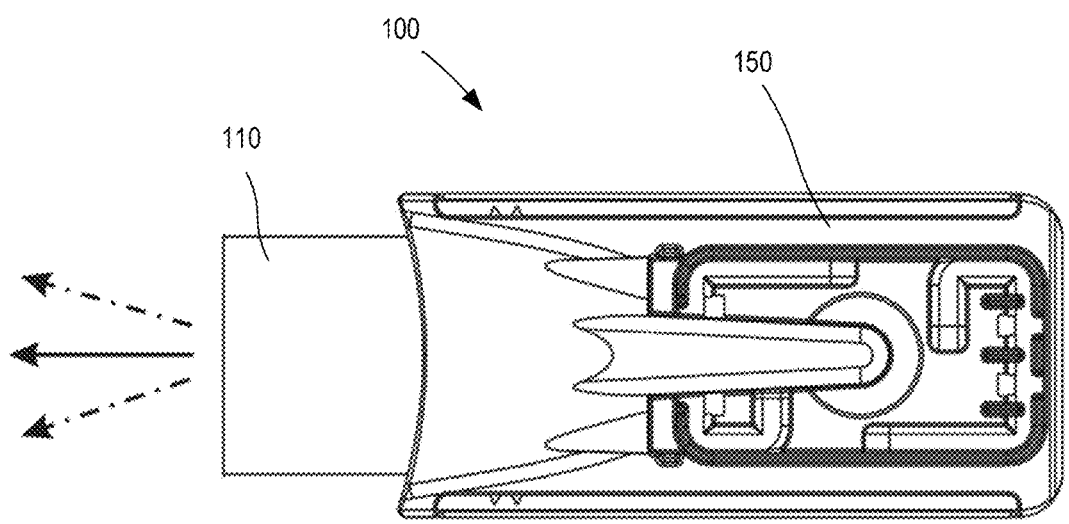
FIG. 25 is a top view of the medicament delivery device shown in FIGS. 9-13, in a closed configuration, with the strip in place.

As shown in FIGS. 12, 19, and 24, the inner surface 121 defines a recess 136 that forms a gap with the mating inner surface 151 of the upper member 150. The recess 136 provides a space within which a portion of the strip 110 can be bunched or deformed when being removed from between the upper member 150 and the lower member 120. As described below, the recess 136 along with the walls 137 limit binding of the strip 110 or portions of the strip 110 (e.g., a pull tab) during removal.

The inner surface 121 also includes two connection flanges 144. During assembly, the connection flanges 144 are deformed to be matingly coupled to a joint surface 186 of the upper member 150 to form a sealed joint between the lower member 120 and the upper member 150.

The second (or outer surface) 122 includes two side edges 140, each of which includes a series of ridges or ribs. The side edges 140 facilitate gripping and manipulation of the device 100 when in its assembled state. As shown the device 100 includes a hinge portion 138 between the lower member 120 and the upper member 150, and about which the upper member 150 can be rotated about the lower member 120 (or vice versa) to form the assembled drug product 100 (see FIG. 20). The lower member 120 defines two coupling slots 142 that receive the coupling protrusions 182 of the upper member 150 when the drug product 100 is in its assembled configuration. More particularly, the coupling protrusions 182 are configured to be matingly coupled within the coupling slots 142 to limit movement of the lower member 120 relative to the upper member 150 after the device 100 is in its assembled configuration. In particular, in some embodiments, the device 100 can be placed in an initial closed configuration after being molded. The coupling protrusions 182 are configured to be temporarily locked within the coupling slots 142 to prevent the device 100 from being opened, unfolded, or otherwise tampered during shipment to a fill/finish operation. By being shipped in an initial (but not permanent) closed configuration, the internal geometry (e.g., the chambers 125, 155, the inlet passageways, the exit passageways) are protected from debris, contamination, and the like. Shipping in the closed configuration also reduces the need for additional shipping containers or packaging, thus reducing manufacturing costs. Although the lower member 120 is shown as defining slots 142 within which the protrusions 182 are received, in other embodiments, either of the lower member 120 or the upper member 150 can define any combination of slots, openings and/or protrusions.

The upper member 150 includes a first (or inner) surface 151 (see FIGS. 13, 14 and 17) and a second (or outer) surface 152 (see FIGS. 9 and 10). The upper member 150 includes an inlet portion 153 and an exit portion 170. Further, the inner surface 151 defines a chamber 155 that, along with the chamber 125, forms a disaggregation chamber or volume, as described above. The inner surface 151 defines one or more coupling recesses 179 for injection molding gate locations 186, and includes the coupling protrusion 182 and the strip (or pull tab) guide walls 137, as described above.

The inlet portion 153 defines a series of inlet passageways (also referred to as intake channels) through which inlet air flows into the disaggregation chamber when the patient inhales through the device 100. As described herein, the characteristics of the inlet air flow as it enters the chambers 125, 155 can impact the accuracy and repeatability with which the medicament within the chambers 125, 155 is disaggregated, broken up, and/or otherwise prepared for delivery to the patient. For example, the shape and size of the inlet passageways can influence the airflow pattern within the chamber 125 (see, e.g., the arrow BB in FIG. 28 and the arrow A1 in FIG. 29). The angle of entry, in turn, can impact the number of revolutions that entrained particles make within the chamber 125 before exiting (see, e.g., the arrow CC in FIG. 28 and the arrow A3 in FIG. 29). Thus, the inlet portion 153 is configured to produce the desired inlet airflow such that the desired exit characteristics (e.g., velocity, flow rate, particle size distribution) are achieved. For example, in some embodiments, the drug product 100 (or any other drug products described herein) can produce a particle size distribution well suited for reaching the deeper areas (e.g., alveoli) of the lungs.

Figure 14:
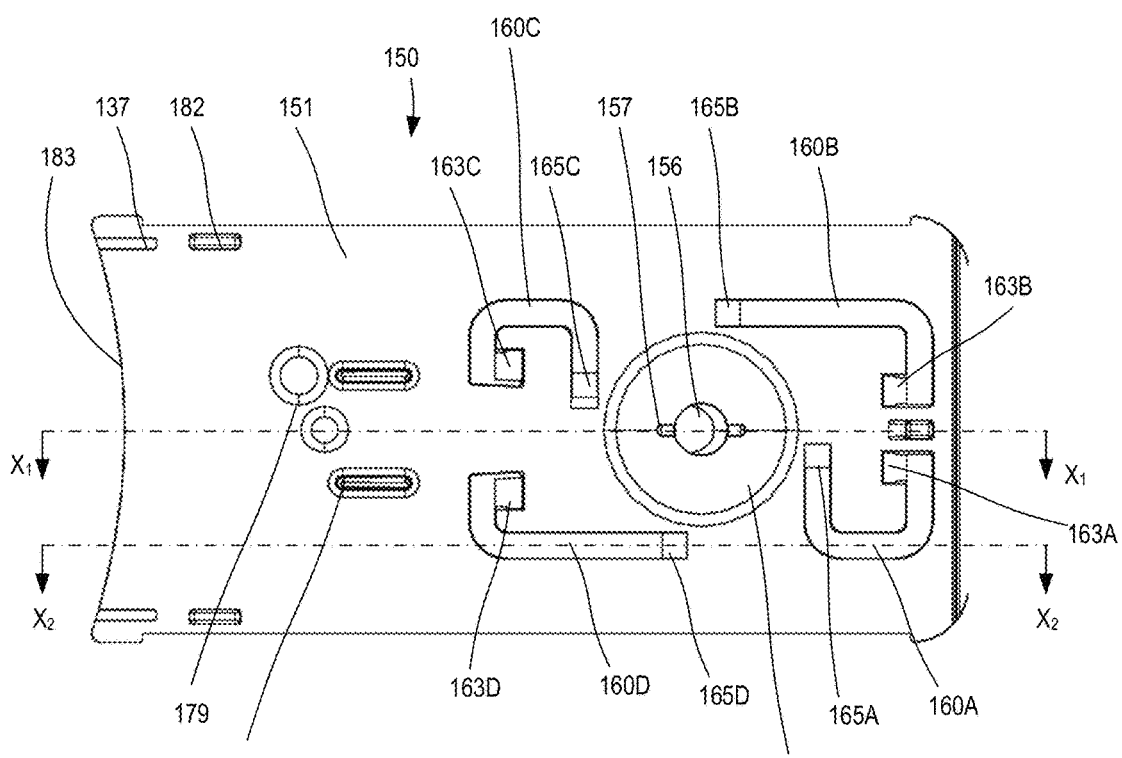
FIG. 14 is a top view of an upper portion of the medicament delivery device shown in FIGS. 9-13.

In particular, the inlet portion 153 includes four inlet passageways (also referred to as intake channels): a first inlet passageway 160A, a second inlet passageway 160B, a third inlet passageway 160C, and a fourth inlet passageway 160D. Referring to FIG. 14, the first inlet passageway 160A includes an external opening 163A through which inlet air is drawn from outside of the device 100, and intake port 165A through which the inlet air is conveyed into the chambers 155, 125, and a curved portion therebetween. The second inlet passageway 160B includes an external opening 163B through which inlet air is drawn from outside of the device 100, and intake port 165B through which the inlet air is conveyed into the chambers 155, 125, and a curved portion therebetween. The third inlet passageway 160C includes an external opening 163C through which inlet air is drawn from outside of the device 100, and intake port 165C through which the inlet air is conveyed into the chambers 155, 125, and a curved portion therebetween. The fourth inlet passageway 160D includes an external opening 163D through which inlet air is drawn from outside of the device 100, and intake port 165D through which the inlet air is conveyed into the chambers 155, 125, and a curved portion therebetween.

Figure 21:
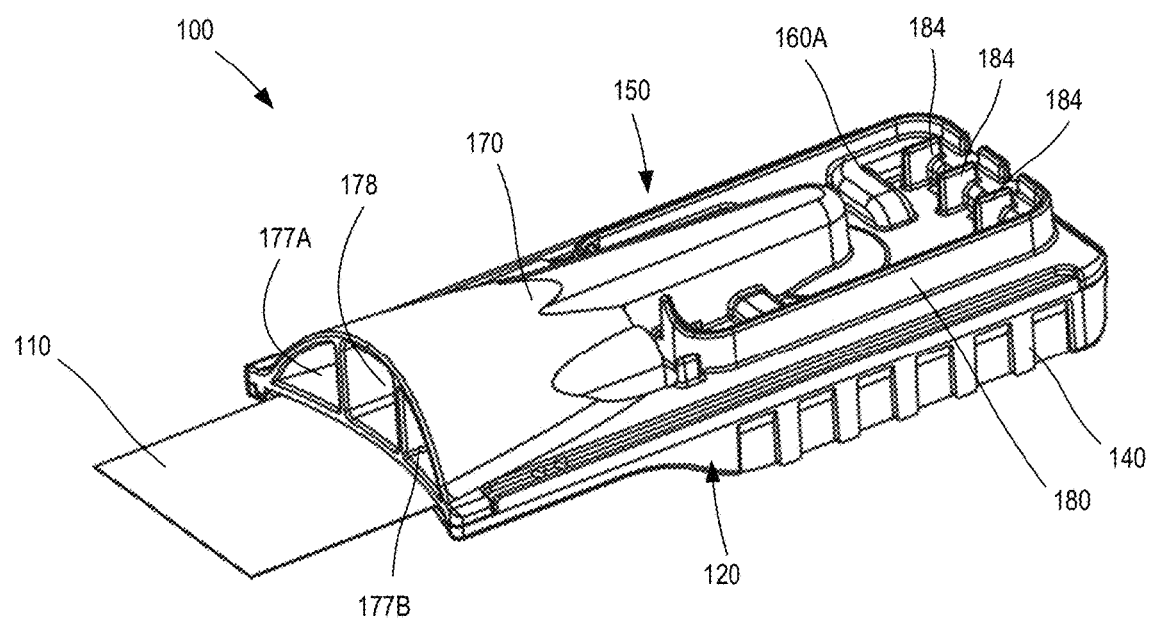
FIG. 21 is a perspective view of the medicament delivery device shown in FIGS. 9-13, in a closed configuration, with the strip in place.
Figure 22:
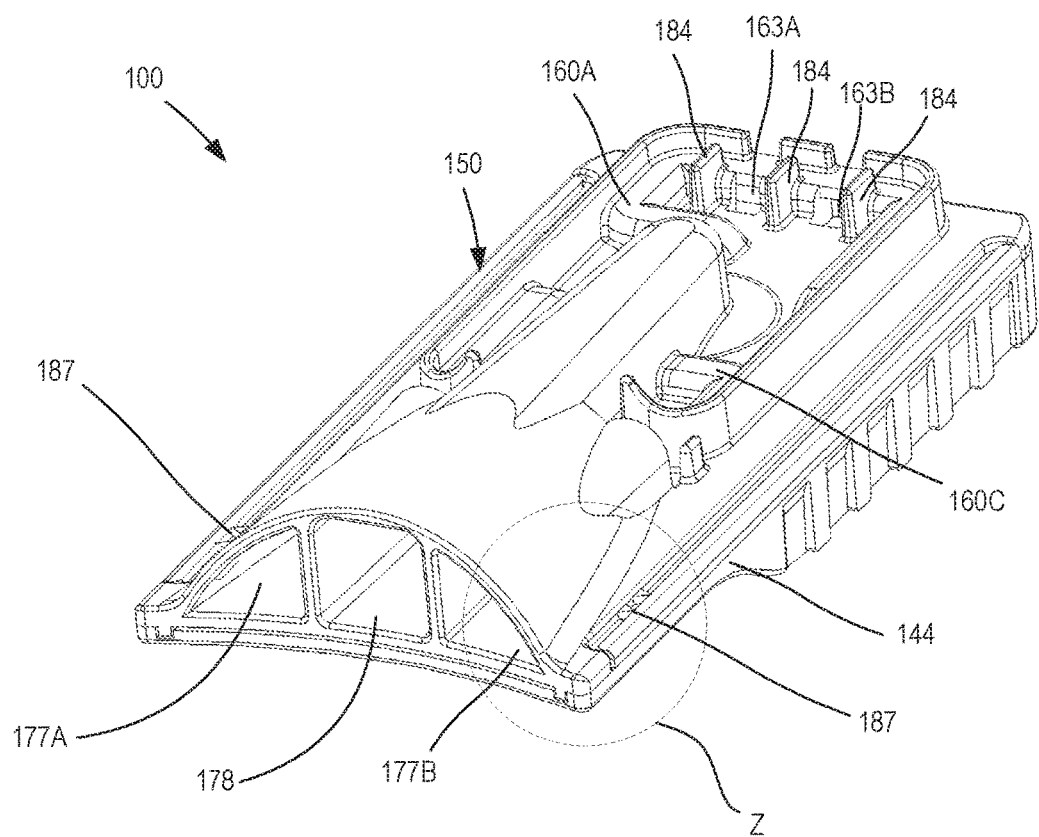
FIG. 22 is a perspective view of the medicament delivery device shown in FIGS. 9-13, in a closed configuration, with the strip removed.
Figure 23:
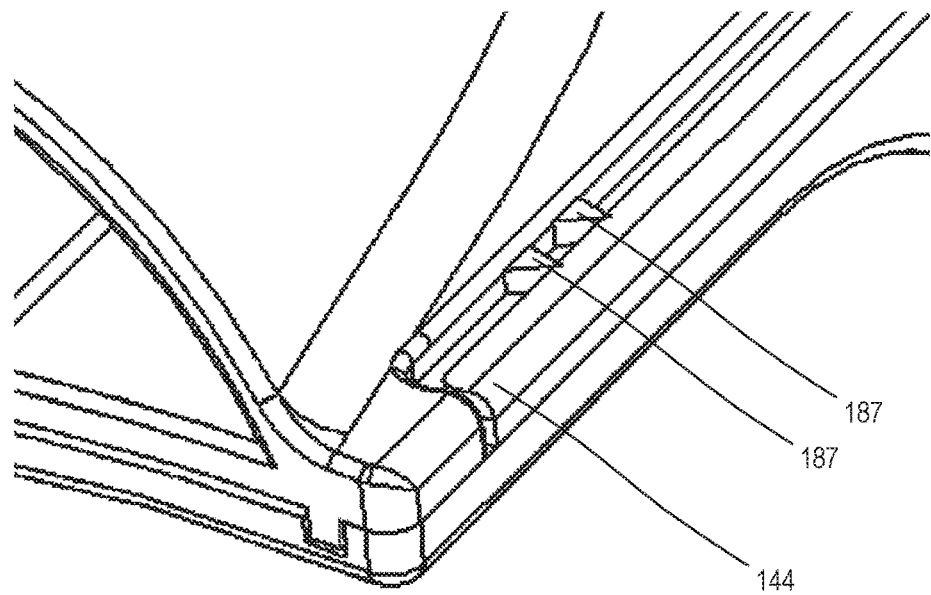
FIG. 23 is an enlarged view of a portion of the medicament delivery device shown in FIG. 22 identified by the region Z in FIG. 22.
Figure 26A:
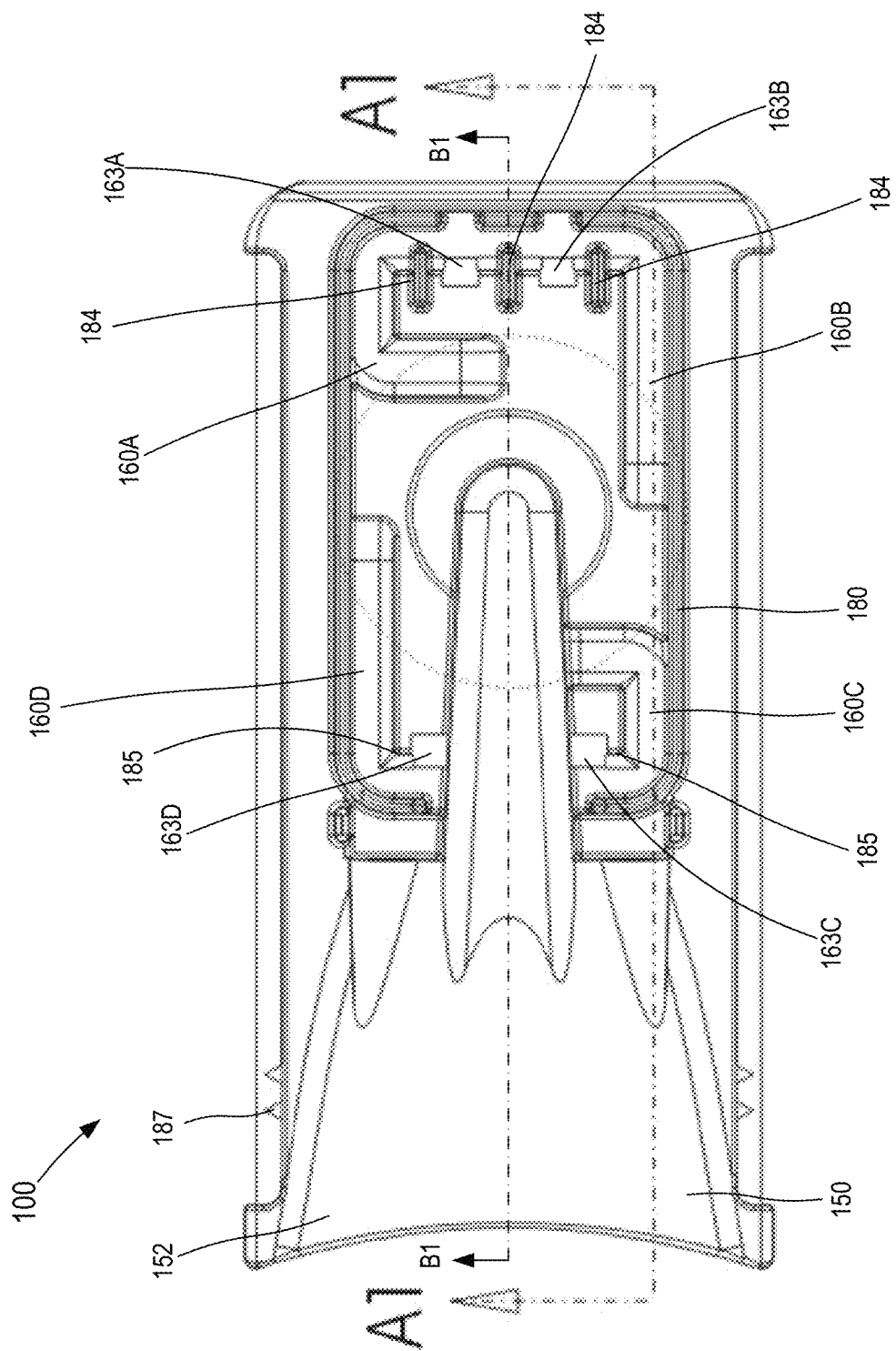
FIG. 26A is a top view of the medicament delivery device shown in FIGS. 9-13, in a closed configuration, with the strip removed.

The outer surface 152 of the upper member 150 includes a shroud (or ridge) 180 that surrounds the external openings 163A, 163B, 163C, 163D. The shroud 180 provides a surface that the user can contact when manipulating the device 100 when in its assembled state. As described above, the side edges 140 also facilitate gripping and manipulation. The shroud 180 can be either continuous or can be interrupted about the outer edge of the upper member 150. The shroud 180 also provides a barrier adjacent the external openings that limit the likelihood that the external openings 163A, 163B, 163C, 163D will become obstructed by the user's fingers or other materials during use. In addition to the shroud 180, as shown in FIGS. 21 and 22, the outer surface 152 includes a first set of barrier protrusions (or surfaces) 184 that at least partially surround the external opening 163A and the external opening 163B. As shown in FIG. 26A, the outer surface 152 includes a second set of barrier protrusions (or surfaces) 186 that at least partially surround the external opening 163C and the external opening 163D. The barrier surfaces 184, 185 are also configured to limit obstruction of the external openings, which can be caused, for example, by the user's fingers during use of the device. In particular, the set of barrier protrusions 184 include multiple non-planar surfaces that at least partially surround the external openings 163A, 163B. In this manner, when a user's finger (or any other object) contacts the barrier surfaces 184, passageways for the inlet airflow will be maintained by flow around the non-planar structure of the barrier surfaces 184.

Figure 27:
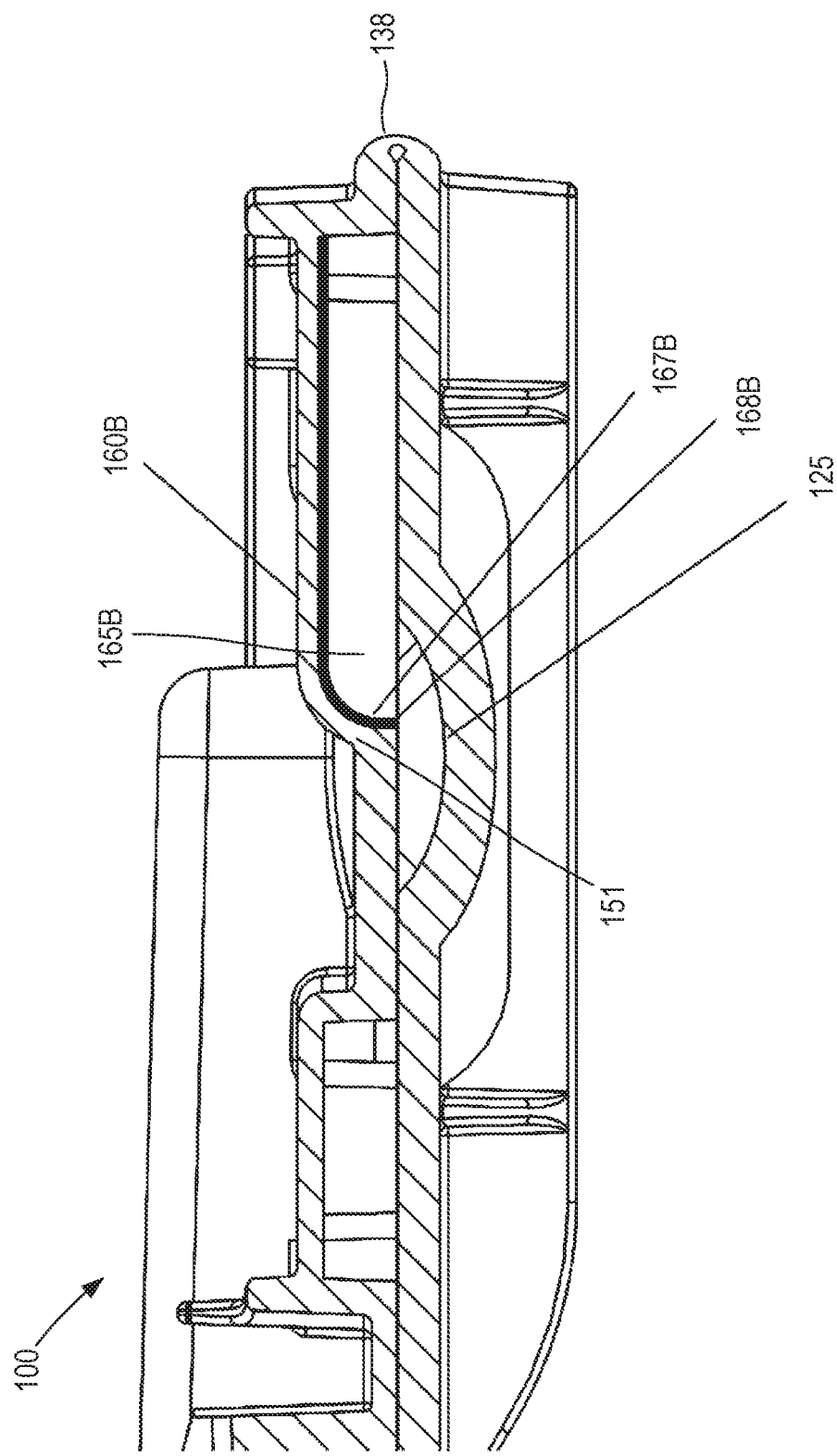
FIG. 27 is an enlarged view of a portion of the medicament delivery device shown in FIG. 26B identified by the region Z in FIG. 26B.
Figure 29:
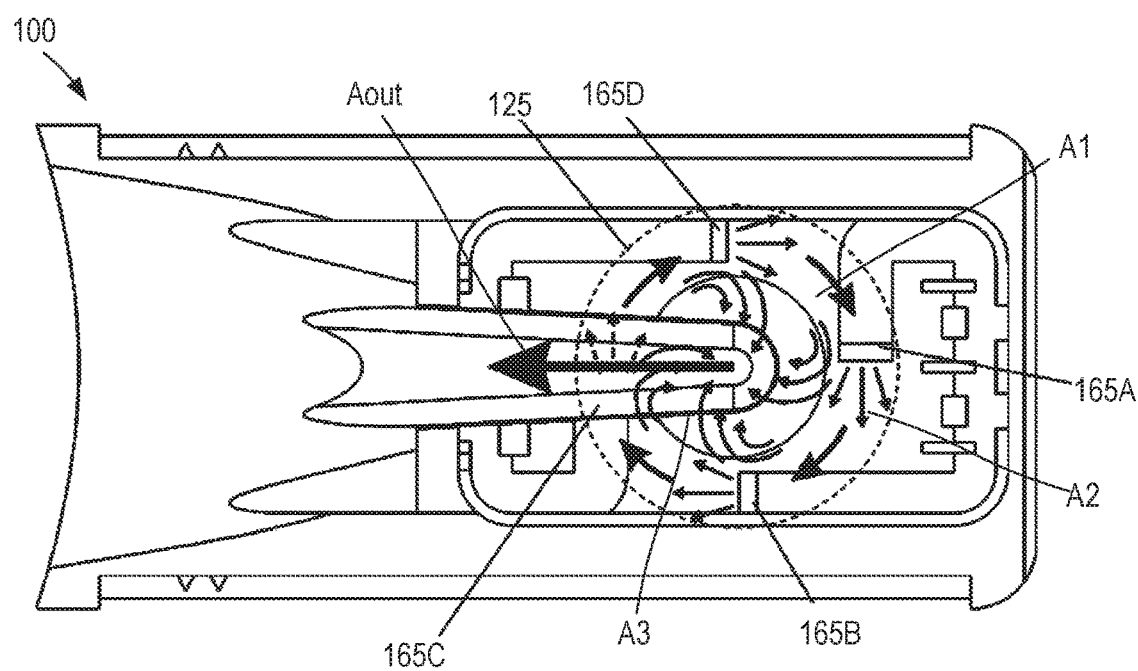
FIG. 29 is a top view of the medicament delivery device shown in FIGS. 9-13, in the closed configuration, showing an airflow pattern.

The intake ports 165A, 165B, 165C, 165D are located on the inner surface 151 such that they open in to (or are in fluid communication with) the chamber 125 after the removal of strip (or seal) 110 that is disposed about the chamber 125. In this manner, upon inspiration (inhalation) by the patient, air is drawn from outside of the device through the external openings 163A, 163B, 163C, 163D, within the various curved portions of each of the inlet passageways, and into the chamber 125 via the intake ports 165A, 165B, 165C, 165D. As described above, the inlet passageways 160A, 160B, 160C, 160D can include any suitable geometry or size to produce the desired airflow characteristics within the chamber 125. For example, as shown in FIG. 17, the intake port 165A can be defined and/or bounded by an intake ramp 167A that includes a termination edge (or surface) 168A. Similarly, FIGS. 17 and 27 shows a side cross-sectional view of a portion of the intake port 165B, which is bounded by an intake ramp 167B that includes a termination edge (or surface) 168B. The transition of the ramps at the termination edge intersect (or forms an edge with) the inner surface 151 of the second member 150. As described above with reference to the device 600, the transition edges (or surfaces) 168A, 168B each forms an exit angle with respect to the surface 151 that can have any suitable value. For example, the exit angle can be less than 105 degrees. In some embodiments, the transition surface 168A is parallel to the center axis CL of the disaggregation chamber 125 (i.e., the exit angle is about 90 degrees). By having an exit angle of less 105 degrees (or at about 90 degrees), the transition surface 168A advantageously produces a sudden expansion into the disaggregation chamber 125. Referring to FIG. 29, this arrangement produces a flow separation or disruption of recirculating rotational flow when a second portion A2 of the inlet airflow is conveyed from the intake channel 160A to the chamber 125. In some embodiments, the flow separation can produce recirculation of the second portion A2 of the inlet airflow or can otherwise cause the second portion A2 of the inlet airflow to be disrupted or "fan out" in one or more directions that are not tangential to the chamber wall, as shown by the arrows A2 in FIG. 29. This arrangement produces improved disaggregation of the dry powder and mixing of the particles within the airflow.

Referring to FIG. 27, in some embodiments, the termination edge (the intersection of the termination surface 168A and the inner surface 151) can be a substantially sharp edge (e.g., have an edge radius of less than about 50 microns). This can further enhance flow separation as the second portion of the inlet airflow is conveyed through the intake port 165A and into the disaggregation chamber. In some embodiments, the inclusion of sharp edges that bound the intake port 165A (or any of the exit openings described herein) produces a flow separation when the air flow is conveyed from the inlet passageway to the chamber 125. This produces a more dispersed or "fanned-out" air jet within the chamber 125, which can facilitate mixing. In other embodiments, however, the edge between the transition surface 168A and the inner surface 151 can be curved or have a radius of greater than about 50 microns (i.e., can include an edge break). In other embodiments, the termination edges can be curved, radiused, interrupted (i.e., can include an edge break), or the like.

The exit ramp 167A is the side wall that forms the end portion of the inlet passageway 160A and the boundary of a portion of the intake port 165A. The exit ramp 167A is a curved surface (i.e., a continuous, non-linear surface). The curved shape of the exit ramp 167A results in a more gradual (or smoother) exit from this portion of the intake port 165A. In some embodiments, the exit ramp 167A can be curved in multiple dimensions as described herein. Although the termination surface 168A and the exit ramp 167A are described with respect to the intake port 165A, any of the intake ports described herein can include similar structure. Moreover, although the exit ramp 167 is described as being curved or non-linear, in other embodiments, the exit ramp 167 can be a linear "ramped" surface and/or can include linear portion.

The exit portion 170 of the upper member 150 includes a top surface 171 and a curved, distal edge 183. The curved distal edge 183 is aligned with (or mates with) the distal edge 143 of the lower portion 120 to define the distal end portion (or mouthpiece) of the device 100. The exit portion 170 defines a central exit opening 156, an exit passageway 174 (see FIG. 15) and two bypass passageways (see e.g., passageway 175A in FIG. 16). The curved distal edge 183 defines the exit opening 178 through which the inlet air entrained with the medicament particles is conveyed. Specifically, in use air is drawn from the chamber 125, 155, through the central exit opening 156 and into the exit passageway 174, as shown by the arrow DD in FIG. 15. The airflow, entrained with medicament particles enters into the exit opening 156 via a substantially cylindrical flow area (or shroud) defined between the inner surface 151 of the upper member 150 and the raised surface 126 of the lower member 120. This flow path produces additional dynamic flow patterns that facilitate further disaggregation of the medicament particles.

As described herein, the dry powder P can also include any suitable excipient, such as, for example, lactose. The dry powder P can often include predominantly the excipient with a small percentage of the mass being the API (e.g., one to ten percent). Thus, the delivery characteristics of the device 100 can be dependent on the lactose characteristics (or the grade of lactose included within the dry powder P). For example, some dry powder P can include a non-sieved lactose with a mean diameter of 60 microns. Such powder formulations therefore include the fine lactose particles (e.g., 1-5 microns), and thus can be more "sticky" than those formulations that do not include as much of the fine particles. The advantage of using such non-sieved lactose is that a higher percentage of fine particles can be delivered, which can be beneficial for the desired treatment (e.g., deep lung delivery or the like). Such non-sieved formulations, however, can require more turbulent airflow to disaggregate the stickier fine particles than is needed for a sieved formulation. Thus, the transition surface 168 and the exit angle Θ can be optimized for use with (and can provide the desired amount of disruptive airflow) for a non-sieved formulation. Thus, in some embodiments, the dry powder P can include a non-sieved lactose formulation having a mean particle diameter of 60 microns. In other embodiments, the dry powder P can include a sieved lactose formulation having an initial mean particle diameter of 60 microns, but with a substantial amount of the fine particles removed by the sieve operation.

Figure 13:
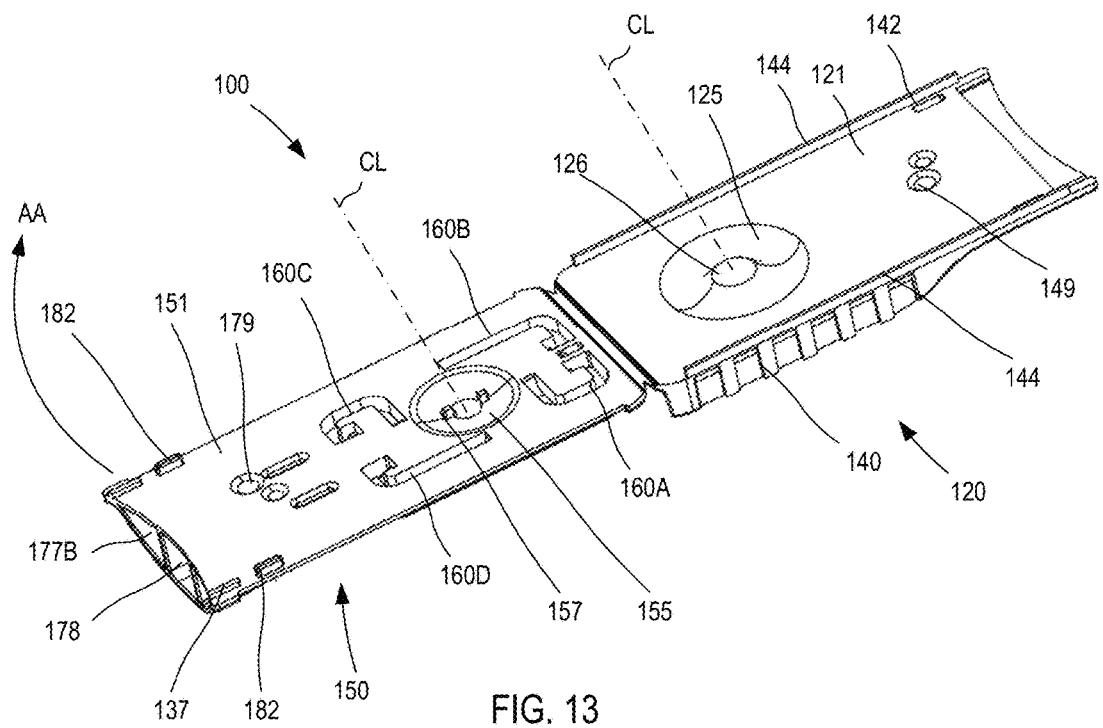
FIG. 13 is a perspective view of a second side of the medicament delivery device shown in FIGS. 9 and 10.
Figure 15:
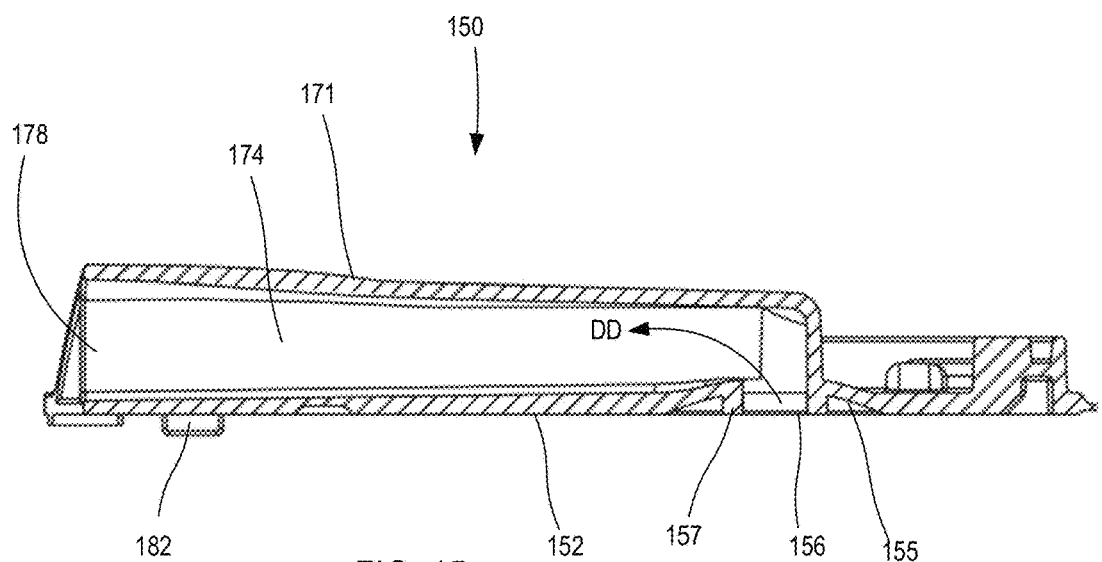
FIGS. 15 and 16 are cross-sectional views of the upper portion of the medicament delivery device shown in FIGS. 9-13, taken along lines $X_1$-$X_1$ and $X_2$-$X_2$, respectively.

As shown in FIGS. 13, 15, and 26C, the inner surface 151 of the upper member includes two protrusions 157 that are positioned adjacent the exit opening 156. When the device 100 is in its assembled configuration, the two protrusions 157 contact the raised surface 126. This arrangement maintains a constant distance between the exit opening 156 and the raised surface 126, thereby producing a consistent flow area during use, as well as a gap within which the strip 110 can reside without being pinched between the first member 120 and the second member 150. For example, the contact between the protrusions 157 and the raised surface 126 prevents deflection of the upper member 150, for example, if the user squeezes the device 100 during use. Such undesirable deflection could, for example, reduce the flow air thereby choking the flow or otherwise decreasing the flow within the chamber 125. Similarly stated, in some embodiments, the annular "air gap" defined between the raised surface 126 and the exit opening 156 can be an air flow constriction point, which can generate particle collisions (and disaggregation). Maintaining the constant distance during use (and between various users), as described herein, facilitates a consistent air flow resistance during use. This, in turn, improves dose delivery consistency and maintains a consistent air flow resistance level experienced by the patient. Thus, the protrusion 157 provides for a more consistent, repeatable delivery of the medicament.

Figure 16:
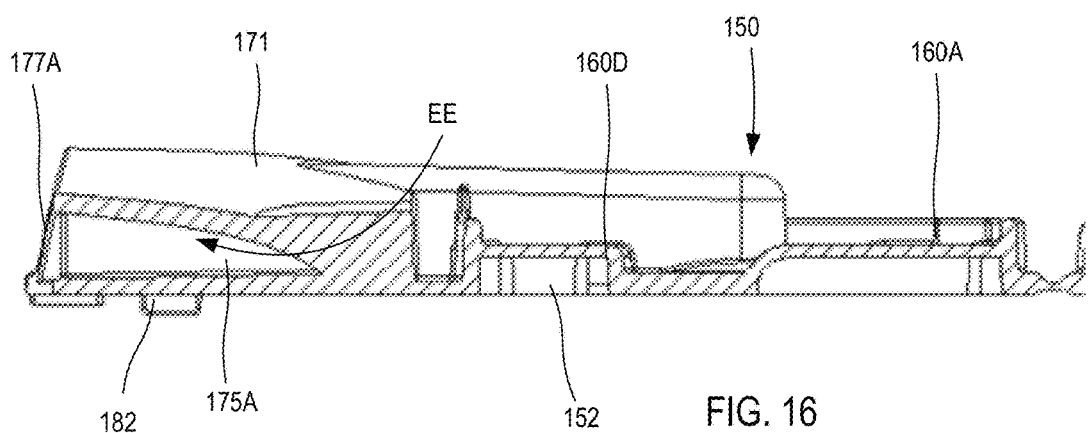

The two bypass passageways (see e.g., passageway 175A in FIG. 16) provide a flow path through which a portion of the air produced by inspiration flows outside of the chamber 125, 155 (see also the arrow EE in FIG. 16). Specifically, the exit portion 170 defines the bypass passageway 175A that receives bypass air via the bypass inlet 176A (see FIG. 10) and the bypass passageway that receives bypass air via the bypass inlet 176B (see FIG. 10). As shown in FIG. 9, the curved distal edge 183 defines the bypass openings 177A, 177B through which the bypass air flows from the bypass passageways and into the user's mouth. The bypass passageways can be sized (or tuned) to manipulate the air flow resistance through the chamber 125.

The medicament delivery device 100 can be used to treat any number of indications, including asthma and chronic obstructive pulmonary disease (COPD). In use, the user first removes any packaging or overwrap (not shown, but which can be similar to the protective overwrap 711 shown and described below) from about the device 100. The user then removes the strip 110 by pulling the strip as shown by the arrows in FIG. 25. As described above, the inclusion of the recess 136 and the strip guide walls 137 allows portions of the strip 110 to become compressed together (or bunched up) if pulled slightly to one side or the other (i.e., if pulled in a direction that is not parallel to a longitudinal axis of the strip 110). This bunching will provide a region of increased strength, thereby allowing the strip 110 to be successfully removed from the device 100 without tearing or breaking. Similarly stated, the recess 136 and strip guide wall 137 provide a volume that does not pinch, bind, or otherwise promote tearing of the strip 110 during removal.

After the strip 110 is removed, the user then places the distal end portion (or mouthpiece) of the assembled device 100 into their mouth. The user then inhales, which draws air into the two bypass inlet openings 176A, 176B, and also the four external openings 163A, 163B, 163C, 163D. As described above, the portion of the air that is drawn through the four external openings 163A, 163B, 163C, 163D (referred to as the inlet airflow) is conveyed into the chamber 125, 155 via the respective inlet air passageways 160A, 160B, 160C, 160D. The structure defining the intake ports 165A, 165B, 165C, 165D imparts the desired flow characteristics to the inlet airflow as it enters the chamber 125, 155, as described herein. The inlet airflow moves within the chamber 125 (see, e.g., FIGS. 28 and 29) and entrains the dry powder medicament stored therein. Continued dynamic motion of the inlet airflow causes disaggregation of the particles, thus producing the desired emitted dose and fine particle mass and particle size distribution of dose delivery to the patient. The inlet airflow, entrained with the medicament particles, is then conveyed into the exit passageway 174 via the opening 156, as described above.

The chamber 125 and the chamber 155 can be of any suitable size to produce the desired airflow and disaggregation properties. For example, although the chamber 125 is shown as being deeper than the chamber 155, in other embodiments, each of the chamber 125 and the chamber 155 can have any suitable depth and/or diameter to achieve the desired drug delivery performance. For example, in some embodiments, an upper member (e.g., the upper member 150) can include features that are similar to and/or symmetrical with those features of a mating lower member (e.g., the lower member 120). For example, in some embodiments an upper member can include a raised surface, similar to the raised surface 126, that defines an opening, similar to the opening 156. In this manner, the circular shape of the disaggregation chamber can be produced by both the upper member and the lower member. In other embodiments, a ratio between the depth of a chamber defined by an upper member (e.g., chamber 155) to the depth of a chamber defined by a lower member (e.g., chamber 125) can be at least 0.75, at least 0.9, or at least 1.0. By producing a substantially symmetrical design (e.g., a ratio of about 1.0), the device can produce the desired airflow entrained with medicament particles independently of the orientation of the device. Similarly stated, this arrangement can produce substantially the same drug delivery characteristics whether the device is used with the upper member (e.g., the upper member 150) facing upwards or downwards.

The arrangement of the raised surface 126 and the curved upper chamber 155 also limits the likelihood that the powder within the disaggregation chamber 125, 155 will be inadvertently conveyed out of the exit opening 156 without being properly disaggregated if the device 100 is tipped or turned upside down during use. Specifically, as described, the dose of dry powder is delivered via an annular opening between the raised surface 126 of the lower member 120 and the surface of the upper member 150. The annular opening (or gap) can prevent powder from remaining on the surface of the upper member 150 if the device 100 is turned upside down. The intake channel also limits the likelihood that the powder will exit (or be spilled) backwards out of the dose chamber by including a series of bends (or a tortuous path).

FIG. 30 is a flow chart of a method 10 of using a dry powder inhaler, according to an embodiment. Although the method 10 is described with reference to the medicament delivery device 100, in other embodiments, the method 10 can be performed using any of the medicament delivery devices described herein. The method includes moving a strip from a first position between a first member of a dry powder inhaler and a second member of the dry powder inhaler to a second position, at 12. The strip seals a dry powder within a portion of a disaggregation chamber defined by a chamber wall of the first member when the strip is in the first position. The portion of the disaggregation chamber is in fluid communication with an exit channel defined by the second member and an intake channel defined by the second member when the strip is in the second position. A mouthpiece of the dry powder inhaler is then placed into a mouth, at 14.

The method further includes inhaling into the mouth to draw an inlet airflow through the intake channel and into the disaggregation chamber, at 16. A portion of the intake channel is shaped and/or positioned such that a portion of an inlet airflow has a rotational motion within the disaggregation chamber. The rotational motion disaggregates the dry powder to produce respirable particles within the rotational airflow. The intake channel and the exit channel are collectively configured to produce an exit airflow containing the respirable particles for at least two seconds.

In some embodiments, the method 10 optionally includes disposing of the dry powder inhaler, including the first member and the second member, at 17. For example, in some embodiments, the dry powder inhaler is a unit dose device, also known as single-use device that is discarded after use. In some embodiments, the first member and the second member of the dry powder inhaler are monolithically constructed from a degradable material, such as, for example, a degradable material that is biodegradable, degradable via exposure to ultraviolet radiation, or degradable, fragmentable, compostable via exposure to any combination of ultraviolet light radiation, oxygen, moisture and biological organisms. Such material can limit possible issues with discarding the single-use device.

Figure 31:
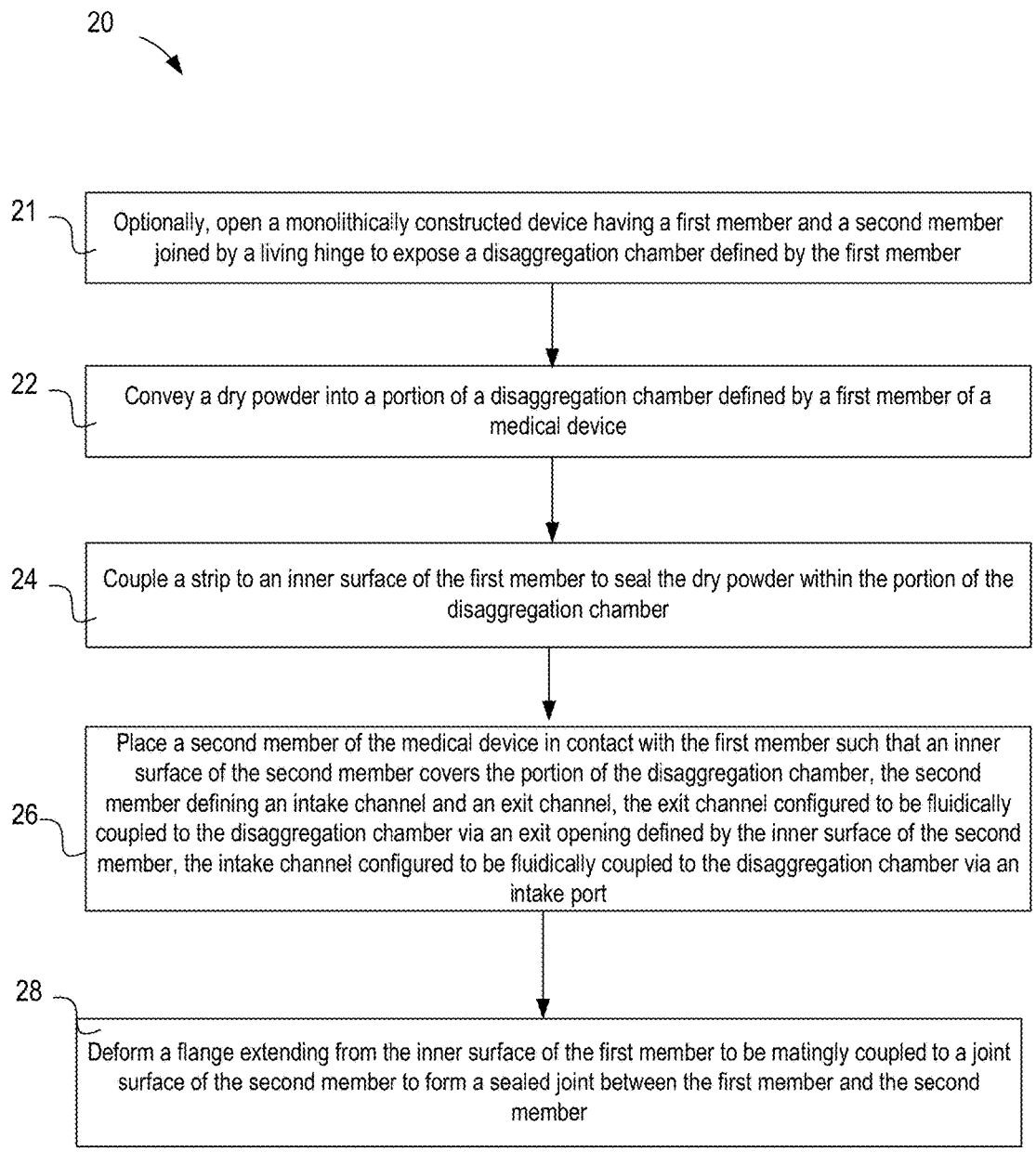
FIG. 31 is a flow chart of a method of assembling a medicament delivery device, according to an embodiment.
Figure 32A:
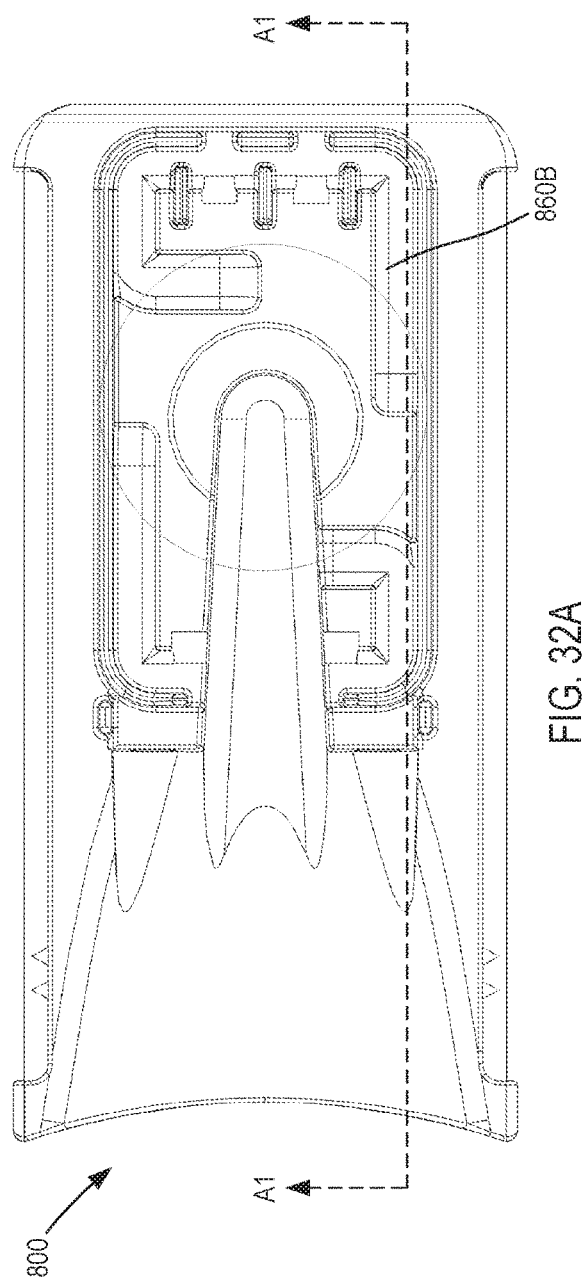
FIG. 32A is a top view of a medicament delivery device, according to an embodiment, in a closed configuration.
Figure 32B:
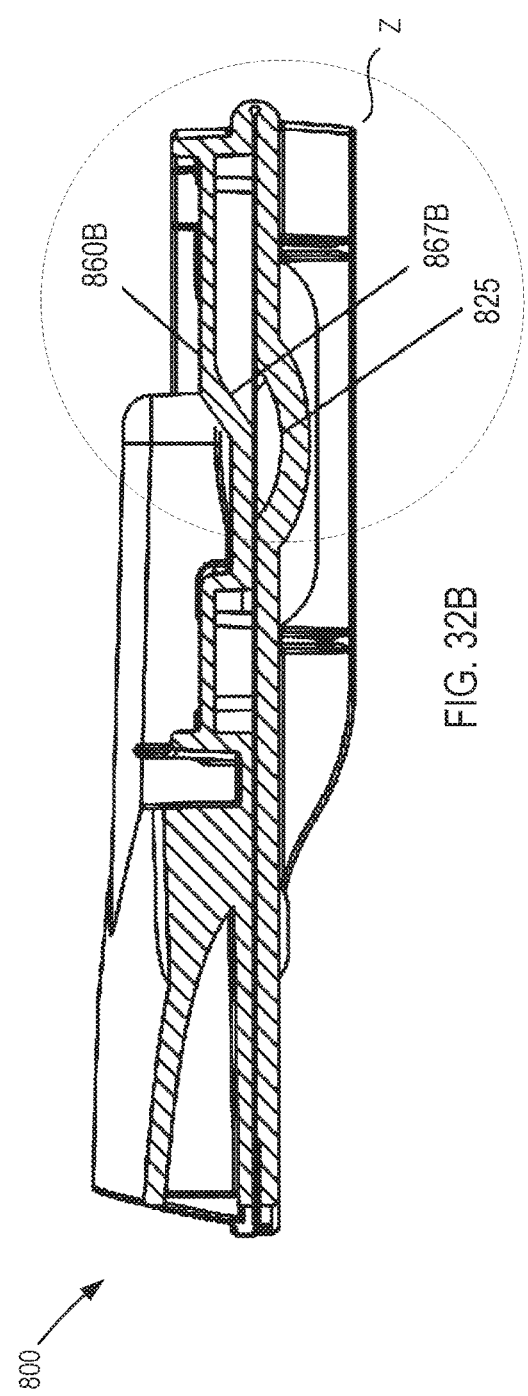
FIG. 32B is a cross-sectional view of the medicament delivery device shown in FIG. 32A taken along line A1-A1.
Figure 33:
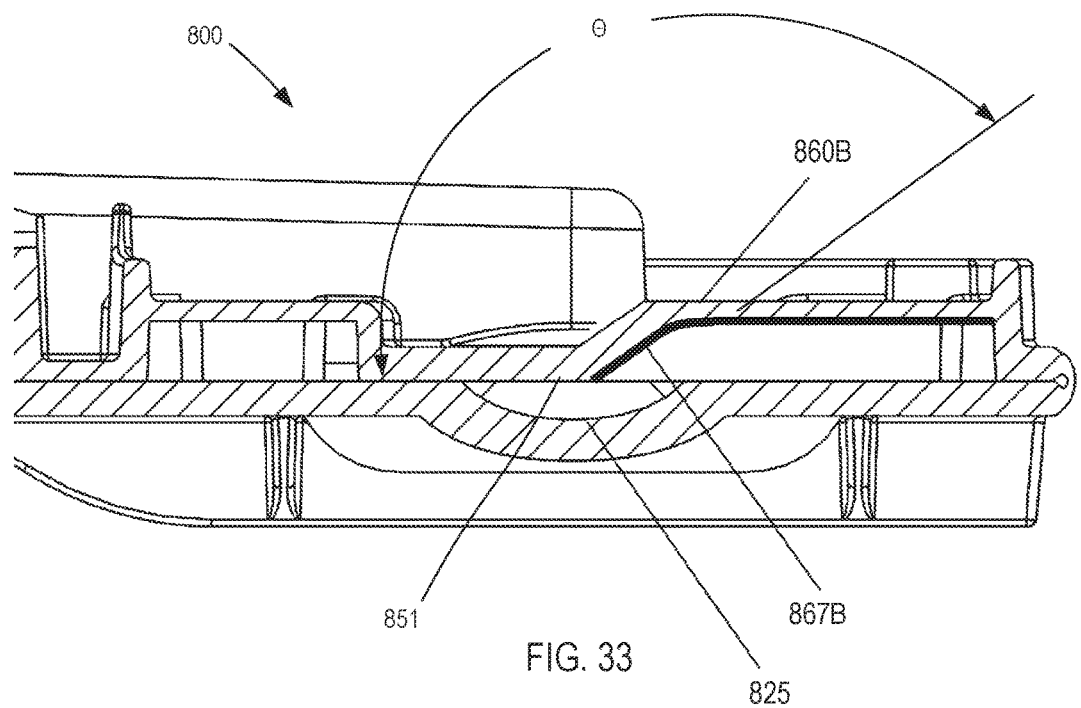
FIG. 33 is an enlarged view of a portion of the medicament delivery device shown in FIG. 32B identified by the region Z in FIG. 32B.
Figure 34:
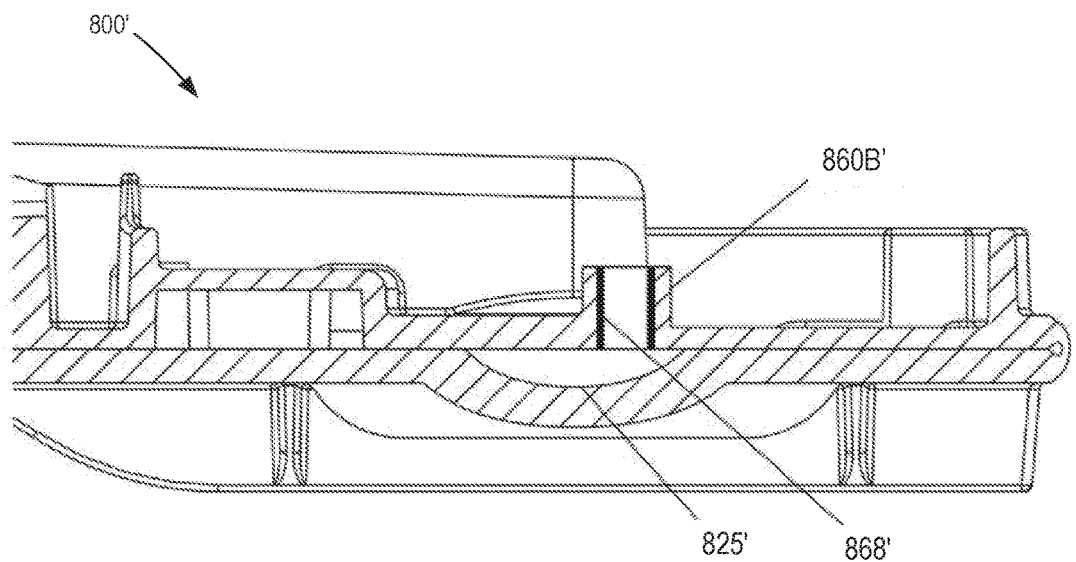
FIG. 34 is an enlarged cross-sectional view of a portion of a medicament delivery device, according to an embodiment, in a closed configuration.
Figure 35A:
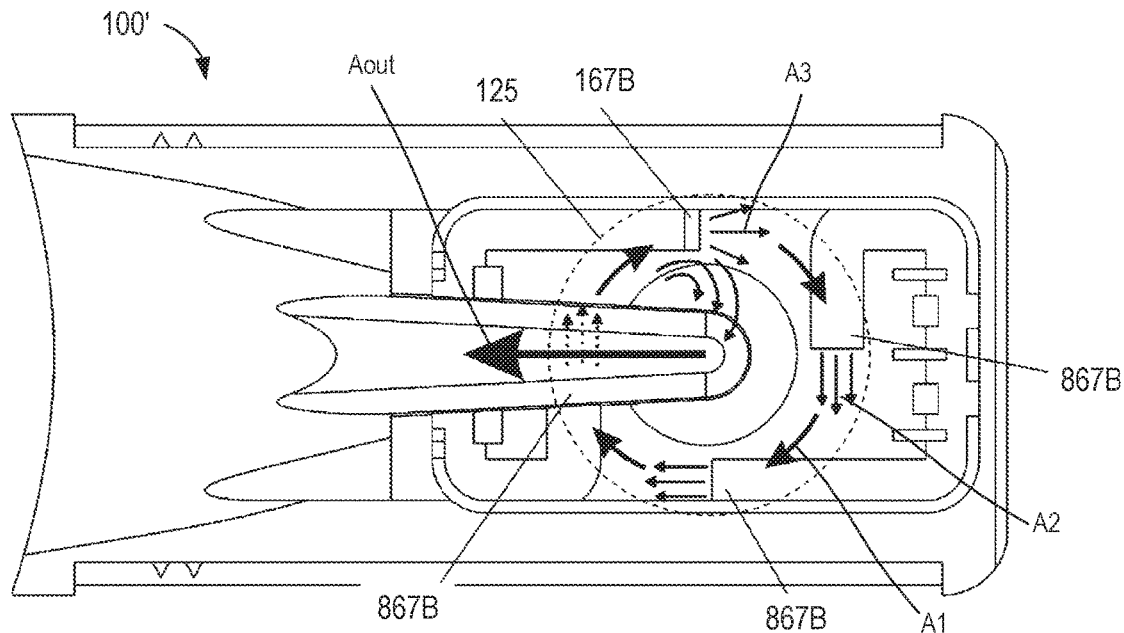
FIGS. 35A-35C are top views of various medicament delivery devices according to various embodiments, each having a different inlet air passageway geometry and flow characteristics.
Figure 35B:
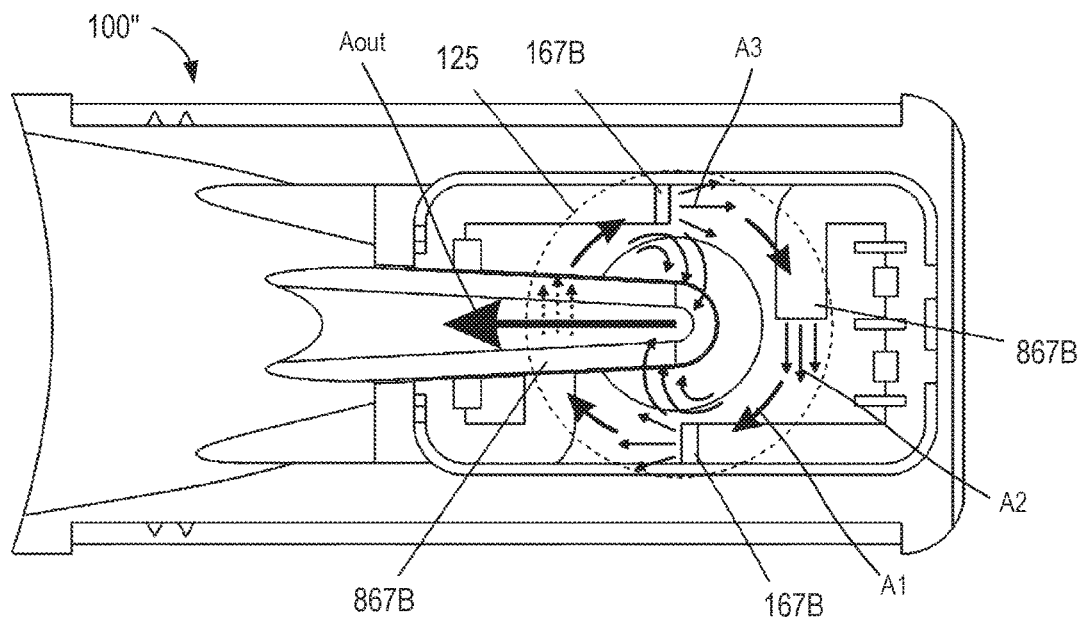
Figure 35C:
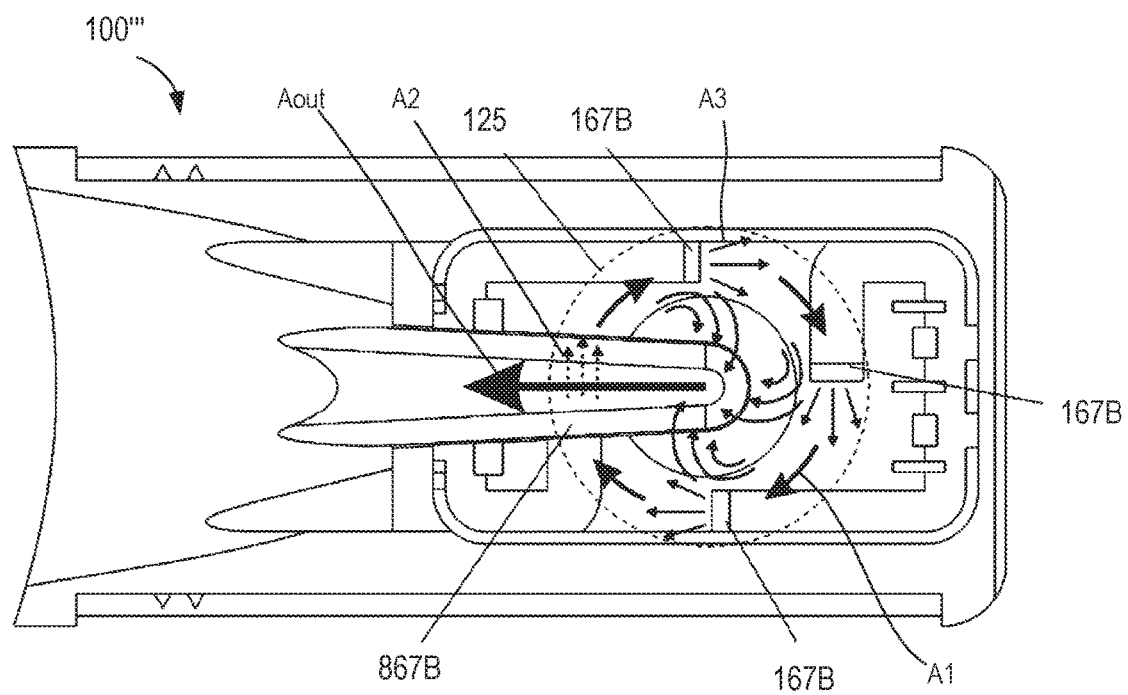
Figure 36:
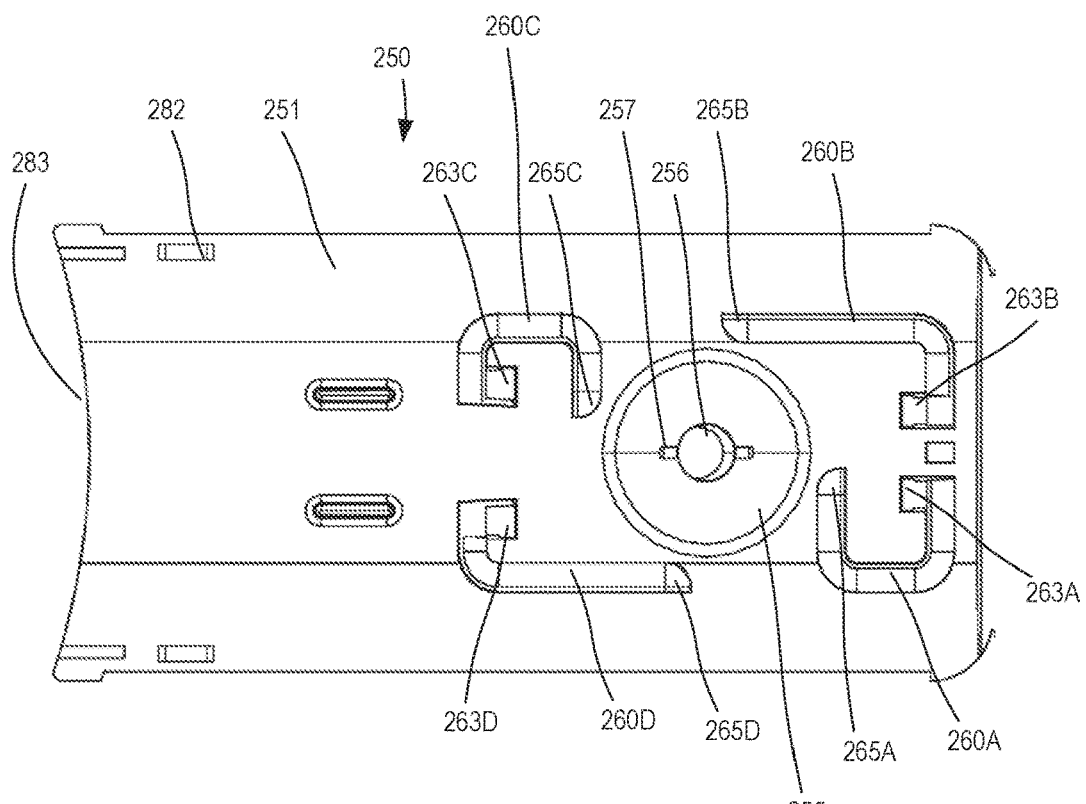
FIG. 36 is a top view of an upper portion of a medicament delivery device, according to an embodiment.

The medicament delivery device 100 (and any of the medicament delivery devices or drug products described herein) can be produced using any suitable method of assembly or manufacturing. For example, FIG. 31 is flow chart of a method 20 of assembling a dry powder inhaler, according to an embodiment. Although the method 20 is discussed with reference to FIGS. 18-23 (and the medicament delivery device 100 shown therein), in other embodiments the method 20 can be used to assembly any suitable device (drug product).

Figure 47:
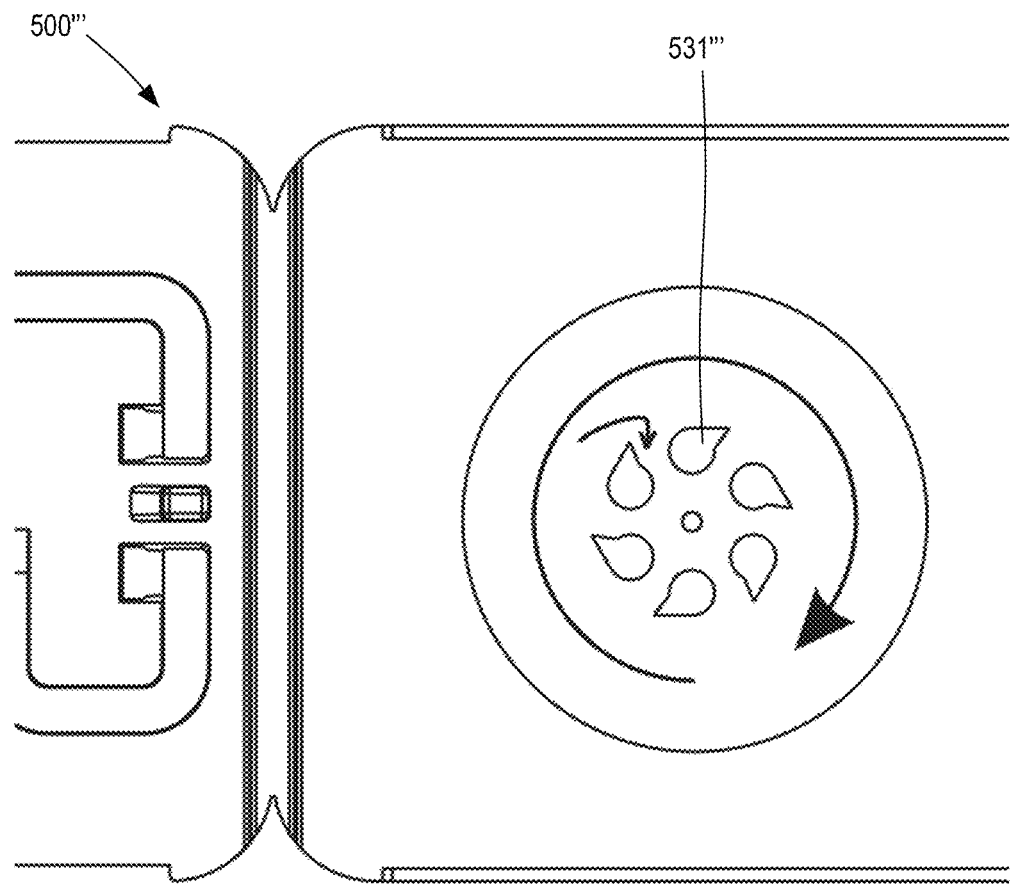
FIG. 47 is a top view of a portion of a medicament delivery device, according to an embodiment.
Figure 48:
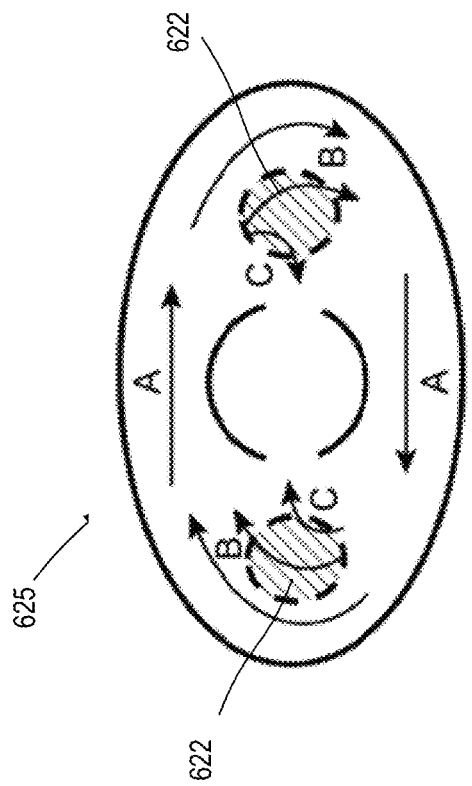
Figure 49:
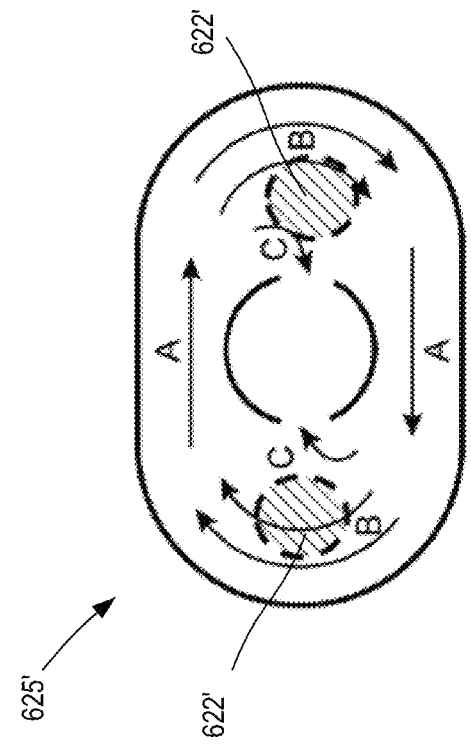

The method optionally includes opening a monolithically constructed device having a first member and a second member joined by a living hinge to expose a disaggregation chamber defined by the first member, at 21. The method includes conveying a dry powder into a portion of a disaggregation chamber defined by a first member of a medical device, at 22. Referring to FIG. 18, the dry powder is conveyed into the disaggregation chamber 125 when the device is in the opened configuration. The dry powder can be conveyed using any suitable method, such as, for example, drum filling or a dosator. In some embodiments, the dry powder can be conveyed using any of the methods or structure shown and described in U.S. Pat. No. 9,446,209, entitled "Dry Powder Inhalation Device," which is incorporated herein by reference in its entirety. In some embodiments, the dry powder can be in the form of a compressed plug of material. In such embodiments, the disaggregation chamber (or the first member 120) can include a target surface (or space) for placement of the compressed plug during the fill process. In addition to the open space shown within the disaggregation chamber 125 (see FIG. 13), alternative examples of target surfaces (or spaces) are shown in FIGS. 47-49 below. Such target surfaces can include an indentation, cut-out or other surface treatment to facilitate placing the dry powder in the desired location within the disaggregation chamber.

After the dry powder is in the disaggregation chamber, a strip (e.g., the strip 110) is coupled to an inner surface 121 of the first member 120 to seal the dry powder within the portion of the disaggregation chamber, at 24. The strip can be spot sealed to the inner surface 121, as shown in FIG. 19, to produce a seal around the disaggregation chamber 125. Referring to FIG. 20, the second member 150 of the medical device is then placed in contact with the first member 120 such that an inner surface 151 of the second member covers the portion of the disaggregation chamber 125, at 26. As shown, the second member defining an intake channel and an exit channel The exit channel is configured to be fluidically coupled to the disaggregation chamber via an exit opening defined by the inner surface of the second member. The intake channel is configured to be fluidically coupled to the disaggregation chamber via an intake port. As shown in FIG. 19, in some embodiments, the first member 120 and the second member 150 are monolithically constructed, and the second member 150 is placed about the first member 120 by bending a living hinge 138 between the first member and the second member.

The method 20 further includes deforming a flange (e.g., the flanges 144) extending from the inner surface of the first member to be matingly coupled to a joint surface (e.g., the joint surface 186) of the second member to form a sealed joint between the first member and the second member, at 28. In some embodiments, the flange can be deformed by heat swaging or heat staking the flange to bend the flange against the joint surface. Such methods of assembly can limit potential adverse effects on the powder that may results from high temperatures or other methods of joining (e.g., ultrasonic welding, radio frequency welding, or the like). Such methods are also easy to implement, thereby reducing the cost and complexity of producing the medical device. The heat swage joining method is beneficial for reducing air leakage variability at the inhaler joints without using ultrasonic welding which can be detrimental to the powder (high frequency vibration). Other joining methods such as snap fits require air gaps to reliably join given part tolerances, which leads to air leakage variability.

Referring to FIGS. 22 and 23, the heat swage flanges 144 are part of the lower portion of the inhaler and the mating joint surfaces 186 are located on the upper portion of the inhaler. FIG. 23 is a close up view of the top portion of the inhaler showing the flanges 144 in the deformed position to form the joint. As shown, in some embodiments, the upper portion 150 can include a set of triangular crush ribs 187 designed to block air flow leakage through the gap along the heat swage joint. In this manner, when a user inhales into the mouthpiece, and flow path along the exterior of the inhaler (e.g., caused by the gap along the joint) will be blocked by the crush ribs 187. This ensures that the full amount of inspiration is drawing through the mouthpiece, as intended.

Although the drug product 100 is shown as including a series of inlet passageways (e.g., inlet passageway 160A) that include curved exit ramp (e.g., the exit ramp 167A) into the chamber 125, in other embodiments, any of the devices and/or drug products described herein can have any suitable exit wall structure. For example, although the drug product 100 is shown as including a series of intake ports (e.g., intake port 165A and 165B) defined by a ramp that include vertical (or sharp) transition surfaces (e.g., the transition surfaces 168A, 168B) into the chamber 125, in other embodiments, any of the devices and/or drug products described herein can have an exit wall structure that gradually leads (or diffuses) into the chamber (e.g., the chamber 125 or any similar chambers described herein).

For example, FIGS. 32A, 32B, and 33 show a drug product (or medicament delivery device) 800, according to an embodiment. The drug product (or medicament delivery device) 800 is similar in many respects to the medicament delivery device 100 shown and described herein, and therefore certain portions of the device 800 are not described in great detail. As shown, the medicament delivery device 800 defines a series of air inlet passageways, including the air inlet passageway 860B. The device includes an intake ramp 867B that is a gradual transition into the chamber 825. As shown, the intake ramp 867B forms an exit angle Θ with respect to the surface 851 that is greater than 105 degrees. For example, in some embodiments, the exit angle Θ is about 135 degrees. Similarly stated, the intake ramp 867B causes the flow to turn about 45 degrees within the intake channel 860B. This arrangement produces less disruptive air jet(s) than those produced with the lower exit angle shown and described above with reference to the device 100. Thus, the higher exit angle reduces the amount of flow separation, which biases air/drug flow toward center outlet hole of the dose chamber 825 as flow re-circulates. FIG. 33 is a close-up view of FIG. 32B with the critical inlet air flow control surface 867 highlighted in bold line weight. Smooth transition air inlets can be beneficial for maximizing particle rotation, increasing dose release time and disaggregation of highly flowable powders.

As described herein, the dry powder P can also include any suitable excipient, such as, for example, lactose. The dry powder P can often include predominantly the excipient with a small percentage of the mass being the API (e.g., one to ten percent). Thus, the delivery characteristics of the device 600 can be highly dependent on the lactose characteristics (or the grade of lactose included within the dry powder P). For example, some dry powder P can include a non-sieved lactose with a mean diameter of 60 microns. Such powder formulations therefore include the fine lactose particles (e.g., 1-5 microns), and thus can be more "sticky" than those formulations that do not include as much of the fine particles. The advantage of using such non-sieved lactose is that a higher percentage of fine particles can be delivered, which can be beneficial for the desired treatment (e.g., deep lung delivery or the like). Such non-sieved formulations, however, can require more turbulent airflow to disaggregate the stickier fine particles than is needed for a sieved formulation. Thus, on some embodiments, however, the dry powder P can include a sieved lactose formulation having an initial mean particle diameter of 60 microns, but with a substantial amount of the fine particles removed by the sieve operation. Such embodiments, therefore, may not require the high amount of disruptive airflow delivered by some of the embodiments described herein. Thus, the higher exit angel (e.g., of greater about 135 degrees) can produce less turbulence and provide a suitable rotational flow for such a sieved formulation.

FIG. 34 shows a medicament delivery device 800', according to an embodiment. The drug product (or medicament delivery device) 800' is similar in many respects to the medicament delivery device 100 or 800 shown and described herein, and therefore certain portions of the device 800' are not described in great detail. As shown, the medicament delivery device 800' defines an air inlet passageway 860B' that includes a vertical channel (or side wall) 868' into the chamber 825'. The side wall 868' includes an abrupt sharp edge at the transition to the dose chamber 825' to disrupt rotational flow and fan-out flow to enable flow of particles to the air/drug exit opening to improve emitted dose percentage.

In some embodiments, any of the medicament delivery device (or drug products) described herein can have a combination of different inlet passageway geometries and/or different outlet geometries. For example, any of the embodiments described herein can have one or more inlet passageways defined by a vertical wall (as shown by the transition surface 168A described above), one or more inlet passageways defined by a gradual wall (as shown by the ramp 867B described above), and/or one or more inlet passageways defined by a cylindrical sharp wall (as shown by the wall 868'). This can allow the device to be tailored for a specific drug. Specifically, dry powder drug formulations can vary greatly in term of particle size, cohesiveness, surface attraction and flowability. To achieve the desired drug delivery performance (emitted dose and fine particle fraction) for a specific dry powder drug formulation, combinations of abrupt inlets such as vertical wall and smooth transition inlets (such as the 135-degree exit angle) may be integrated into the inhaler design. Using a four-inlet configuration as an example, FIGS. 35A-35C illustrate some of the possible combinations. In some embodiments, an inhaler design may include two or more air inlets with combinations of abrupt and smooth air inlets.

The medicament delivery devices 100', 100" and 100'" shown in FIGS. 35A-35C can be similar to the device 100 described above, but includes different intake ports. In referring to FIGS. 35A-35C, the arrows A1 represent the recirculating airflow within the disaggregation chamber, the arrows A2 represent straight inlet air produced by a ramp 867B, the arrows A3 represent the deflected (or fanned out) inlet air produced by a ramp 167B, and the arrow Aout represents the flow of air and drug out of the device. FIG. 35A shows a device 100' including one vertical wall air inlet (identified as a ramp 167B) and three smooth transition air inlets (identified as ramps 867B) into the chamber 125. FIG. 35B shows a device 100" including two vertical wall air inlets (identified as ramps 167B) and two smooth transition air inlets (identified as ramp 867B) into the chamber 125. FIG. 35C shows a device 100'" including three vertical wall air inlets (identified as ramps 167B) and one smooth transition air inlet into the chamber 125 (identified as a ramp 867B).

Although the inlet portion 153 is shown as including four inlet passageways 160A, 160B, 160C, 160D, in other embodiments, the device 100 (and any of the devices shown herein) can include any suitable number of inlet passageways. For example, in some embodiments, a device can include two inlet passageways, three inlet passageways, or even more than four inlet passageways. Moreover, although the inlet passageways 160A, 160B, 160C, 160D are shown as having a particular flow geometry, in other embodiments, a device can include any suitable flow geometry for any of the inlet passageways. For example, in some embodiments, a portion of an inlet passageway can include any suitable curves, radius, or edge designs to facilitate the desired entrainment, disaggregation, and/or production of the dry powder medicament therein.

For example, FIGS. 36 and 37 show a top view and a perspective view, respectively, of a portion of a medicament delivery device (or drug product) 200 according to an embodiment. The medicament delivery device 200 includes a lower member (or portion) 220 and an upper member (or portion) 250. FIG. 37 shows the lower member 220 and the upper member 250 in a substantially planar configuration to clearly show the features of each member. In use, the upper member 250 is coupled to the lower member 220 to form the assembled medicament delivery device 200. The medicament delivery device 200 is similar in many respects to the medicament delivery device 100 shown and described herein, and therefore certain portions of the device 200 are not described in great detail. For example, like the device 100, when assembled, the medicament delivery device 200 can be similar to, and can include certain features of, any of the medicament delivery devices shown and described in U.S. Pat. No. 9,446,209, entitled "Dry Powder Inhalation Device," which is incorporated herein by reference in its entirety.

The lower member 220 is similar to the lower member 120, and is therefore not described in great herein. Specifically, the lower member 220 defines a chamber 225 within which any suitable medicament is stored. In addition to providing a volume or reservoir within which a medicament can be stored, the chamber 225 also functions as a chamber (or a portion of a chamber) within which the medicament can be disaggregated or otherwise prepared for delivery to a patient. Specifically, the lower member 220 includes a raised central surface 226, an outer portion (or wall) 230, and an inner portion (or wall) 234. Together, these structures form a portion of (or define) the chamber 225. As described below, in use an inlet air flow can flow in a rotational (or swirling manner) within the chamber 225, bounded by the outer wall 230 and the inner wall 234. The chamber 225 can be configured such that, as the medicament is disaggregated into particles within the desired size range, the particles are entrained in the airflow and exit the chamber 225 via an exit opening 256 that is spaced apart from (and above) the raised surface 226.

The upper member 250 includes a first (or inner) surface 251 and a second (or outer) surface. The inner surface 251 defines a chamber 255 that, along with the chamber 225, forms a disaggregation chamber or volume, as described above. The upper member 250 includes an inlet portion 253 and an exit portion. The exit portion of the medicament delivery device 200 is similar to the exit portion 170 of the device 100 described above, and is therefore not shown or described herein.

The inlet portion 253 differs from the inlet portion 153 of the device 100 described above, in that the inlet portion 253 includes different shapes and geometries associated with the inlet passages. As described herein, the inlet portion 253 defines a series of inlet passageways through which inlet air flows into the disaggregation chamber when the patient inhales through the device 200. As described herein, the characteristics of the inlet air flow as it enters the chambers 225, 255 can impact the accuracy and repeatability with which the medicament within the chambers 225, 255 is disaggregated, broken up, and/or otherwise prepared for delivery to the patient. For example, the shape and size of the inlet passageways can influence the airflow pattern within the chamber 225. The angle of entry, in turn, can impact the number of revolutions that entrained particles make within the chamber 225 before exiting. Thus, the inlet portion 253 is configured to produce the desired inlet airflow such that the desired exit characteristics (e.g., velocity, flow rate, particle size distribution) are achieved.

In particular, the inlet portion 253 includes four inlet passageways: a first inlet passageway 260A, a second inlet passageway 260B, a third inlet passageway 260C, and a fourth inlet passageway 260D. Referring to FIG. 36, the first inlet passageway 260A includes an external opening 263A through which inlet air is drawn from outside of the device

200, and intake port 265A through which the inlet air is conveyed into the chambers 255, 225, and a curved portion therebetween. The second inlet passageway 260B includes an external opening 263B through which inlet air is drawn from outside of the device 200, and intake port 265B through which the inlet air is conveyed into the chambers 255, 225, and a curved portion therebetween. The third inlet passageway 260C includes an external opening 263C through which inlet air is drawn from outside of the device 200, and intake port 265C through which the inlet air is conveyed into the chambers 255, 225, and a curved portion therebetween. The fourth inlet passageway 260D includes an external opening 263D through which inlet air is drawn from outside of the device 200, and intake port 265D through which the inlet air is conveyed into the chambers 255, 225, and a curved portion therebetween.

Figure 37:
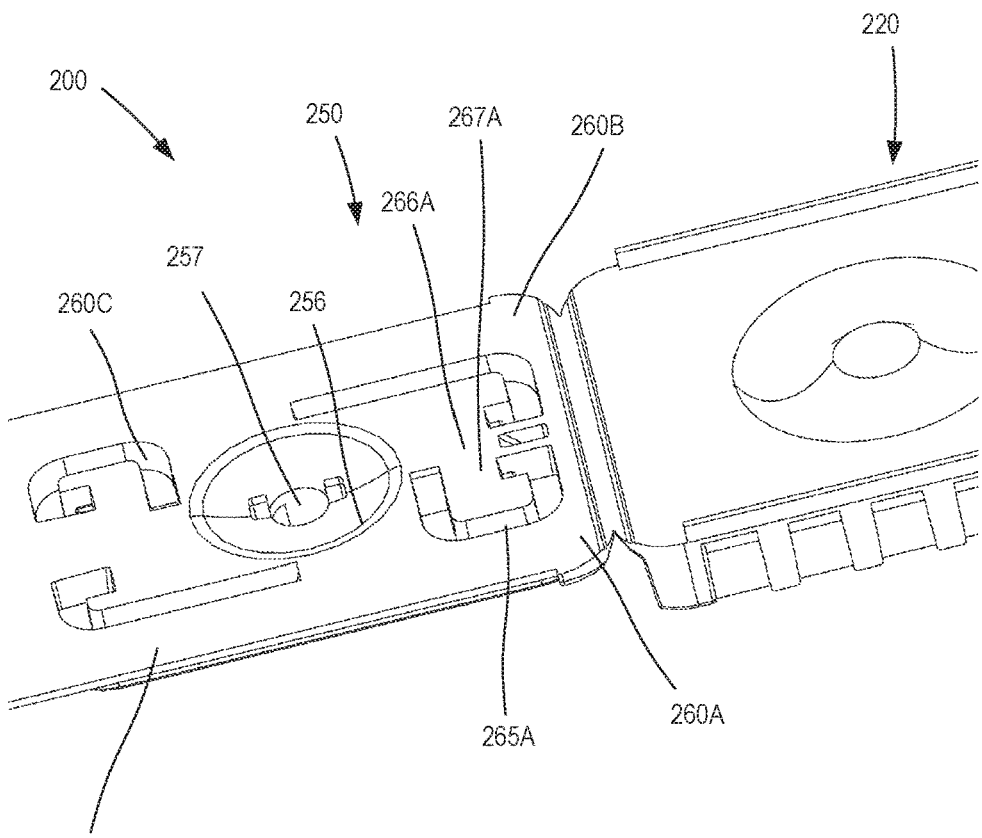
FIG. 37 is a perspective view of a portion of the medicament delivery device shown in FIG. 36.

The exit openings 265A, 265B, 265C, 265D are located on the inner surface 251 such that they open in to (or are in fluid communication with) the chamber 225 after the removal of any partition or seal that is disposed about the chamber 225. In this manner, upon inspiration (inhalation) by the patient, air is drawn from outside of the device through the external openings 263A, 263B, 263C, 263D, within the various curved portions of each of the inlet passageways, and into the chamber 225 via the intake ports 265A, 265B, 265C, 265D. As described above, the inlet passageways 260A, 260B, 260C, 260D can include any suitable geometry or size to produce the desired airflow characteristics within the chamber 225. For example, as shown in FIG. 37, the intake port 265A can be defined and/or bounded by a termination edge 266A and an exit ramp 267A. In contrast to the termination edge 166A (which is a linear edge), the termination edge 266A is a curved edge that intersects the chamber 225, and provides structure that directs the inlet air flow when exiting the inlet passageway 260A. Specifically, the termination edge 266A is formed by the intersection of the inner surface 251 and the side wall that defines a portion of the inlet passageway 260A.

The exit ramp 267A is the side wall that forms the end portion of the inlet passageway 260A and the boundary of a portion of the intake port 265A. The exit ramp 267A is a curved surface (i.e., a continuous, non-linear surface) that terminates, like the termination edge 266A, in a sharp edge. Unlike the termination edge 266A, however, the curved shape of the exit ramp 267A results in a more gradual (or smoother) exit from this portion of the intake port 265A. Although the termination edge 266A and the exit ramp 267A are described with respect to the intake port 265A, any of the exit openings described herein can include similar structure.

In some embodiments, the curved termination edge 266A and/or the curved exit ramp 267A can direct the inlet air flow entering the chamber 225 toward the outer portion (or wall) 230. Because the powder circulation is biased more toward the outer wall 230 of the dose chamber 225, the disaggregated particles within the airflow then flow through and around these biased air inlet jets prior to exiting the chamber 225 via the exit opening 256. This arrangement can cause a portion (similar to the second portion A2 shown in FIG. 5) of the inlet airflow to be conveyed outwardly towards the chamber wall 230. In this manner, the rotational flow within the disaggregation chamber 225 is biased towards and deflects off the outside portion of the disaggregation chamber 225, toward the exit opening 256. Similarly stated, the portion of the airflow can "bounce" off the outer portion of the wall 230 and be conveyed through the primary circulating airflow (similar to the first portion A1 shown in FIG. 5) and toward the exit opening 726. Thus, the particles circulating within the primary airflow will flow through (and be disrupted by) a portion of the inlet airflow. In this manner, the flow pattern of the inlet air entering the chamber 225 can affect the delivery of the disaggregated medicament. In some embodiments, for example, this arrangement can be advantageous for the delivery of cohesive powders with poor flowability. Similarly stated, this arrangement can help "speed up drug release to the patient, for example, by forcing the powder medicament to exit the device 200 in a shorter period of time. For example, if the patient inhales for four seconds, it may be desirable to release the powder over a two second period of time, rather than a 4 second delivery time. Releasing the powder medicament at a faster rate means fast and efficient powder clearance from the dose chamber, and therefore potentially results in higher emitted dose percentage and more consistent dosing (dose-to-dose uniformity). By delivering a consistent dose with adequate particle size distribution, the drug product can be tailored to match marketed drug products. For example, in some embodiments, the drug product 200 (or any other drug products described herein) can produce a particle size distribution well suited for reaching the deeper areas (e.g., alveoli) of the lungs.

Figure 38:
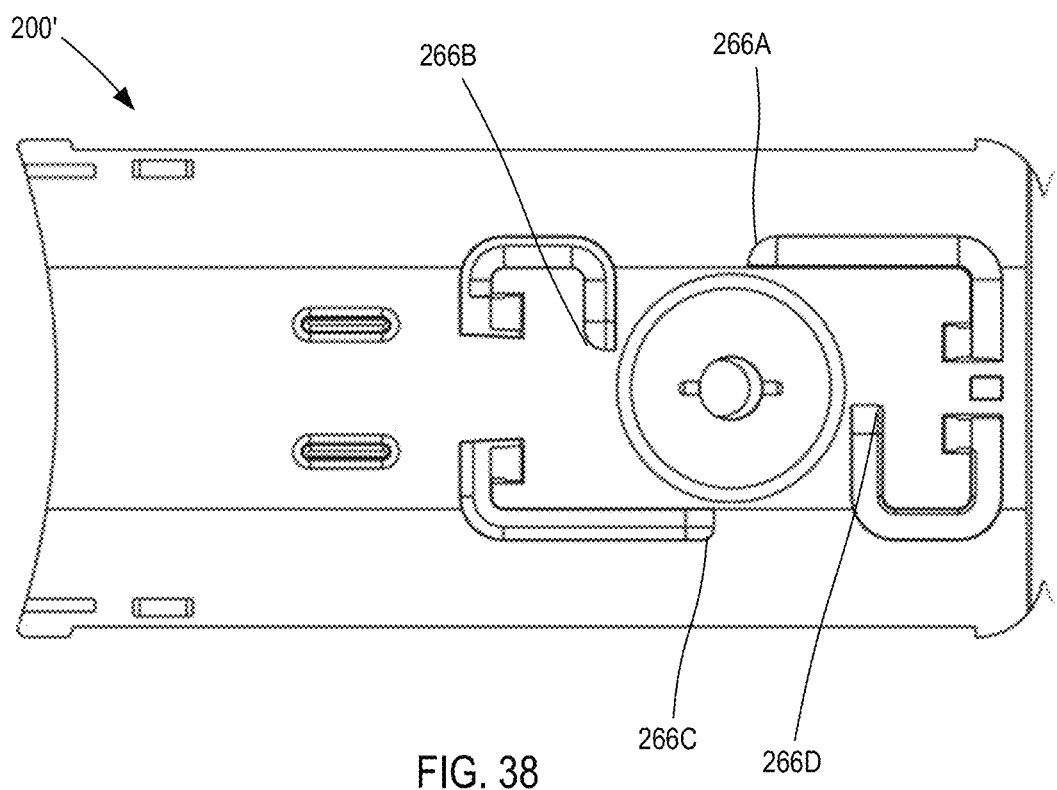
FIG. 38 is a bottom view of an upper portion of a medicament delivery device, according to an embodiment.

FIG. 38 depicts an inhaler 200' with 'outside radius air inlets' having different sizes. Specifically, the inhaler includes radiused termination edges 266A, 266B, 266C and 266D that are radiused or ramped air inlets of variable size to guide powder more directly to the outlet in a swirl flow pattern.

Although shown as being circular in shape, in other embodiments, the chamber 125 (or any of the dose or disaggregation chambers described herein) can have any suitable shape and/or can include any suitable flow structures therein to promote the desired preparation of the medicament for delivery via inhalation.

Figure 39:
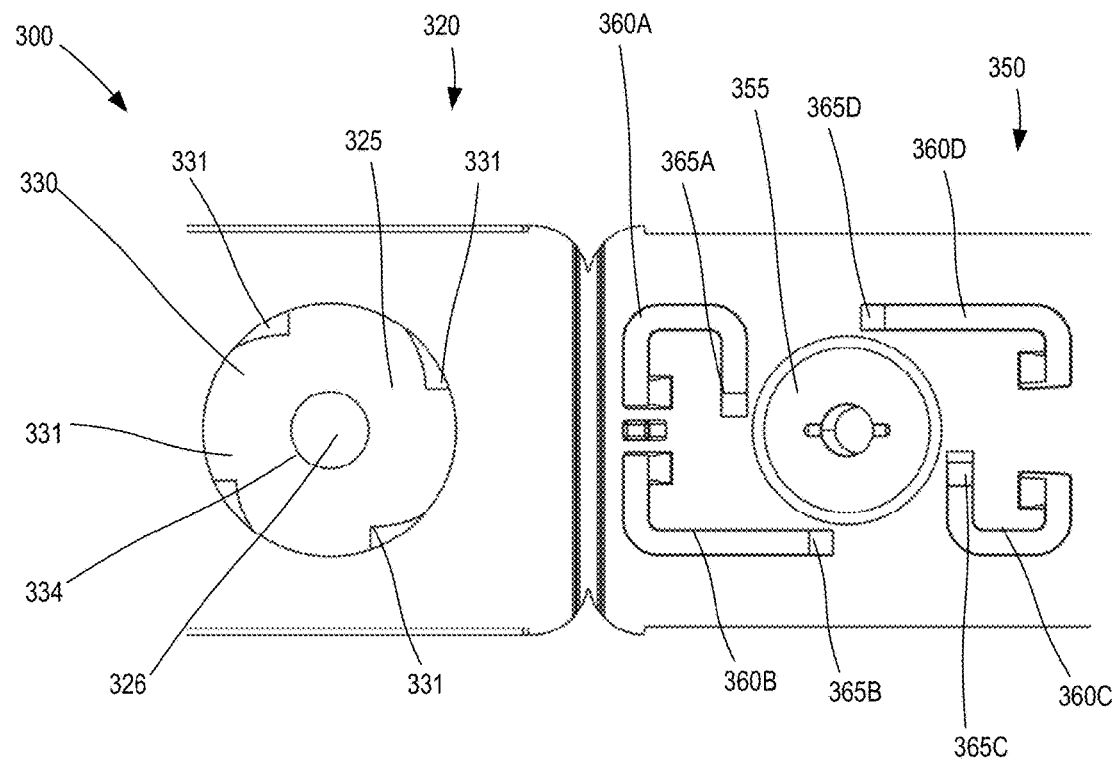
FIG. 39 is a top view of a portion of a medicament delivery device in an opened configuration, according to an embodiment.
Figure 40:
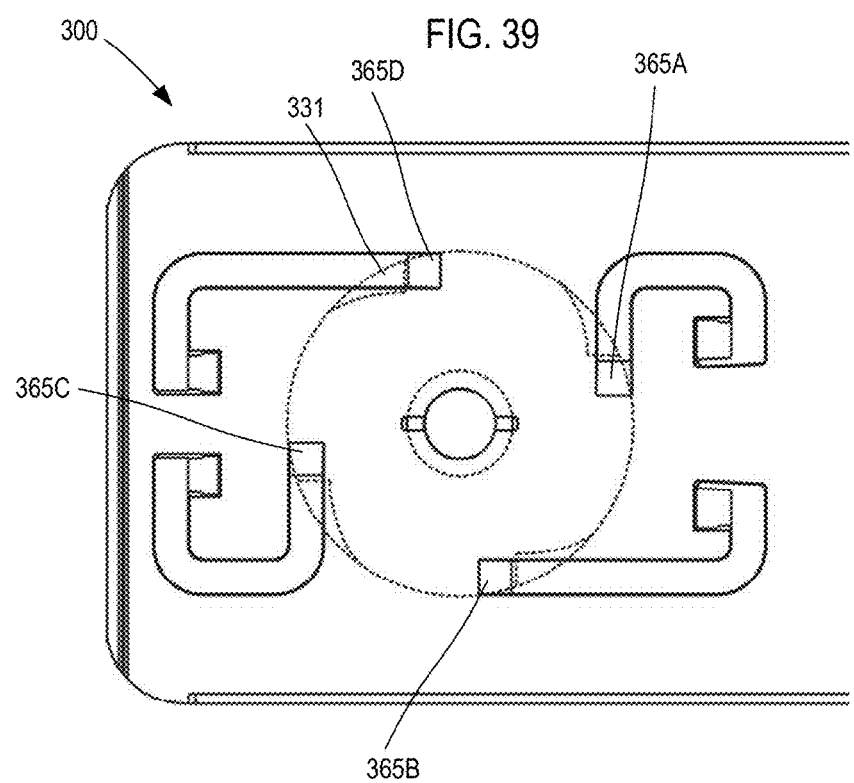
FIG. 40 is a top view of a portion of the medicament delivery device shown in FIG. 39 in a closed configuration.

For example, FIGS. 39 and 40 are top views of a portion of a medicament delivery device (or drug product) 300 according to an embodiment. FIG. 39 shows the device 300 in an opened configuration and FIG. 40 shows the device in a closed configuration. The medicament delivery device 300 includes a lower member (or portion) 320 and an upper member (or portion) 350. FIG. 39 shows the lower member 320 and the upper member 350 in a substantially planar configuration to clearly show the features of each member. In use, however, the upper member 350 is coupled to the lower member 320 to form the assembled medicament delivery device 300, as shown in FIG. 40. The medicament delivery device 300 is similar in many respects to the medicament delivery device 100 and/or the medicament delivery device 200 shown and described herein, and therefore certain portions of the device 300 are not described in great detail. For example, like the devices 100, 200, when assembled, the medicament delivery device 300 can be similar to, and can include certain features of, any of the medicament delivery devices shown and described in U.S. Pat. No. 9,446,209, entitled "Dry Powder Inhalation Device," which is incorporated herein by reference in its entirety.

The upper member 350 is similar to the upper member 150 shown and described above. Specifically, the upper member 350 defines a chamber 355 that, along with the chamber 325, forms a disaggregation chamber or volume, as described above. The upper member 350 includes an inlet portion 353 that includes four inlet passageways: a first inlet passageway 360A, a second inlet passageway 360B, a third inlet passageway 360C, and a fourth inlet passageway 360D. The first inlet passageway 360A includes an external opening through which inlet air is drawn from outside of the device 300, and an intake port 365A through which the inlet air is conveyed into the chambers 355, 325. The second inlet passageway 360B includes an external opening through which inlet air is drawn from outside of the device 300, and an intake port 365B through which the inlet air is conveyed into the chambers 355, 325. The third inlet passageway 360C includes an external opening through which inlet air is drawn from outside of the device 300, and an intake port 365C through which the inlet air is conveyed into the chambers 355, 325. The fourth inlet passageway 360D includes an external opening through which inlet air is drawn from outside of the device 300, and an intake port 365D through which the inlet air is conveyed into the chambers 355, 325.

The intake ports 365A, 365B, 365C, 365D are located such that they open in to (or are in fluid communication with) the chamber 325 after the removal of any partition or seal that is disposed about the chamber 325. The intake ports 365A, 365B, 365C, 365D are shown on the lower member 320 to identify their location when the device 300 is in the assembled configuration. In this manner, upon inspiration (inhalation) by the patient, air is drawn from outside of the device through the external openings, within the various curved portions of each of the inlet passageways, and into the chamber 325 via the intake ports 365A, 365B, 365C, 365D. As described above, the inlet passageways 360A, 360B, 360C, 360D can include any suitable geometry or size to produce the desired airflow characteristics within the chamber 325.

The lower member 320 defines a chamber 325 within which any suitable medicament is stored. In addition to providing a volume or reservoir within which a medicament can be stored, the chamber 325 also functions as a chamber (or a portion of a chamber) within which the medicament can be disaggregated or otherwise prepared for delivery to a patient. Specifically, the lower member 320 includes a raised central surface 326, an outer portion (or wall) 330, and an inner portion (or wall) 334. Together, these structures form a portion of (or define) the chamber 325.

The lower member 320 differs from the lower member 120 in that the lower member 320 includes a series of ramps 331. Each ramp 331 is located adjacent to the region at which the inlet air flow is conveyed from the intake ports 365A, 365B, 365C, 365D into the chamber 325. In this manner, the ramps 331 can obstruct any "dead zones" or low flow velocity eddy currents within the chamber 325, thereby promoting improved mixing, flow properties and more complete dose delivery from the disaggregation chamber. Similarly stated, the ramps 331 can direct the flow from one intake port (e.g., intake port 365A) away from (or out of the path from) an adjacent intake port (e.g., intake port 365B) and toward center to assist clearance of particles from the disaggregation chamber (flow to outlet opening).

Figure 41:
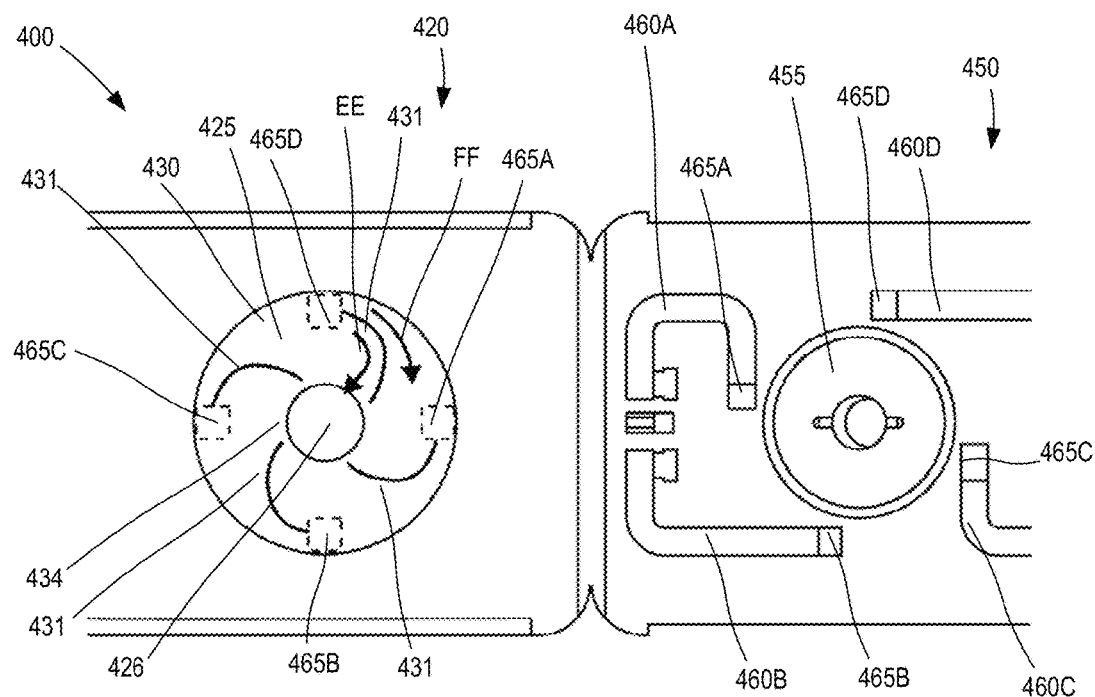
FIG. 41 is a top view of a portion of a medicament delivery device, according to an embodiment.
Figure 42:
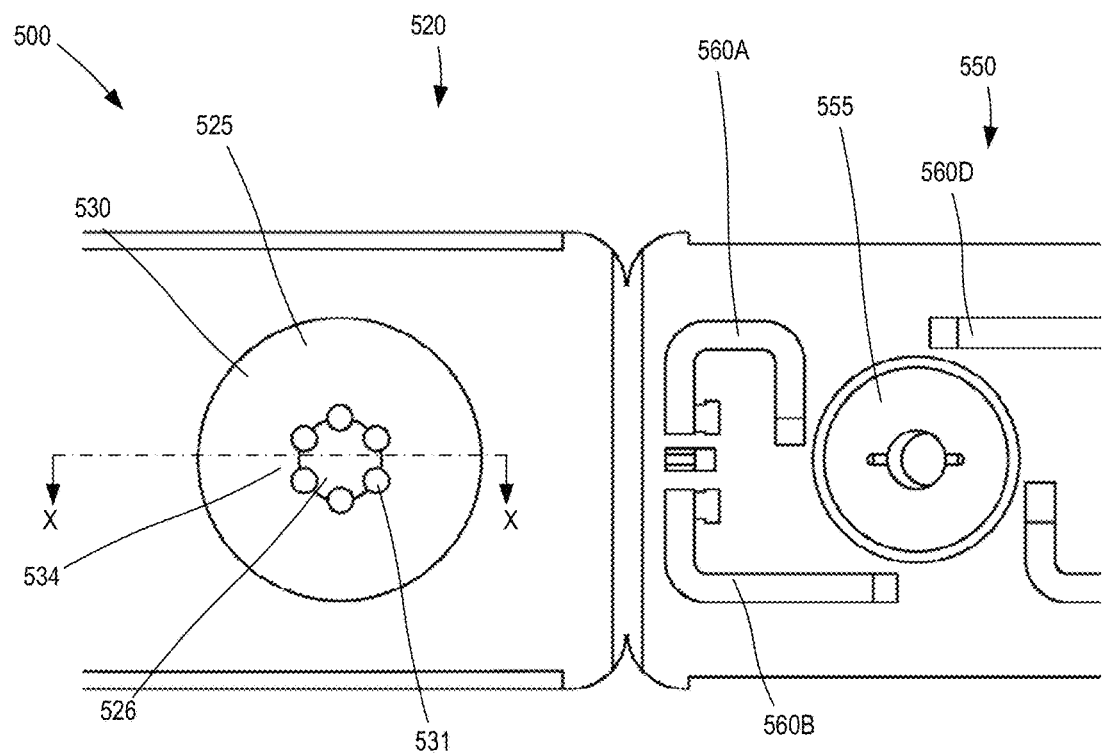
FIG. 42 is a top view of a portion of a medicament delivery device, according to an embodiment.
Figure 43:
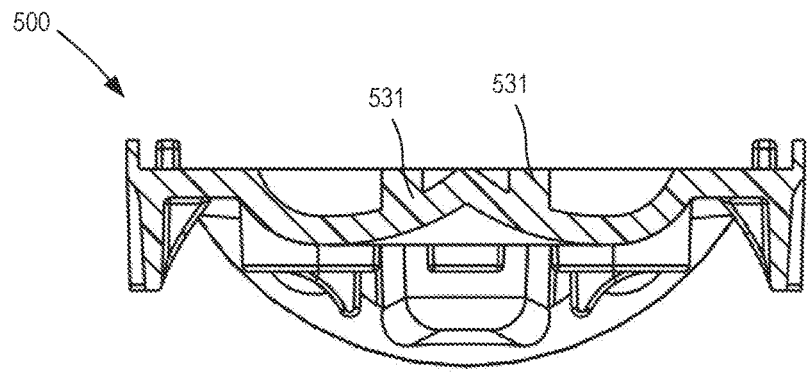
FIG. 43 is a cross-sectional side view of a portion of the medicament delivery device shown in FIG. 42, taken along line X-X.
Figure 44:
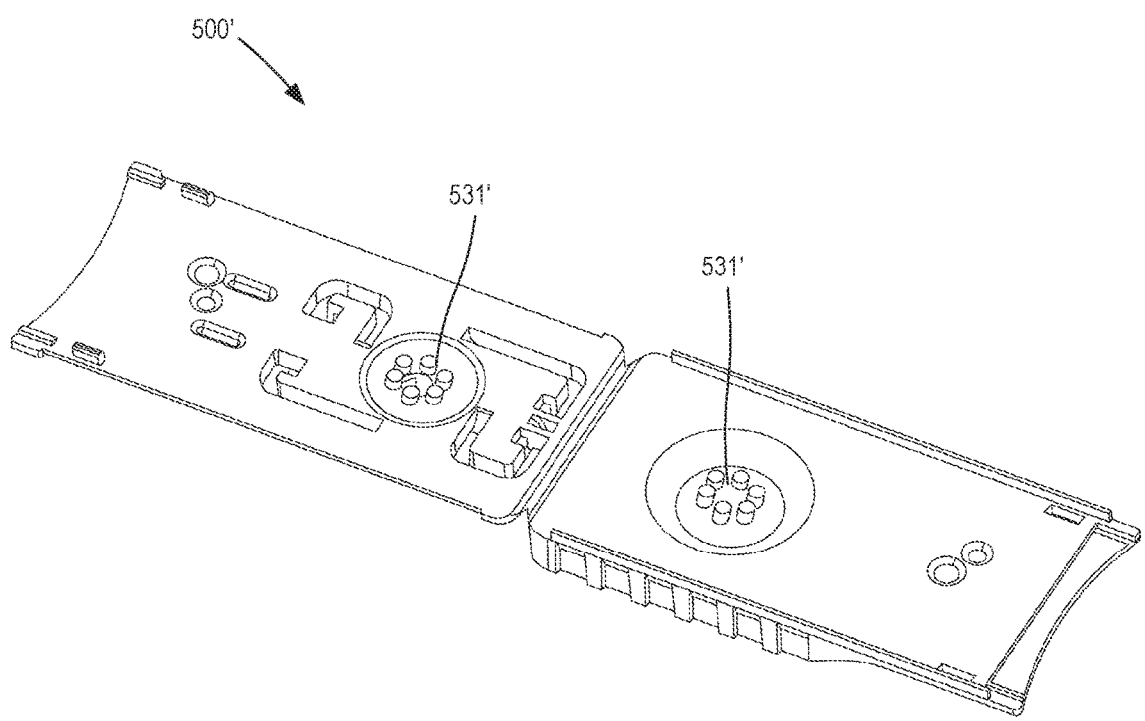
FIG. 44 is a perspective view of a portion of a medicament delivery device, according to an embodiment.
Figure 45:
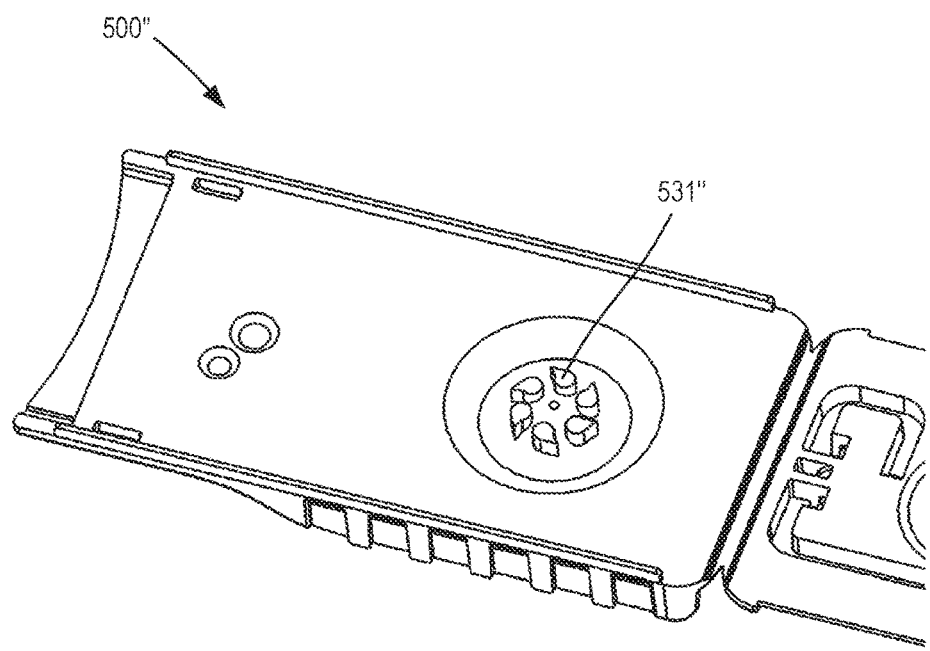
FIGS. 45 and 46 are a perspective view and a top view, respectively, of a portion of a medicament delivery device, according to an embodiment.
Figure 46:
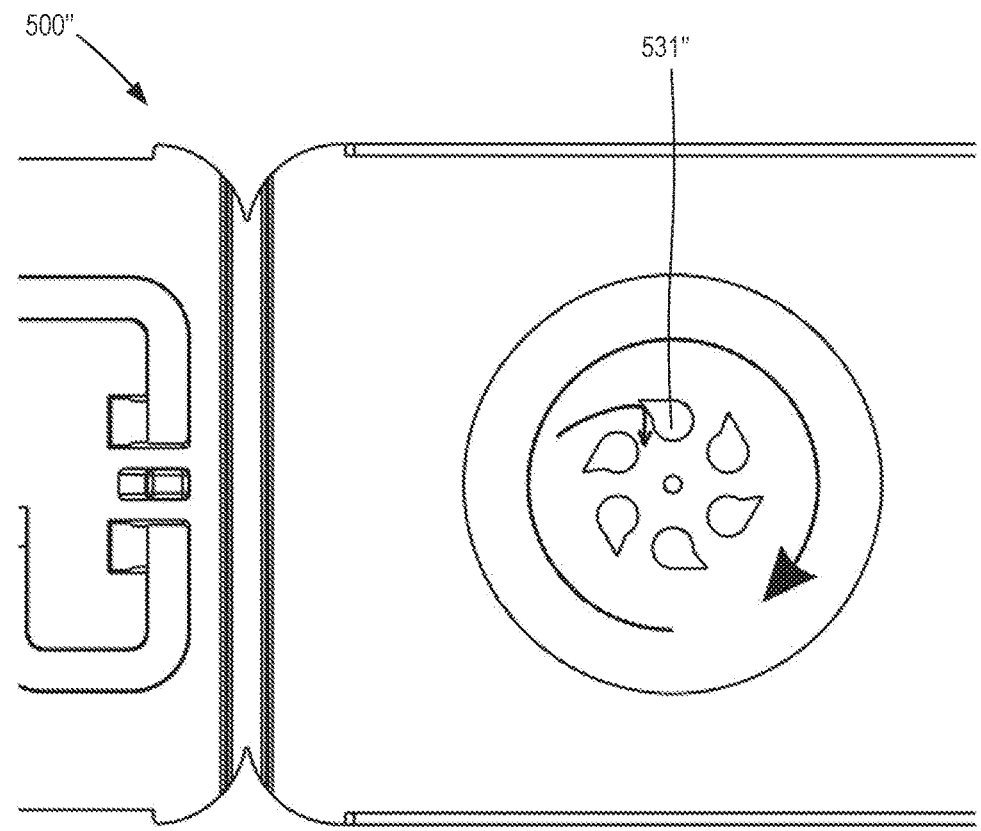

FIG. 41 is a top view of a portion of a medicament delivery device (or drug product) 400 according to an embodiment. The medicament delivery device 400 includes a lower member (or portion) 420 and an upper member (or portion) 450. FIG. 41 shows the lower member 420 and the upper member 450 in a substantially planar configuration to clearly show the features of each member. In use, however, the upper member 450 is coupled to the lower member 420 to form the assembled medicament delivery device 400. The medicament delivery device 400 is similar in many respects to the medicament delivery device 100 and/or the medicament delivery device 200 shown and described herein, and therefore certain portions of the device 400 are not described in great detail. For example, like the devices 100, 200, when assembled, the medicament delivery device 400 can be similar to, and can include certain features of, any of the medicament delivery devices shown and described in U.S. Pat. No. 9,446,209, entitled "Dry Powder Inhalation Device," which is incorporated herein by reference in its entirety.

The upper member 450 is similar to the upper member 150 shown and described above. Specifically, the upper member 450 defines a chamber 455 that, along with the chamber 425, forms a disaggregation chamber or volume, as described above. The upper member 450 includes an inlet portion 453 that includes four inlet passageways: a first inlet passageway 460A, a second inlet passageway 460B, a third inlet passageway 460C, and a fourth inlet passageway 460D. The first inlet passageway 460A includes an external opening through which inlet air is drawn from outside of the device 400, and intake port 465A through which the inlet air is conveyed into the chambers 455, 425. The second inlet passageway 460B includes an external opening through which inlet air is drawn from outside of the device 400, and intake port 465B through which the inlet air is conveyed into the chambers 455, 425. The third inlet passageway 460C includes an external opening through which inlet air is drawn from outside of the device 400, and intake port 465C through which the inlet air is conveyed into the chambers 455, 425. The fourth inlet passageway 460D includes an external opening through which inlet air is drawn from outside of the device 400, and intake port 465D through which the inlet air is conveyed into the chambers 455, 425.

The intake ports 465A, 465B, 465C, 465D are located such that they open in to (or are in fluid communication with) the chamber 425 after the removal of any partition or seal that is disposed about the chamber 425. The intake ports 465A, 465B, 465C, 465D are shown on the lower member 420 to identify their location when the device 400 is in the assembled configuration. In this manner, upon inspiration (inhalation) by the patient, air is drawn from outside of the device through the external openings, within the various curved portions of each of the inlet passageways, and into the chamber 425 via the intake ports 465A, 465B, 465C, 465D. As described above, the inlet passageways 460A, 460B, 460C, 460D can include any suitable geometry or size to produce the desired airflow characteristics within the chamber 425.

The lower member 420 defines a chamber 425 within which any suitable medicament is stored. In addition to providing a volume or reservoir within which a medicament can be stored, the chamber 425 also functions as a chamber (or a portion of a chamber) within which the medicament can be disaggregated or otherwise prepared for delivery to a patient. Specifically, the lower member 420 includes a raised central surface 426, an outer portion (or wall) 430, and an inner portion (or wall) 434. Together, these structures form a portion of (or define) the chamber 425.

The lower member 420 also includes a series of vanes (also referred to as ridges or partitions) 431. Each vane 431 is located adjacent to the region at which the inlet air flow is conveyed from the intake ports 465A, 465B, 465C, 465D into the chamber 425. In this manner, the vanes 431 can direct the flow entering the chamber 425, thereby promoting improved mixing, flow properties and more complete dose delivery from the disaggregation chamber. Specifically, the vanes 431 can divide each jet of inlet air into a first portion that is directed towards inner wall 434 (see the arrow EE) to assist in clearance of particles from the disaggregation chamber (flow to outlet hole) and a second portion that is directed towards outer wall promote disaggregation of particles 430 (see the arrow FF).

Although the device 100 is shown as including two protrusions 157 that contact the raised surface 126, in other embodiments, a device can include any suitable type of flow structures, stiffeners or the like in the region surrounding the exit opening and/or the raised surface. For example, FIG. 42 is a top view of a portion of a medicament delivery device (or drug product) 500 according to an embodiment. The medicament delivery device 500 includes a lower member (or portion) 520 and an upper member (or portion) 550. FIG. 42 shows the lower member 520 and the upper member 550 in a substantially planar configuration to clearly show the features of each member. In use, however, the upper member 550 is coupled to the lower member 520 to form the assembled medicament delivery device 500. The medicament delivery device 500 is similar in many respects to the medicament delivery device 100 and/or the medicament delivery device 200 shown and described herein, and therefore certain portions of the device 500 are not described in great detail. For example, like the devices 100, 200, when assembled, the medicament delivery device 500 can be similar to, and can include certain features of, any of the medicament delivery devices shown and described in U.S. Pat. No. 9,446,209, entitled "Dry Powder Inhalation Device," which is incorporated herein by reference in its entirety.

The upper member 550 is similar to the upper member 150 shown and described above. Specifically, the upper member 550 defines a chamber 555 that, along with the chamber 525, forms a disaggregation chamber or volume, as described above. The upper member 550 includes an inlet portion that includes four inlet passageways: a first inlet passageway 560A, a second inlet passageway 560B, a third inlet passageway (not shown), and a fourth inlet passageway 560D.

The exit openings of the inlet passageways are located such that they open in to (or are in fluid communication with) the chamber 525 after the removal of any partition or seal that is disposed about the chamber 525. In this manner, upon inspiration (inhalation) by the patient, air is drawn from outside of the device through the external openings, within the various curved portions of each of the inlet passageways, and into the chamber 525, as described above.

The lower member 520 defines a chamber 525 within which any suitable medicament is stored. In addition to providing a volume or reservoir within which a medicament can be stored, the chamber 525 also functions as a chamber (or a portion of a chamber) within which the medicament can be disaggregated or otherwise prepared for delivery to a patient. Specifically, the lower member 520 includes a raised central surface 526, an outer portion (or wall) 530, and an inner portion (or wall) 534. Together, these structures form a portion of (or define) the chamber 525.

The lower member 520 also includes a series of protrusion (also referred to as posts) 531 (only one of the six protrusions is labeled). The protrusions 531 are located surrounding the raised central surface 526. Specifically, FIG. 43 shows a side view showing the protrusions. In this manner, the protrusions 531 can direct the flow exiting the chamber 525, thereby promoting improved mixing and flow properties. Specifically, the protrusions 531 can control the exit flow rate of the medicament by deflecting outgoing particles, enhance the deflection of the dry powder (to improve disaggregation) and/or produce more rotation or flow eddies (to improve disaggregation).

Although the protrusions 531 are shown as being on the lower member, in other embodiments, the protrusions can be on either, the lower member, the upper member, or both. For example, FIG. 44 shows a device 500' including protrusions 531' on both the lower member and the upper member.

Although shown as having a circular cross-sectional shape, in other embodiments, the protrusions 531 can have any suitable shape. For example, in some embodiments, the protrusions 531 can be rectangular, octagonal, or any other suitable polygon shape. For example, FIGS. 45 and 46 show a device 500" including protrusions 531" having a teardrop shape with flat powder control surface. FIG. 47 shows a device 500''' including protrusions 531''' having a modified teardrop shape to deflect the flow inward in a different manner Moreover, although the raised central surface 126 is shown as being substantially flat (or planar), in other embodiments, the raised central surface of any embodiments described herein can have any suitable shape. For example, the raised central surface 526 can be a convex shape, a concave shape, a spherical shape, or the like.

Although the chamber 125 and the chamber 155 are each shown and described has having circular cross-sectional shape, in other embodiments, any of the chambers described herein can have any suitable shape. For example, FIGS. 48-50 show schematic illustrations of chambers having non-circular cross-sectional shapes with constriction and expansion areas for rotational flow, and outlets located to pick up fine particles. Specifically, FIG. 48 shows a chamber 625 having target locations 622 and FIG. 49 shows a chamber 625' having target locations 622'. FIG. 50 shows a chamber 625" having a single target location 622". As described above, the target locations are areas of the chamber that can receive a compressed plug of dry powder. The arrows represent various flow patterns that are facilitated by and/or produced within the chambers.

Although the device 700 and the device 200 are shown and described as including an intake ramp (e.g., the ramp 767 and the ramp 267A) that include a curved surface, in other embodiments, a device can include an intake ramp that includes multiple curved surfaces. For example, FIG. 51 is a schematic illustration of a medicament delivery device (or drug product) 700' according to an embodiment. The medicament delivery device 700' is similar to the medicament delivery device (or drug product) 700 described above, and is therefore not described in detail herein. Specifically, the device 700' includes an intake channel 760' that is configured to be fluidically coupled to the disaggregation chamber 725' via an intake port 765'. The intake port 765' is defined at least in part by an intake ramp 767' that is curved both outwardly towards the chamber wall and inwardly towards the exit opening. This arrangement creates and narrow tipped opening at the inlet/chamber transition to "nozzle" the inlet flow (i.e., to produce a higher velocity in the inlet flow) downward to disrupt the rotational flow and deflect powder P toward the exit opening 756', as shown by the arrows.

Any of the medicament delivery devices (drug products) described herein can be included within any suitable packaging. For example, FIG. 50 depicts a packaging assembly that contains an inhaler 707 therein. The inhaler 707 can be similar to any of the devices shown and described herein, such as the medicament delivery device 100, and includes an activation trip (pull tab) 708 sealed inside a protective overwrap 711 for protection from ultraviolet light and moisture. The overwrap 711 is heat sealed 709 on all sides and includes a slit 710 for easy opening. In some embodiments, the overwrap can be injected and sealed with an inert gas to ensure that the powder (e.g., drug, nutraceuticals) contained in the inhaler 707 is not stored in an environment including oxygen.

Figure 50:
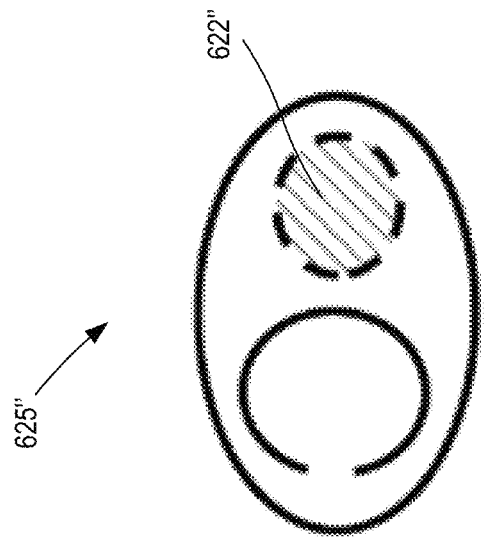
FIGS. 48-50 are schematic illustrations of a disaggregation chamber of a medicament delivery device, according to an embodiment.
Figure 51:
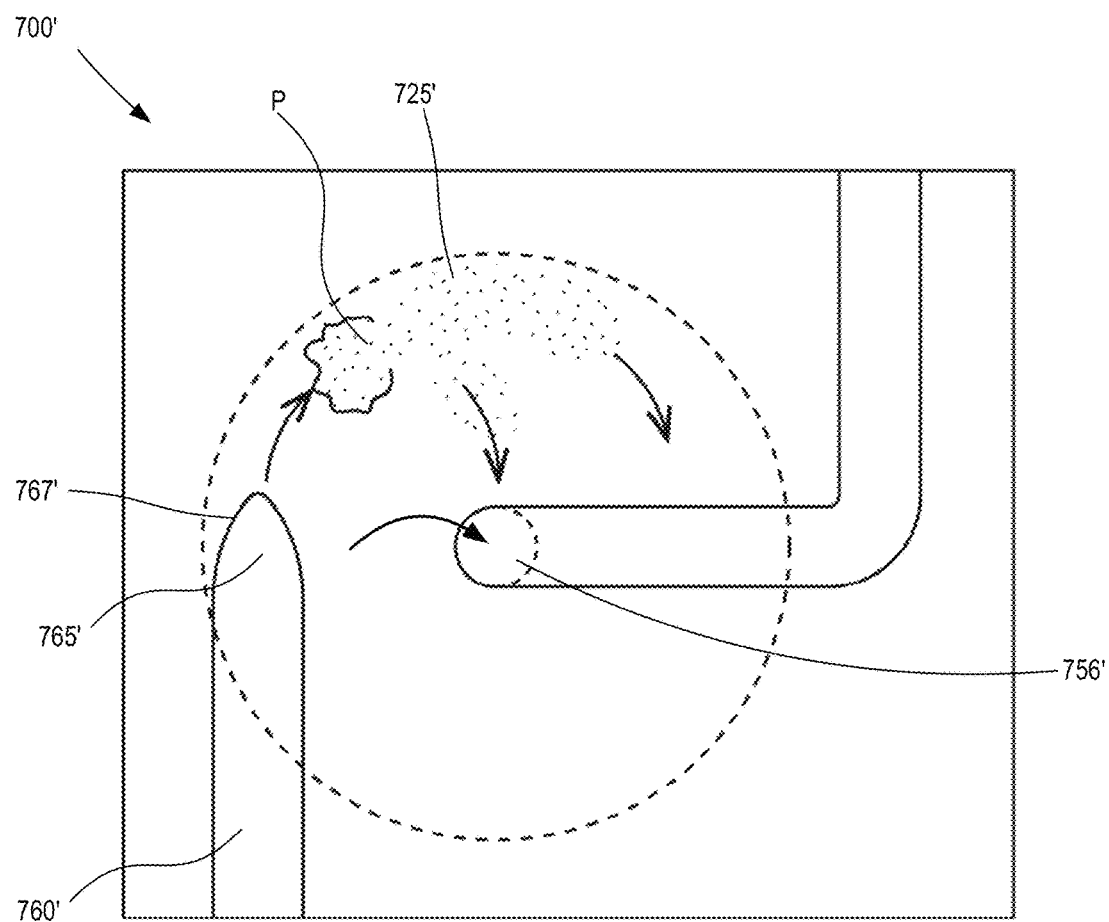
FIG. 51 is a schematic illustration of a disaggregation chamber of a medicament delivery device, according to an embodiment.
Figure 52:
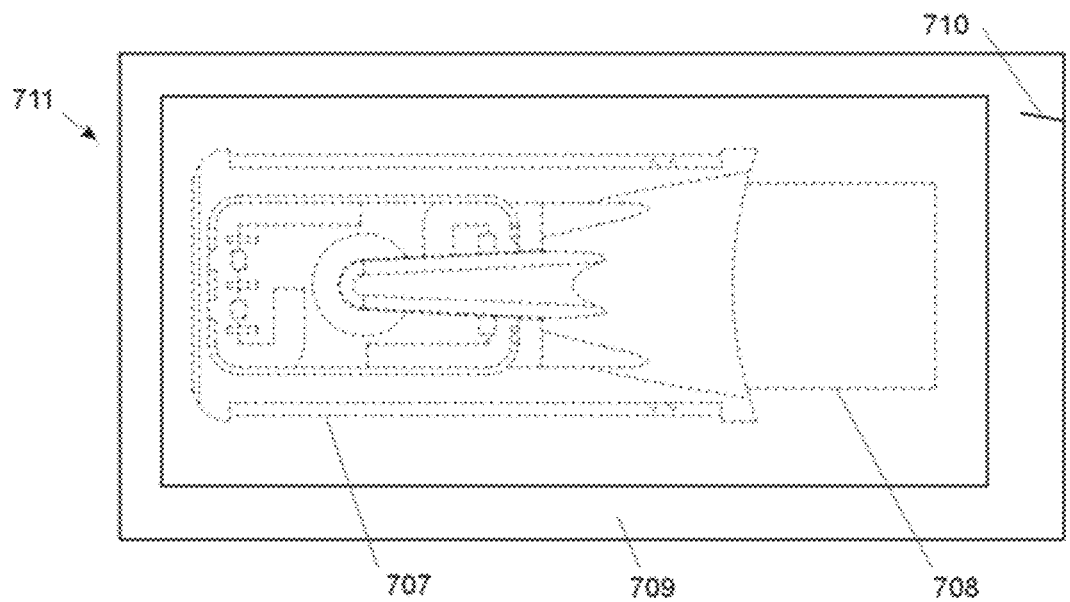
FIGS. 52 and 53 are top views of a medicament delivery device and packaging system, according to an embodiment.
Figure 53:
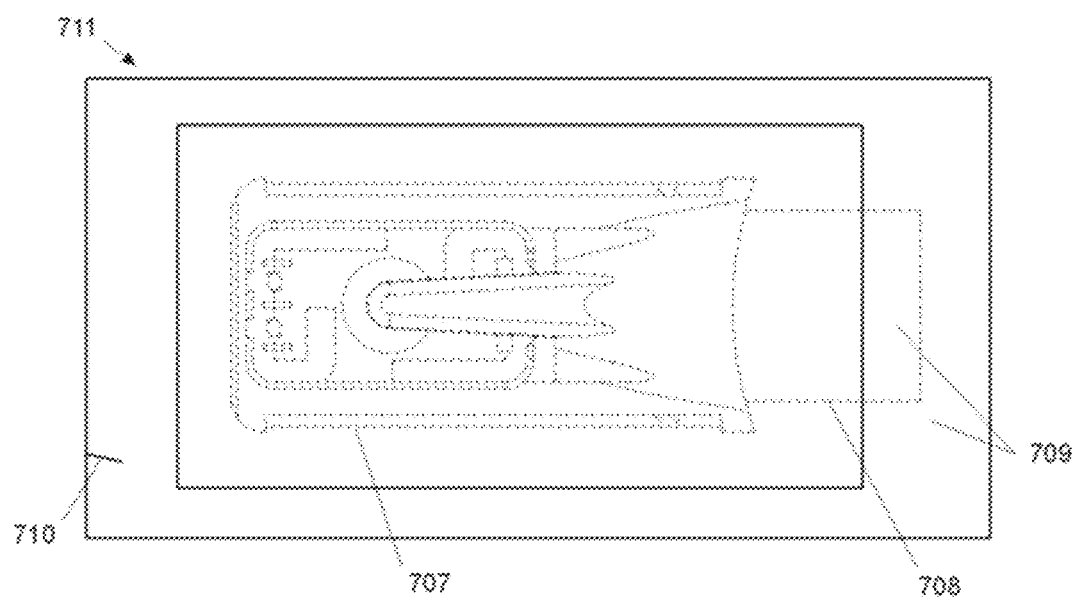

In addition to the concept shown in FIG. 50, the activation trip (pull tab) 708 may be sealed between the layers of the overwrap 711 as shown in FIG. 51. In this embodiment, the user can tear or peel open the overwrap 711 at the slit 710 location, and remove the inhaler 707 from the overwrap 711. Since the activation strip (pull tab) 708 is sealed to the overwrap, the activation strip (pull tab) 708 would be removed from the inhaler as the inhaler 707 as its pulled out of the overwrap 711. This packaging design eliminates one user operational step to simplify use and administration.

In some embodiments, a kit includes a package containing a dry powder inhaler and an applicator. The dry powder inhaler is configured to deliver a unit dose of a dry powder medicament. The applicator is configured to be removably coupled to the dry powder inhaler and allows a caregiver to position the dry powder inhaler for a user without touching the patient or the dry powder inhaler. In this manner, the applicator facilitates maintaining sterility during drug delivery. For example, any of the inhalers described herein may be administered to the patient with use of a wand or holder to help prevent cross contamination from the patient to nurse or caregiver. The wand would clamp onto the inhaler at the rear non-patient contact end and after dose delivery a hand grip located trigger release would be activated for ejection from the wand and disposal of the spent single use inhaler.

Compositions

In some embodiments, any of the medicament delivery devices described herein can include any suitable medicament, nutraceutical, or composition. In some embodiments, any of the medicament delivery devices (or drug products) described herein can include a composition including any suitable active pharmaceutical ingredient (API), any suitable excipient, bulking agent, carrier particle, or the like.

In some embodiments, the API can include albuterol sulfate (also referred to as "sulphate," for example, in Europe). In other embodiments, any of the drug products described herein can include any other bronchodilator. For example, in some embodiments the API can include a short-acting bronchodilator, such as, for example, levalbuterol, ipratropium, albuterol/ipratropium, pirbuterol, and/or fenoterol. For example, in some embodiments the API can include a long-acting bronchodilator, such as, for example, aclidinium (Tudorza), arformoterol (Brovana), formoterol (Foradil, Perforomist), glycopyrrolate (SeebriNeohaler), indacaterol (Arcapta), olodaterol (Striverdi Respimat), salmeterol (Serevent), tiotropium bromide (Spiriva), umeclidinium (IncruseEllipta), mometasone furoate powder, flunisolide, budesonide, and/or vilanterol.

In some embodiments, the API included in any of the drug products described herein can include methylxanthines or theophylline.

In some embodiments, the API included in any of the drug products described herein can include a combination drug. Such combination drugs can be, for example, a combination of either of two long-acting bronchodilators or of an inhaled corticosteroid and a long-acting bronchodilator. Suitable combination drugs include glycopyrrolate/formoterol (Bevespi Aerosphere), glycopyrrolate/indacaterol (UtibronNeohaler), tiotropium/olodaterol (StioltoRespimat), umeclidinium/vilanterol (AnoroEllipta), budesonide/formoterol (Symbicort), fluticasone/salmeterol (Advair), fluticasone/vilanterol (BreoEllipta). Although listed as including "double" combinations, in other embodiments, a drug product described herein can include triple (or quadruple) combinations.

In some embodiments, the API included in any of the drug products described herein can include Roflumilast.

In some embodiments, the API included in any of the drug products described herein can include a salt or ester such as sulfate (sulphate), or propionate or bromide.

In some embodiments, the API included in any of the drug products described herein can include any suitable SABA (short acting beta-agonist), LABA (long acting beta-agonist), LAMA (long acting muscarinic agent), SAMA (short acting muscarinic agent), or ICS (inhaled corticosteroid). For example, inhaled corticosteroids can include any of the corticosteroids described herein (e.g., flunisolide), as well as others, including fluticasone, mometasone, ciclesonide, or beclomethasone.

In some embodiments, the API included in any of the drug products described herein can include any suitable inhaled anti-infective composition. Such compositions can include, for example, ribavirin, tobramycin, zanamivir, pentamidine, gentamicin, cidofovir, or any combination of these.

In some embodiments, the API included in any of the drug products described herein can include any suitable inhaled antibiotic and/or antiviral composition. Such compositions can include, for example, antibiotics used to treat tularemia, including streptomycin, gentamicin, doxycycline, and ciprofloxacin. Such compositions can include, for example, antibiotics used to treat inhalational anthrax. Considerable progress in finding new drugs and suitable therapy for treatment of anthrax has been achieved, and such compositions can include levofloxacin, daptomycin, gatifloxacin, and dalbavancin. Such compositions can include, for example, antivirals to treat or prevent influenza (i.e. Relenza-zanamivir—5 mg doses), antivirals used to treat adenovirus pneumonia (e.g., brincidofovir), antivirals to treat RSV (e.g., Ribavirin).

In some embodiments, the API included in any of the drug products described herein can include any suitable inhaled composition for patients with cystic fibrosis. Such compositions can include, for example, tobramycin, aztreonam, colistin, mannitol, or pulmozyme.

In some embodiments, the API included in any of the drug products described herein can include any suitable inhaled vaccine. Such vaccines include, for example, influenza vaccines, tuberculosis vaccines, malaria vaccines, or any other vaccine suitable for delivery in an inhaled powder form.

In some embodiments, the API included in any of the drug products described herein can include any suitable composition for treating migraine headaches. Such compositions include, for example, Dihydroergotamine, Imitrex, sumatriptan, Maxalt, Relpax, Amerge, Axert, Butalbital compound, Zomig, Cambia, Treximet, Excedrine, Fiorinal, rizatriptan, gabapentin, Frova, Reglan, cyclobenzaprine, naratriptan, Norflex, diclofenac, and Methergine.

In some embodiments, the API included in any of the drug products described herein can include any suitable inhaled medicament for treating anaphylaxis, croup, asthma, or the like. Such compositions can include a local anesthetic. Such compositions can include epinephrine.

In some embodiments, the API included in any of the drug products described herein can include any suitable inhaled proteins and peptides. Such compositions can include, for example, insulin.

In some embodiments, the API included in any of the drug products described herein can include any suitable inhaled medicaments for biodefense (i.e., antidote treatment nerve agents). Such compositions can include, for example, Atropine or Atropine Sulfate, Pralidoxime, a combination of Atropine and Pralidoxime, Diazepam. Such compositions can be included to treat any indication, such as for use as a sedative to treat anxiety, muscle spasms, and seizures.

In some embodiments, the API included in any of the drug products described herein can include loxapine, alprazolam, fentanyl, or zaleplon.

Suitable excipients can include any composition or additive that form, along with the API, the desired formulation for filling, long term storage, delivery to the target location, or the like. Examples of suitable excipients include lactose, magnesium stearate, magnesium stearate-treated lactose carrier particles, trehalose, any sugars for use as cryoprotectants (e.g., mannitol), compositions used as solubility enhancers (e.g., cyclodextrine), and any combination of the above, including double, triple, or any other combination(s).

In some embodiments, the composition included in any of the drug products described herein can include any suitable naturally-occurring composition, such as nicotine, cannabinoids, or the like.

The drug product 100 (and any of the drug products described herein) can have any suitable size (e.g., length, width and/or depth) and can contain any suitable volume (or dose amount) of the medicament. In this manner, the chamber 125 (or any chambers described herein) can be configured to provide a desired fill volume and/or weight, and emitted dose (mass). In some embodiments, for example, the volume of the chamber 125 (or any chamber described herein) can be such that the fill weight of the composition is approximately 10 mg and the delivery amount of the composition is approximately 10 mg (providing an emitted dose percentage of approximately 85 percent). In other embodiments, however, the dose size (or weight) can range from 5 mg to 50 mg.

The fill weight and/or delivered dose (mass) can be adjusted such that any of the drug products described herein can include and/or deliver a suitable dose for patients within any suitable range. For example, in some embodiments, any of the drug products described herein can deliver a dose suitable for a pediatric patient (e.g., weighing less than 30 kg) or an adult patient (weighing 30 kg or more).

Although shown as defining a reservoir or chamber (e.g., the chamber 125) within which a medicament is directly disposed, in other embodiments, any of the drug products described herein can include a pre-sealed container that contains the medicament, and that is disposed within the chamber (e.g., the chamber 125) during manufacturing. In this manner, the assembly of the upper member and lower member can be completed in one location and the drug fill/finish operation can be performed in a different location.

In some embodiments, all or a portion of any of the drug products described herein can be color-coded for easier identification (e.g., within hospitals, etc.). In some embodiments, for example, a portion of either the upper member (e.g., upper member 150) or the lower member (e.g., lower member 120), or both, or additional parts, can be colored. The coloring can indicate any number of parameters associated with the drug product, such as, the medicament, the dose (e.g., adult, pediatric, etc.), and/or the expiration date. In other embodiments, the partition (not shown, but described above) can be colored.

In some embodiments, any of the drug products described herein can include a partition (or seal) that maintains the medicament within the chamber (e.g., the chamber 125). In some embodiments, the partition can be coupled to the lower member (e.g., the lower member 120) via a small spot seal in conjunction with clamping forces produced between the upper member and the lower member. In use, the spot seals can be configured to rupture, break or tear to facilitate removal of the partition from between the upper member and the lower member.

In some embodiments, any of the drug products described herein can be included within an overwrap (or package) when in its assembled state. In this manner, the mouthpiece of the device can be maintained in a sterile environment during storage. In some embodiments, an end portion of a partition is coupled to the overwrap such that removal of the overwrap also removes the partition, thus preparing (or readying) the device for use.

In some embodiments, a kit includes a medicament delivery device and an applicator. The medicament delivery device can be any of the medicament delivery devices (or drug products) described herein, such as the drug product 100 or the drug product 200. The applicator is configured to be removably coupled to drug product. This arrangement allows a caregiver to position the drug product for use by a user without touching the user or the dry powder inhaler. In this manner, the applicator facilitates maintaining sterility during drug delivery. In some embodiments, the applicator can include an actuator, lever, button, or the like to release the drug product for use by the patient. In some embodiments, the applicator can contain all or a portion of the drug product (e.g., the proximal end). In other embodiments, the applicator can be disposed within an opening, notch or recess defined by either the upper member or the lower member of the drug product.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the raised surface 126 is shown as being a flat surface, in other embodiments, any of the raised surfaces described herein can have any suitable shape. For example, in some embodiments, any of the raised surfaces described herein can have curved or spherical surface. In some embodiments, any of the raised surfaces described herein can have a conical surface and/or can be raised to terminate in a point, or be polygonal, ramped or irregular in shape. In other embodiments, any of the raised surfaces described herein can include a series of protrusions, posts or extensions that impact the flow around and/or through the area of the surface.

Moreover, in some cases, the patient may mistakenly breathe out and into the inhaler prior to inhalation. In other words, in some cases, the patient may blow in the reverse direction into the inhaler. In such cases the raised surface (or plateau), such as for example, the raised surface 126, serves as an air deflection surface to deflect the reverse direction air flow to the four air channels (e.g., the channels 160A-D and openings 163A-D) while powder resides safely in the bottom of the dose chamber. The plateau 126 may be flat as shown in FIG. 13 or convex, concave, ramped or with polygonal surfaces aimed to direct reverse air flow to the four openings 163A-D, for example. This concept may be applied to inhaler embodiments with two or more air inlets.

In some embodiments, the air inlets and outlets into and out of any of the dose chambers described herein (e.g., the dose chamber 125) are be designed to disaggregate and deliver all particles of the powder contained therein. In other embodiments, the air inlets and outlets into and out of any of the dose chambers described herein (e.g., the dose chamber 125) can be designed to separate particles with the chamber based on size, mass, geometry, with smaller particles exiting through the outlet and predominately larger lactose carrier particles remaining in the dose chamber after dose delivery. Larger lactose carrier particles with greater mass and centrifugal force flow along the outside walls of the chamber, and have sufficient mass and momentum to withstand air inlet flow jets and eddy currents. Thus, such larger particles remain flowing along the outside walls throughout the inhalation event. Once the inhalation event is complete, the larger lactose particles settle in the bottom of the dose chamber. The recirculation of these larger lactose particles and resulting impact forces is important for breaking the attractive bonds (forces) between drug (API) and lactose particles, as well as breaking up agglomerates. In addition, less lactose or excipient is delivered to the patient which may be beneficial for dosing regimens involving frequent dosing and high powder loading in the patient's lungs.

Although various embodiments have been described as having particular features and/or combinations of components, other embodiments are possible having a combination of any features and/or components from any of embodiments where appropriate. For example, any of the devices shown and described herein can include any of the ramps, protrusion, or other flow structures, as described herein. For example, although the medicament delivery device 100 shown in FIGS. 9-10 is not shown as including any flow structures (e.g., the ramps 331), in other embodiments, a medicament delivery device similar to the device 100 can include one or more flow ramps, similar to the ramps 331 shown and described above.

Any of the medicament containers described herein can contain any of the epinephrine compositions and/or other drug formulations described herein.

What is claimed is:

1. An apparatus, comprising:
   a first member defining at least a portion of a disaggregation chamber containing a dry powder, the first member including a chamber wall that forms an outer boundary of the disaggregation chamber; and
   a second member coupled to the first member, the second member including a surface covering the disaggregation chamber, the second member defining an intake channel and an exit channel, the exit channel configured to be fluidically coupled to the disaggregation chamber via an exit opening defined by the surface of the second member, the intake channel configured to be fluidically coupled to the disaggregation chamber via an intake port, a center line of a portion of the intake channel being tangential to a portion of the chamber wall of the first member such that a portion of an inlet airflow conveyed into the disaggregation chamber via the intake channel has a rotational motion about a center axis of the disaggregation chamber, the intake port defined at least in part by an intake ramp, the intake ramp including a transition surface that forms an exit angle with respect to the surface of between 75 degrees and 105 degrees.

2. The apparatus of claim 1, wherein the transition surface of the intake ramp is parallel to the center axis.

3. The apparatus of claim 1, wherein:
   the chamber wall is an outer chamber wall surrounding the center axis; and
   the first member includes an inner chamber wall that forms an inner boundary of the disaggregation chamber, the inner chamber wall surrounding the center axis.

4. The apparatus of claim 3, wherein the inner chamber wall terminates in a raised surface, the center axis intersecting the raised surface, the exit opening being along the center axis opposite the raised surface.

5. The apparatus of claim 4, wherein the second member includes a protrusion extending from the surface of the second member, the protrusion in contact with the raised surface to maintain a distance between the raised surface and the exit opening.

6. The apparatus of claim 5, wherein:
   the portion of the disaggregation chamber is a first portion; and
   the surface of the second member defines a second portion of the disaggregation chamber.

7. The apparatus of claim 1, further comprising:
   a strip disposed between the first member and the second member, the strip retaining the dry powder within the portion of the disaggregation chamber, the strip fluidically isolating the portion of the disaggregation chamber from the intake channel and the exit channel when the strip is in a first position, the strip configured to be moved relative to the first member to a second position, the portion of the disaggregation chamber in fluid communication with the intake channel and the exit channel when the strip is in the second position.

8. The apparatus of claim 1, wherein the dry powder includes any one of albuterol sulfate, levalbuterol, ipratropium, albuterol/ipratropium, pirbuterol, or fenoterol.

9. The apparatus of claim 1, wherein the dry powder includes a bronchodilator and a non-sieved lactose excipient.

10. The apparatus of claim 1, wherein the first member and the second member are monolithically constructed with a living hinge between the first member and the second member.

11. An apparatus, comprising:
    a first member defining at least a portion of a disaggregation chamber containing a dry powder, the first member including a chamber wall that forms an outer boundary of the disaggregation chamber; and
    a second member coupled to the first member, the second member including a surface covering the disaggregation chamber, the second member defining an intake channel and an exit channel, the exit channel fluidically coupled to the disaggregation chamber via an exit opening defined by the surface of the second member, the intake channel configured to be fluidically coupled to the disaggregation chamber via an intake port, a center line of the intake channel being tangential to a portion of the chamber wall of the first member such that a first portion of an inlet airflow conveyed into the disaggregation chamber via the intake channel has a rotational motion about the exit opening, the intake port defined at least in part by an intake ramp, the intake ramp curved radially outwardly towards the chamber wall such that a second portion of the inlet airflow conveyed into the disaggregation chamber via the intake channel is conveyed directly towards the chamber wall.

12. The apparatus of claim 11, wherein:
    the first portion of the inlet airflow rotates about a center axis; and
    the intake ramp defines a first radius of curvature within a first plane normal to the center axis and a second radius of curvature within a second plane normal to the first plane, the first radius of curvature and the second radius of curvature each opening outwardly towards the chamber wall.

13. The apparatus of claim 11, wherein the intake ramp terminates at the surface of the second member with an exit angle of between 75 degrees and 105 degrees.

14. The apparatus of claim 11., further comprising:
a strip disposed between the first member and the second member, the strip retaining the dry powder within the portion of the disaggregation chamber, the strip fluidically isolating the portion of the disaggregation chamber from the intake channel and the exit channel when the strip is in a first position, the strip configured to be moved relative to the first member to a second position, the portion of the disaggregation chamber in fluid communication with the intake channel and the exit channel when the strip is in the second position.

15. The apparatus of claim 14, wherein:
the second member includes a mouthpiece defining a mouthpiece opening in fluid communication with the exit channel;

the strip includes a pull portion extending beyond the mouthpiece; and the first member and the second member define a relief volume that maintains a relief distance between the first member and the second member.

16. The apparatus of claim 15, wherein at least one of the first member or the second member defines a contact wall that forms a boundary of the relief volume.

17. The apparatus of claim 14, wherein:
the chamber wall is an outer chamber wall surrounding a center axis aboutwhich the first portion of the inlet airflow rotates;

the dry powder is formed as a compressed plug; and the first member including a bottom chamber wall that forms a bottom boundary of the disaggregation chamber, the bottom chamber wall including a target surface for placement of the compressed plug of the dry powder.

18. An apparatus, comprising:
a first member defining at least a first portion of a disaggregation chamber containing a dry powder, the first member including a raised surface along a center axis of the disaggregation chamber;

a second member coupled to the first member, the second member including a surface covering the disaggregation chamber, the second member defining an intake channel and an exit channel, the intake channel fluidically coupled to the disaggregation chamber via an intake port, the exit channel fluidically coupled to the disaggregation chamber via an exit opening defined by the surface of the second member, the exit opening being along the center axis, at least one of the first member or the second member including a protrusion extending from the surface of the second member and contacting; the raised surface of the first member to maintain a distance between the raised surface and the exit opening.

19. The apparatus of claim 18, wherein:

the surface of the second member is an inner surface; and the intake channel is fluidically coupled to an external volume outside of the disaggregation chamber by an external opening defined by an outer surface of the second member, the outer surface including a plurality of barrier surfaces at least partially surrounding the external opening, the plurality of barrier surfaces configured to limit obstruction of the external opening.

20. The apparatus of claim 19, wherein the intake channel includes a tortuous path to limit movement of the dry powder from the disaggregation chamber through the intake channel and the external opening.

21. The apparatus of claim 18, wherein the protrusion is one of a plurality of protrusions between the surface of the second member and the raised surface of the first member.

22. The apparatus of claim 18, further comprising:

a strip disposed between the first member and the second member, the strip retaining the dry powder within the first portion of the disaggregation chamber, the strip fluidically isolating the first portion of the disaggregation chamber from the intake channel and the exit channel when the strip is in a first position, the strip configured to be moved relative to the first member to a second position, the first portion of the disaggregation chamber in fluid communication with the intake channel and the exit channel when the strip is in the second position.

23. The apparatus of claim 18, wherein the dry powder includes any one of a bronchodilator, a corticosteroid, or a muscarinic agent.

24. The apparatus of claim 18, wherein the dry powder includes any one of albuterol sulfate, levaibuterol, ipratropium, albuterol/ipratropium, pirbuterol, fenoterol, or vilanterol.

25. The apparatus of claim 18, wherein the dry powder includes any one of fluticasone, mometasone, ciclesonide, or beclomethasone.

26. The apparatus of claim 18, wherein the dry powder includes tiotropium bromide.

* * * * *

UNITED STATES PATENT AND TRADEMARK OFFICE
CERTIFICATE OF CORRECTION

PATENT NO. : 10,456,537 B2
APPLICATION NO. : 15/938766
DATED : October 29, 2019
INVENTOR(S) : Eric C. Richardson et al.

It is certified that error appears in the above-identified patent and that said Letters Patent is hereby corrected as shown below:

In the Specification

Column 4, Lines 53-54, delete "FIG. 43 is a top view of a portion of a medicament delivery device, according to an embodiment."

In the Claims

Claim 17, Line 3 (Column 43, Line 33), change "aboutwhich" to --about which--

Claim 24, Line 2 (Column 44, Line 42), change "levaibuterol" to --levalbuterol--

Signed and Sealed this
Tenth Day of December, 2019

Andrei Iancu
*Director of the United States Patent and Trademark Office*